US010435491B2

(12) United States Patent
Bischof et al.

(10) Patent No.: US 10,435,491 B2
(45) Date of Patent: Oct. 8, 2019

(54) METHOD FOR MAKING POLYALPHAOLEFINS USING IONIC LIQUID CATALYZED OLIGOMERIZATION OF OLEFINS

(71) Applicants: Chevron Phillips Chemical Company LP, The Woodlands, TX (US); Chevron U.S.A. Inc., San Ramon, CA (US)

(72) Inventors: Steven M. Bischof, Humble, TX (US); Robert C. Coffin, Kingwood, TX (US); Kenneth D. Hope, Kingwood, TX (US); Michael S. Driver, Oakland, CA (US); Hye-Kyung Timken, Albany, CA (US)

(73) Assignee: Chevron Phillips Chemical Company LP, The Woodlands, TX (US)

( * ) Notice: Subject to any disclaimer, the term of this patent is extended or adjusted under 35 U.S.C. 154(b) by 28 days.

(21) Appl. No.: 14/829,987

(22) Filed: Aug. 19, 2015

(65) Prior Publication Data
US 2017/0051087 A1 Feb. 23, 2017

(51) Int. Cl.
*C07C 2/22* (2006.01)
*C07C 2/26* (2006.01)
(Continued)

(52) U.S. Cl.
CPC ......... *C08F 110/14* (2013.01); *B01J 31/0231* (2013.01); *B01J 31/0284* (2013.01); *C07C 2/22* (2013.01); *C07C 2/26* (2013.01); *C07C 5/03* (2013.01); *C10G 50/00* (2013.01); *C10G 50/02* (2013.01); *C07C 2527/08* (2013.01); *C07C 2527/11* (2013.01); *C07C 2527/125* (2013.01); *C07C 2531/02* (2013.01)

(58) Field of Classification Search
CPC .................................. C08F 110/14; C07C 2/22
USPC .................................. 585/255, 521, 502, 520
See application file for complete search history.

(56) References Cited

U.S. PATENT DOCUMENTS 1,815,022 A 7/1931 Davis
2,015,748 A 10/1935 Frolich
(Continued)

FOREIGN PATENT DOCUMENTS

EP 0791643 A1 8/1997
WO 9521871 A1 8/1995
(Continued)

OTHER PUBLICATIONS

ChemicalBook ("1-Butylpyridinium chloroaluminate"; http://www.chemicalbook.com (2016)).*
(Continued)

*Primary Examiner* — Philip Y Louie
(74) *Attorney, Agent, or Firm* — Conley Rose, P.C.

(57) ABSTRACT

Disclosed herein are embodiments of a process which generally includes contacting i) a monomer or mixture of monomers, ii) a haloaluminate ionic liquid, and iii) one or more halide components in a reaction zone, and oligomerizing the monomer or mixture of monomers in the reaction zone to form an oligomer product. The combination of the haloaluminate ionic liquid and halide component can constitute a catalyst system which is used in embodiments of the process to produce the oligomer product.

20 Claims, 7 Drawing Sheets

(51) Int. Cl.
*C08F 110/14* (2006.01)
*C10G 50/00* (2006.01)
*C10G 50/02* (2006.01)
*B01J 31/02* (2006.01)
*C07C 5/03* (2006.01)

(56) References Cited

U.S. PATENT DOCUMENTS

| | | |
|---|---|---|
| 2,191,498 A | 2/1940 | Reiff |
| 2,387,501 A | 10/1945 | Dietrich |
| 2,443,264 A | 6/1948 | Mikeska |
| 2,471,115 A | 5/1949 | Mikeska |
| 2,526,497 A | 10/1950 | Mikeska |
| 2,591,577 A | 4/1952 | McDermott |
| 2,655,479 A | 10/1953 | Munday et al. |
| 2,666,746 A | 1/1954 | Munday et al. |
| 2,719,125 A | 9/1955 | Roberts |
| 2,719,126 A | 9/1955 | Fields et al. |
| 2,721,877 A | 10/1955 | Popkin et al. |
| 2,721,878 A | 10/1955 | Popkin |
| 3,036,003 A | 5/1962 | Verdol |
| 3,087,932 A | 4/1963 | Little, Jr. |
| 3,087,936 A | 4/1963 | Le Suer |
| 3,172,892 A | 3/1965 | Le Suer et al. |
| 3,200,107 A | 8/1965 | Le Suer |
| 3,215,707 A | 11/1965 | Rense |
| 3,219,666 A | 11/1965 | Norman et al. |
| 3,250,715 A | 5/1966 | Wyman |
| 3,254,025 A | 5/1966 | Le Suer |
| 3,272,746 A | 9/1966 | Le Suer et al. |
| 3,275,554 A | 9/1966 | Wagenaar |
| 3,316,177 A | 4/1967 | Dorer, Jr. |
| 3,322,670 A | 5/1967 | Burt et al. |
| 3,329,658 A | 7/1967 | Fields |
| 3,341,542 A | 9/1967 | Le Suer et al. |
| 3,413,347 A | 11/1968 | Worrel |
| 3,438,757 A | 4/1969 | Honnen et al. |
| 3,444,170 A | 5/1969 | Norman et al. |
| 3,449,250 A | 6/1969 | Fields |
| 3,454,555 A | 7/1969 | van der Voort et al. |
| 3,454,607 A | 7/1969 | Le Suer et al. |
| 3,519,565 A | 7/1970 | Coleman |
| 3,541,012 A | 11/1970 | Stuebe |
| 3,565,804 A | 2/1971 | Honnen et al. |
| 3,630,904 A | 12/1971 | Musser et al. |
| 3,632,511 A | 1/1972 | Liao |
| 3,652,616 A | 3/1972 | Watson et al. |
| 3,666,730 A | 5/1972 | Coleman |
| 3,687,849 A | 8/1972 | Abbott |
| 3,697,574 A | 10/1972 | Piasek et al. |
| 3,702,300 A | 11/1972 | Coleman |
| 3,703,536 A | 11/1972 | Piasek et al. |
| 3,704,308 A | 11/1972 | Piasek et al. |
| 3,725,277 A | 4/1973 | Worrel |
| 3,725,480 A | 4/1973 | Traise et al. |
| 3,726,882 A | 4/1973 | Traise et al. |
| 3,751,365 A | 8/1973 | Piasek et al. |
| 3,755,433 A | 8/1973 | Miller et al. |
| 3,756,953 A | 9/1973 | Piasek et al. |
| 3,770,854 A | 11/1973 | Morris et al. |
| 3,787,374 A | 1/1974 | Adams |
| 3,798,165 A | 3/1974 | Piasek et al. |
| 3,803,039 A | 4/1974 | Piasek et al. |
| 3,822,209 A | 7/1974 | Knapp et al. |
| 3,948,800 A | 4/1976 | Meinhardt |
| 4,045,507 A | 8/1977 | Cupples et al. |
| 4,100,082 A | 7/1978 | Clason et al. |
| 4,234,435 A | 11/1980 | Meinhardt et al. |
| 4,426,305 A | 1/1984 | Malec |
| 4,454,059 A | 6/1984 | Pindar et al. |
| 4,501,678 A | 2/1985 | Katayama et al. |
| 4,767,551 A | 8/1988 | Hunt et al. |
| 4,798,684 A | 1/1989 | Salomon |
| 4,941,984 A | 7/1990 | Chamberlin, III et al. |
| 5,034,141 A | 7/1991 | Beltzer et al. |
| 5,034,142 A | 7/1991 | Habeeb et al. |
| 5,084,197 A | 1/1992 | Galic et al. |
| 5,573,657 A | 11/1996 | Degnan et al. |
| 5,693,598 A | 12/1997 | Abraham et al. |
| 5,705,458 A | 1/1998 | Roby et al. |
| 6,395,948 B1 | 5/2002 | Hope et al. |
| 6,969,693 B2 | 11/2005 | Sauvage et al. |
| 6,984,605 B2 | 1/2006 | Hope et al. |
| 7,256,152 B2 | 8/2007 | Olivier-Bourbigou et al. |
| 7,309,805 B2 | 12/2007 | Hope et al. |
| 7,342,143 B2 | 3/2008 | Birke et al. |
| 7,351,780 B2 | 4/2008 | Hope et al. |
| 7,495,144 B2 | 2/2009 | Elomari |
| 7,572,943 B2 | 8/2009 | Elomari et al. |
| 7,572,944 B2 | 8/2009 | Elomari et al. |
| 7,576,252 B2 | 8/2009 | Elomari et al. |
| 7,691,771 B2 | 4/2010 | Harris et al. |
| 7,723,556 B2 | 5/2010 | Elomari et al. |
| 7,732,363 B2 | 6/2010 | Elomari et al. |
| 7,732,364 B2 | 6/2010 | Chang et al. |
| 7,754,636 B2 | 7/2010 | Elomari et al. |
| 7,807,597 B2 | 10/2010 | Elomari et al. |
| 7,951,889 B2 | 5/2011 | Bergman et al. |
| 8,012,899 B2 | 9/2011 | Hommeltoft |
| 8,101,809 B2 | 1/2012 | Elomari et al. |
| 8,124,821 B2 | 2/2012 | Elomari et al. |
| 8,128,739 B1 | 3/2012 | Gupta |
| 8,178,739 B2 | 5/2012 | Elomari et al. |
| 8,203,026 B2 | 6/2012 | Elomari et al. |
| 8,222,471 B2 | 7/2012 | Elomari et al. |
| 8,237,004 B2 | 8/2012 | Timken et al. |
| 8,388,903 B2 | 3/2013 | Hommeltoft et al. |
| 8,471,086 B2 | 6/2013 | Hommeltoft |
| 8,487,154 B2 | 7/2013 | Timken et al. |
| 8,524,968 B2 | 9/2013 | Elomari et al. |
| 8,729,329 B2 | 5/2014 | Hommeltoft et al. |
| 8,772,035 B2 | 7/2014 | Timken et al. |
| 8,871,154 B2 | 10/2014 | Hommeltoft |
| 9,079,176 B1* | 7/2015 | Smith ................. B01J 31/4053 |
| 2002/0128532 A1 | 9/2002 | Hope et al. |
| 2004/0030075 A1 | 2/2004 | Hope et al. |
| 2004/0267070 A1 | 12/2004 | Johnson et al. |
| 2005/0113621 A1* | 5/2005 | Hope ..................... C07C 2/22 585/521 |
| 2005/0119423 A1 | 6/2005 | Bergman et al. |
| 2006/0020088 A1 | 1/2006 | Hope et al. |
| 2006/0135839 A1 | 6/2006 | Elomari et al. |
| 2006/0247482 A1 | 11/2006 | Hope et al. |
| 2007/0142684 A1 | 6/2007 | Elomari et al. |
| 2007/0142685 A1* | 6/2007 | Elomari ............... C10M 105/04 585/332 |
| 2007/0142690 A1 | 6/2007 | Elomari |
| 2007/0142691 A1 | 6/2007 | Elomari et al. |
| 2007/0225538 A1 | 9/2007 | Elomari |
| 2008/0142413 A1 | 6/2008 | Harris et al. |
| 2008/0306319 A1 | 12/2008 | Earle et al. |
| 2009/0050521 A1 | 2/2009 | Elomari et al. |
| 2009/0156874 A1 | 6/2009 | Patil et al. |
| 2009/0163750 A1 | 6/2009 | Timken et al. |
| 2009/0170687 A1 | 7/2009 | Luo et al. |
| 2009/0270666 A1 | 10/2009 | Elomari et al. |
| 2009/0270667 A1 | 10/2009 | Elomari et al. |
| 2009/0306444 A1 | 12/2009 | Elomari et al. |
| 2010/0065476 A1* | 3/2010 | Hommeltoft ........ C10G 29/205 208/108 |
| 2010/0158762 A1 | 6/2010 | Lacheen et al. |
| 2010/0317904 A1 | 12/2010 | Small et al. |
| 2011/0021850 A1* | 1/2011 | Battersby ............. C10M 105/04 585/16 |
| 2011/0034742 A1 | 2/2011 | Elomari et al. |
| 2011/0034743 A1 | 2/2011 | Elomari et al. |
| 2011/0034748 A1 | 2/2011 | Elomari et al. |
| 2011/0155640 A1* | 6/2011 | Timken .................. C10G 7/00 208/97 |
| 2011/0226669 A1* | 9/2011 | Timken ................ B01J 31/0277 208/134 |
| 2012/0149612 A1 | 6/2012 | Elomari et al. |
| 2012/0149953 A1 | 6/2012 | Elomari et al. |

(56) References Cited

U.S. PATENT DOCUMENTS

| | | | |
|---|---|---|---|
| 2012/0165586 A1* | 6/2012 | Timken | B01J 31/0284 585/330 |
| 2012/0172641 A1 | 7/2012 | Elomari et al. | |
| 2012/0172644 A1* | 7/2012 | Elomari | C10G 50/02 585/310 |
| 2012/0296145 A1 | 11/2012 | Lacheen | |

FOREIGN PATENT DOCUMENTS

| | | |
|---|---|---|
| WO | 9521872 A1 | 8/1995 |
| WO | 03089390 A2 | 10/2003 |
| WO | 2005042447 A1 | 5/2005 |
| WO | 2014033736 A1 | 3/2014 |

OTHER PUBLICATIONS

Matkovskii et al., Effect of the alkyl chloride-to-aluminum molar ratio in the catalysts of dec-1-ene oligomerization on the product distribution and the chlorine content in the products, Russian Chemical Bulletin, International Edition, vol. 57, No. 3, pp. 674-678, Mar. 2008. (Year: 2008).*

Enderby, John E., "Ionic liquids: recent progress and remaining problems," J. Phys.: Condens. Matter, 1993, pp. B99-B106, vol. 5, IOP Publishing Ltd.

Freemantle, Michael, "Designer Solvents, Ionic liquids may boost clean technology development," C&EN, Mar. 30, 1998, pp. 32-37.

Gee, Jeffrey C., et al., "Behavior of protonated cyclopropyl intermediates during polyalphaolefin synthesis: Mechanism and predicted product distribution," Journal of Physical Organic Chemistry, 2012, pp. 1409-1417, vol. 25, John Wiley & Sons, Ltd.

Gordon, Charles M., et al., "Ionic liquid crystals: hexafluorophosphate salts," J. Mater. Chem., 1998, pp. 2627-2636, vol. 8.

"Group notation revised in periodic table," Feb. 4, 1985, pp. 26-27, C&EN.

Klamann, Dieter, et al., "Lubricants and Related Products," 1984, pp. 199-248 plus 1 cover page, Verlag Chemie.

Mang, Theo, et al., "Lubricants and Lubrication," 2001, 1 page, Wiley-VCH.

McNaught, Alan D., et al., "Compendium of Chemical Terminology," International Union of Pure and Applied Chemistry, Second edition, 1997, 5 pages of cover, publishing information, and contents, Wiley-Blackwell.

Ranney, M. W., "Lubricant Additives," Chemical Technology Review No. 2, 1973, 352 pages, Noyes Data Corporation.

Ranwell A., et al., "Potential Application of Ionic Liquids for Olefin Oligomerization," Chapter 12 of "Ionic Liquids," by R. Rogers, et al., 2002, pp. 147-160, ACS Symposium Series, American Chemical Society.

Rudnick, Leslie R., et al., "Synthetic Lubricants and High-Performance Functional Fluids," 1999, 1 page, Second Edition, CRC Press.

Seddon, Kenneth R., "Ionic Liquids for Clean Technology," J. Chem. Tech. Biotechnol., 1997, pp. 351-356, vol. 68, SCI, Great Britain.

Sequeira, Jr., Avilino, "Lubricant Base Oil and Wax Processing," Chapter 6, "Lubricant Base Oil Hydrogen Refining Processes," pp. 119-152 plus 1 page cover and publishing information, Marcel Dekker, Inc.

Shubkin, R. L., et al., "Tailor-making Polyalphaolefins," Journal of Synthetic Lubrication, 1991, pp. 115-134 plus one page publishing information, vol. 8, Issue 2, John Wiley & Sons, Ltd.

Smalheer, C. V., et al., "Lubricant Additives," 1967, 91 pages, The Lezius-Hiles Co., The Lubrizol Corporation.

Totten, George E., et al., "Fuels and Lubricants Handbook: Technology, Properties, Performance, and Testing," 2003, 3 pages, ASTM International.

Wasserscheid, Peter, et al., "Synthesis of Synthetic Lubricants by Trimerization of 1-Decene and 1-Dodecene with Homogeneous Chromium Catalysts," Adv. Synth. Catal., 2001, pp. 814-818, vol. 343, No. 8, Wiley-VCH Verlag GmbH, Weinheim, Germany.

Welton, Thomas, "Room-Temperature Ionic Liquids. Solvents for Synthesis and Catalysis," Chem. Rev., 1999, pp. 2071-2083, vol. 99, No. 8, American Chemical Society.

Foreign communication from a related counterpart application—International Search Report and Written Opinion, PCT/US2016/043999, dated Nov. 7, 2016, 10 pages.

\* cited by examiner

METHOD FOR MAKING POLYALPHAOLEFINS USING IONIC LIQUID CATALYZED OLIGOMERIZATION OF OLEFINS

TECHNICAL FIELD

The present disclosure relates to a method of making an oligomer product and/or polyalphaolefins. More specifically, the present disclosure relates to a method of making oligomer product and/or polyalphaolefins using an ionic liquid catalyzed oligomerization of olefins (e.g., normal alpha olefins, linear internal olefins, etc.).

BACKGROUND

Oligomer products, hydrogenated oligomer products (e.g., polyalphaolefins) and their derivatives are used for the production of a wide variety of articles (e.g., synthetic lubricants or lubricant additives). The use of a particular oligomer product and/or hydrogenated oligomer product in a particular application will depend on the type of physical and/or mechanical properties displayed by the oligomer product and/or hydrogenated oligomer product, and such properties can be a result of the method used for producing a particular oligomer product and or hydrogenated oligomer product, e.g., the reaction conditions under which the oligomer product can be produced. Thus, there is an ongoing need to develop and improve methods for producing these oligomers, and hydrogenated oligomer products.

SUMMARY

Disclosed are embodiments of a process which generally include contacting i) a monomer or mixture of monomers, ii) a haloaluminate ionic liquid, and iii) one or more halide components (e.g., a Brönsted acid, an organohalide) in a reaction zone, and oligomerizing the monomer or mixture of monomers in the reaction zone to form an oligomer product. The oligomer product having the properties described herein can be isolated into one or more fractions, and the one or more fractions can be hydrogenated to yield polyalphaolefins. Isolating the one or more fractions from the oligomer product can include various techniques and separations as disclosed herein.

Also disclosed are embodiments of a catalyst system which comprise the haloaluminate ionic liquid and the halide component. The catalyst system can have various features as described herein which facilitate production of the disclosed oligomer product.

BRIEF DESCRIPTION OF THE DRAWINGS

For a more complete understanding of the present disclosure and the advantages thereof, reference is now made to the following brief description, taken in connection with the accompanying drawings and detailed description, wherein like reference numerals represent like parts.

DETAILED DESCRIPTION

Figure 1:
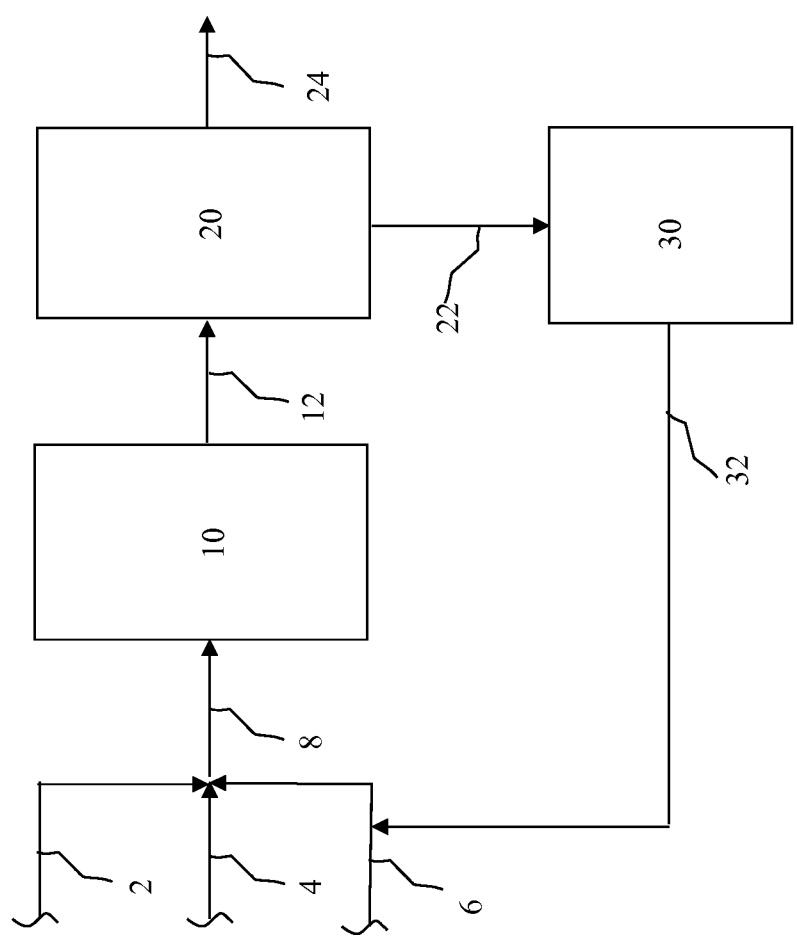
FIG. 1 illustrates the oligomerization of olefins using haloaluminate ionic liquids and recovery of an oligomer product.

Disclosed herein are methods of making an oligomer product and/or hydrogenated oligomer products (e.g., polyalphaolefins). In an embodiment, a method of the present disclosure comprises oligomerizing a monomer in the presence of an ionic liquid (e.g., a haloaluminate ionic liquid), an organohalide component, or both, to produce an oligomer product. At least a portion of the oligomer product can be recovered and/or hydrogenated to produce what is commonly referred to as polyalphaolefins (PAOs). In an embodiment, such method can result in PAOs with desirable properties, e.g., viscosity, pour point, and/or viscosity index, among other properties.

To define more clearly the terms used herein, the following definitions are provided. Unless otherwise indicated, the following definitions are applicable to this disclosure. If a term is used in this disclosure but is not specifically defined herein, the definition from the IUPAC Compendium of Chemical Terminology, $2^{nd}$ Ed (1997) can be applied, as long as that definition does not conflict with any other disclosure or definition applied herein, or render indefinite or non-enabled any claim to which that definition is applied. To the extent that any definition or usage provided by any document incorporated herein by reference conflicts with the definition or usage provided herein, the definition or usage provided herein controls.

Groups of elements of the Periodic Table are indicated using the numbering scheme indicated in the version of the Periodic Table of elements published in *Chemical and Engineering News,* 63(5), 27, 1985. In some instances a group of elements can be indicated using a common name assigned to the group; for example alkali earth metals (or alkali metals) for Group 1 elements, alkaline earth metals (or alkaline metals) for Group 2 elements, transition metals for Group 3-12 elements, and halogens for Group 17 elements.

A chemical "group" is described according to how that group is formally derived from a reference or "parent" compound, for example, by the number of hydrogen atoms formally removed from the parent compound to generate the group, even if that group is not literally synthesized in this manner. These groups can be utilized as substituents or coordinated or bonded to metal atoms. By way of example, an "alkyl group" formally can be derived by removing one hydrogen atom from an alkane, while an "alkylene group" formally can be derived by removing two hydrogen atoms from an alkane. Moreover, a more general term can be used to encompass a variety of groups that formally are derived by removing any number ("one or more") hydrogen atoms from a parent compound, which in this example can be described as an "alkane group," and which encompasses an "alkyl group," an "alkylene group," and materials having three or more hydrogens atoms, as necessary for the situation, removed from the alkane. Throughout, the disclosure a substituent, ligand, or other chemical moiety can constitute a particular "group" implies that the well-known rules of chemical structure and bonding are followed when that group is employed as described. When describing a group as being "derived by," "derived from," "formed by," or "formed from," such terms are used in a formal sense and are not intended to reflect any specific synthetic methods or procedure, unless specified otherwise or the context requires otherwise.

The term "substituted" when used to describe a compound or group, for example, when referring to a substituted analog of a particular compound or group, is intended to describe any non-hydrogen moiety that formally replaces a hydrogen in that group, and is intended to be non-limiting. A group or groups can also be referred to herein as "unsubstituted" or by equivalent terms such as "non-substituted," which refers to the original group in which a non-hydrogen moiety does not replace a hydrogen within that group. "Substituted" is intended to be non-limiting and include inorganic substituents or organic substituents.

Unless otherwise specified, any carbon-containing group for which the number of carbon atoms is not specified can have, according to proper chemical practice, 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 carbon atoms, or any range or combination of ranges between these values. For example, unless otherwise specified, any carbon-containing group can have from 1 to 30 carbon atoms, from 1 to 25 carbon atoms, from 1 to 20 carbon atoms, from 1 to 15 carbon atoms, from 1 to 10 carbon atoms, or from 1 to 5 carbon atoms, and the like. Moreover, other identifiers or qualifying terms can be utilized to indicate the presence or absence of a particular substituent, a particular regiochemistry and/or stereochemistry, or the presence or absence of a branched underlying structure or backbone.

Within this disclosure the normal rules of organic nomenclature will prevail. For instance, when referencing substituted compounds or groups, references to substitution patterns are taken to indicate that the indicated group(s) is (are) located at the indicated position and that all other non-indicated positions are hydrogen. For example, reference to a 4-substituted phenyl group indicates that there is a non-hydrogen substituent located at the 4 position and hydrogens located at the 2, 3, 5, and 6 positions. By way of another example, reference to a 3-substituted naphth-2-yl indicates that there is a non-hydrogen substituent located at the 3 position and hydrogens located at the 1, 4, 5, 6, 7, and 8 positions. References to compounds or groups having substitutions at positions in addition to the indicated position will be referenced using comprising or some other alternative language. For example, a reference to a phenyl group comprising a substituent at the 4 position refers to a group having a non-hydrogen atom at the 4 position and hydrogen or any non-hydrogen group at the 2, 3, 5, and 6 positions.

Regarding claim transitional terms or phrases, the transitional term "comprising", which is synonymous with "including," "containing," "having," or "characterized by," is inclusive or open-ended and does not exclude additional, unrecited elements or method steps. The transitional phrase "consisting of" excludes any element, step, or ingredient not specified in the claim. The transitional phrase "consisting essentially of" limits the scope of a claim to the specified materials or steps and those that do not materially affect the basic and novel characteristic(s) of the claimed invention. The term "consisting essentially of" occupies a middle ground between closed terms like "consisting of" and fully open terms like "comprising." Absent an indication to the contrary, when describing a compound or composition "consisting essentially of" is not to be construed as "comprising," but is intended to describe the recited component that includes materials which do not significantly alter composition or method to which the term is applied. For example, a feedstock consisting essentially of a material A can include impurities typically present in a commercially produced or commercially available sample of the recited compound or composition. When a claim includes different features and/or feature classes (for example, a method step, feedstock features, and/or product features, among other possibilities), the transitional terms comprising, consisting essentially of, and consisting of apply only to feature class to which is utilized and it is possible to have different transitional terms or phrases utilized with different features within a claim. For example a method can comprise several recited steps (and other non-recited steps) but utilize a catalyst system preparation consisting of specific or alternatively consisting essentially of specific steps but utilize a catalyst system comprising recited components and other non-recited components.

While compositions and methods are described in terms of "comprising" (or other broad term) various components and/or steps, the compositions and methods can also described using narrower terms such as "consist essentially of" or "consist of" the various components and/or steps.

Use of the term "optionally" with respect to any element of a claim is intended to mean that the subject element is required, or alternatively, is not required. Both alternatives are intended to be within the scope of the claim.

The terms "a," "an," and "the" are intended, unless specifically indicated otherwise, to include plural alternatives, e.g., at least one. For any particular compound or group disclosed herein, any name or structure presented is intended to encompass all conformational isomers, regioisomers, and stereoisomers that can arise from a particular set of substituents, unless otherwise specified. For example, a general reference to pentane includes n-pentane, 2-methylbutane, and 2,2-dimethylpropane and a general reference to a butyl group includes an n-butyl group, a sec-butyl group, an iso-butyl group, and a t-butyl group or tert-butyl group. The name or structure also encompasses all enantiomers, diastereomers, and other optical isomers whether in enantiomeric or racemic forms, as well as mixtures of stereoisomers, as would be recognized by a skilled artisan, unless otherwise specified.

The term "olefin" whenever used in this specification and claims refers to hydrocarbons that have at least one carbon-carbon double bond that is not part of an aromatic ring or an aromatic ring system. The term "olefin" includes aliphatic and aromatic, cyclic and acyclic, and/or linear and branched hydrocarbons having at least one carbon-carbon double bond that is not part of an aromatic ring or ring system unless specifically stated otherwise. Olefins having only one, only two, only three, etc. . . . carbon-carbon double bonds can be identified by use of the term "mono," "di," "tri," etc. . . . within the name of the olefin. The olefins can be further identified by the position of the carbon-carbon double bond(s).

The term "alkene" whenever used in this specification and claims refers to a linear or branched aliphatic hydrocarbon olefin that has one or more carbon-carbon double bonds. Alkenes having only one, only two, only three, etc. . . . such multiple bonds can be identified by use of the term "mono," "di," "tri," etc. . . . within the name. For example, alkamonoenes, alkadienes, and alkatrienes refer to a linear or branched acyclic hydrocarbon olefins having only one carbon-carbon double bond (acyclic having a general formula of $C_nH_{2n}$), only two carbon-carbon double bonds (acyclic having a general formula of $C_nH_{2n-2}$), and only three carbon-carbon double bonds (acyclic having a general formula of $C_nH_{2n-4}$), respectively. Alkenes can be further identified by the position of the carbon-carbon double bond(s). Other identifiers can be utilized to indicate the presence or absence of particular groups within an alkene. For example, a haloalkene refers to an alkene having one or more hydrogen atoms replaced with a halogen atom.

The term "alpha olefin" as used in this specification and claims refers to an olefin that has a carbon-carbon double bond between the first and second carbon atom of the longest contiguous chain of carbon atoms. The term "alpha olefin" includes linear and branched alpha olefins unless expressly stated otherwise. In the case of branched alpha olefins, a branch can be at the 2-position (a vinylidene) and/or the 3-position or higher with respect to the olefin double bond. The term "vinylidene" whenever used in this specification and claims refers to an alpha olefin having a branch at the 2-position with respect to the olefin double bond. By itself, the term "alpha olefin" does not indicate the presence or absence of other carbon-carbon double bonds unless explicitly indicated.

The term "linear alpha olefin" as used herein refers to a linear olefin having a carbon-carbon double bond between the first and second carbon atom. The term "linear alpha olefin" by itself does not indicate the presence or absence of other carbon-carbon double bonds, unless explicitly indicated.

The term "normal alpha olefin" whenever used in this specification and claims refers to a linear aliphatic mono-olefin having a carbon-carbon double bond between the first and second carbon atom. It is noted that "normal alpha olefin" is not synonymous with "linear alpha olefin" as the term "linear alpha olefin" can include linear olefinic compounds having a double bond between the first and second carbon atoms and additional double bonds.

The term "consists essentially of normal alpha olefin(s)," or variations thereof, whenever used in this specification and claims refers to commercially available normal alpha olefin product(s). The commercially available normal alpha olefin product can contain non-normal alpha olefin impurities such as vinylidenes, internal olefins, branched alpha olefins, paraffins, and diolefins, among other impurities, which are not removed during the normal alpha olefin production process. One readily recognizes that the identity and quantity of the specific impurities present in the commercial normal alpha olefin product will depend upon the source of commercial normal alpha olefin product. Consequently, the term "consists essentially of normal alpha olefins" and its variants is not intended to limit the amount/quantity of the non-linear alpha olefin components any more stringently than the amounts/quantities present in a particular commercial normal alpha olefin product unless explicitly stated.

The term "1,2-disubstituted olefin" as used herein refers to a compound having at least one carbon-carbon double bond and having one and only one substituent located on each carbon atom of the carbon-carbon double bond(s). The term "trisubstituted olefin" as used herein refers to a compound having at least one carbon-carbon double bond where there are two substituents attached to one carbon of the olefin carbon-carbon double bond and one and only one substituent attached to the other carbon atom of the olefin carbon-carbon double bond.

As used within this specification, the phrases "in the substantial absence of an organic reaction medium," "in the absence of an organic reaction medium," "in the absence of an organic diluent," "in the substantial absence of an organic diluent," "in the absence of an organic solvent," "in the substantial absence of an organic solvent," and similar phrases refer to a step (e.g., forming the oligomer product) under conditions wherein the reactant concentration (e.g., monomer concentration) is not substantially reduced by non-reactive components. As will be apparent to one skilled in the art and with the help of this disclosure, the terms "organic medium," "organic diluent," and "organic solvent" refer to specific compound(s) that are introduced to reduce the concentration of the reactant(s) (e.g., monomer) or to serve specific function in the process, e.g., moderating the heat of reaction or providing fluidity to the reaction mixture, and do not function as a reactant within the oligomerization. Thus, the phrases "in the substantial absence of an organic reaction medium," "in the absence of an organic reaction medium," "in the absence of an organic diluent," "in the substantial absence of an organic diluent," "in the absence of an organic solvent," "in the substantial absence of an organic solvent," and similar phrases are not intended as limiting the invention to the complete absence of compounds that are impurities within the monomer or feed stream which under other circumstances or in greater quantities could be construed to act as a diluent or solvent. For example, while decane could be an "organic diluent" or "organic solvent" or "organic reaction medium" under certain circumstances, the presence of small or minor amounts (e.g., about ≤1.5 percent) of decane as an impurity in a 1-decene monomer stream does not substantially reduce the concentration of 1-decene or serve a specific function within the reaction system and thus would not be excluded by the use of the phrases "in the substantial absence of an organic reaction medium," "in the absence of an organic reaction medium," "in the absence of an organic diluent," "in the substantial absence of an organic diluent," "in the absence of an organic solvent," "in the substantial absence of an organic solvent," or similar phrases. If required the phrases "in the substantial absence of an organic reaction medium," "in the absence of an organic reaction medium," "in the absence of an organic diluent," "in the substantial absence of an organic diluent," "in the absence of an organic solvent," "in the substantial absence of an organic solvent," and similar phrases can be defined to mean ≤5 wt. %, ≤4 wt. %, ≤3 wt. %, ≤2.5 wt. %, ≤2 wt. %, ≤1.5 wt. %, ≤1 wt. %, ≤0.8 wt. %, ≤0.6 wt. %, or ≤0.5 wt. % of the organic reaction medium, organic diluent, or organic solvent.

The terms "room temperature" or "ambient temperature" are used herein to describe any temperature from 15° C. to 35° C. wherein no external heat or cooling source is directly applied to the reaction vessel. Accordingly, the terms "room temperature" and "ambient temperature" encompass the individual temperatures and any and all ranges, subranges, and combinations of subranges of temperatures from 15° C. to 35° C. wherein no external heating or cooling source is directly applied to the reaction vessel. The term "atmospheric pressure" is used herein to describe an earth air pressure wherein no external pressure modifying means is utilized. Generally, unless practiced at extreme earth altitudes, "atmospheric pressure" is about 1 atmosphere (alternatively, about 14.7 psi or about 101 kPa).

Features within this disclosure that are provided as a minimum values can be alternatively stated as "at least" or "greater than or equal to" any recited minimum value for the feature disclosed herein. Features within this disclosure that are provided as a maximum values can be alternatively stated as "less than or equal to" any recited maximum value for the feature disclosed herein.

Processes and/or methods described herein utilize steps, features, and compounds which are independently described herein. The process and methods described herein may or may not utilize step identifiers (e.g., 1), 2), etc., a), b), etc., or i), ii), etc.), features (e.g., 1), 2), etc., a), b), etc., or i), ii), etc.), and/or compound identifiers (e.g., first, second, etc.). However, it should be noted that processes and/or methods described herein can have multiple steps, features (e.g. reagent ratios, formation conditions, among other considerations), and/or multiple compounds having the same general descriptor. Consequently, it should be noted that the processes and/or methods described herein can be modified to use an appropriate step or feature identifier (e.g., 1), 2), etc., a), b), etc., or i), ii), etc.) and/or compound identifier (e.g., first, second, etc.) regardless of step, feature, and/or compound identifier utilized in the a particular aspect and/or embodiment described herein and that step or feature identifiers can be added and/or modified to indicate individual different steps/features/compounds utilized within the process and/or methods without detracting from the general disclosure.

Embodiments disclosed herein can provide the materials listed as suitable for satisfying a particular feature of the embodiment delimited by the term "or." For example, a particular feature of the disclosed subject matter can be disclosed as follows: Feature X can be A, B, or C. It is also contemplated that for each feature the statement can also be phrased as a listing of alternatives such that the statement "Feature X is A, alternatively B, or alternatively C" is also an embodiment of the present disclosure whether or not the statement is explicitly recited.

FIG. 1 illustrates an embodiment of the oligomerization of olefins using haloaluminate ionic liquids and the recovery of an oligomer product. In FIG. 1, a monomer or mixture of monomers in monomer stream 2, one or more halide components in halide component stream 4, and a haloaluminate ionic liquid in haloaluminate ionic liquid stream 6 combine to form a feed stream 8 which is introduced to a reaction zone 10. The monomer is oligomerized (e.g., by contacting the monomer, the haloaluminate ionic liquid, and the halide component) to form an oligomer product. The oligomer product is removed from the reaction zone 10 in a reaction zone effluent in stream 12. The reaction zone effluent comprising the oligomer product, unreacted monomer, and any residual haloaluminate ionic liquid (and any organic reaction medium, if utilized as discussed below) flows into a separator 20.

While FIG. 1 shows the monomer, the haloaluminate ionic liquid, and the halide component are together simultaneously contacted in the reaction zone 10 (e.g., the three components feed to reaction zone 10 together in feed stream 8), it is contemplated that embodiments of the disclosure include: i) the monomer and halide component can be contacted prior to contacting the monomer with the haloaluminate ionic liquid, ii) the halide component and the haloaluminate ionic liquid can be contacted prior to contacting the monomer with the haloaluminate ionic liquid, iii) the haloaluminate ionic liquid and the halide component can be separately and simultaneously contacted with the monomer, and iv) the monomer and the haloaluminate ionic liquid can be contacted prior to contacting the haloaluminate ionic liquid with the halide component.

While FIG. 1 shows the monomer, haloaluminate ionic liquid, and halide component are introduced in a single stream (e.g., feed stream 8) to the reaction zone 10, it is contemplated that embodiments of the disclosure include: i) the monomer and halide component can be introduced to the reaction zone 10 in a single stream separately (or simultaneously, or separately and simultaneously) with (or from) haloaluminate ionic liquid in haloaluminate ionic liquid stream 6, ii) the haloaluminate ionic liquid and halide component can be introduced to the reaction zone 10 in a single stream separately (or simultaneously, or separately and simultaneously) with (or from) monomer in monomer stream 2, iii) the monomer and haloaluminate ionic liquid can be introduced to the reaction zone 10 in a single stream separately (or simultaneously, or separately and simultaneously) with (or from) the halide component in halide component stream 4, and iv) the monomer in monomer stream 2, the halide component in halide component stream 4, and the haloaluminate ionic liquid in haloaluminate ionic liquid stream 6 can be introduced to the reaction zone 10 separately (or simultaneously, or separately and simultaneously).

In embodiments of the disclosure, the monomer, the halide component, and the haloaluminate ionic liquid can be periodically or continuously, and separately (or simultaneously, or simultaneously and separately) introduced to the reaction zone 10. Illustrative examples include: i) the monomer and halide component can be introduced to the reaction zone 10 in a single stream periodically or continuously, and separately (or simultaneously, or separately and simultaneously) with (or from) haloaluminate ionic liquid in haloaluminate ionic liquid stream 6, ii) the haloaluminate ionic liquid and optionally the halide component can be introduced to the reaction zone 10 in a single stream periodically or continuously, and separately (or simultaneously, or separately and simultaneously) with (or from) monomer in monomer stream 2, iii) the monomer and haloaluminate ionic liquid can be introduced to the reaction zone 10 in a single stream periodically or continuously, and separately (or simultaneously, or separately and simultaneously) with (or from) the halide component in halide component stream 4, and iv) the monomer in monomer stream 2, the halide component in halide component stream 4, and the haloaluminate ionic liquid in haloaluminate ionic liquid stream 6 can be introduced to the reaction zone 10 periodically or continuously, and separately (or simultaneously, or separately and simultaneously).

In embodiments of the disclosure, the monomer, the halide component, and the haloaluminate ionic liquid can be periodically or continuously introduced to the reaction zone 10 via one or more streams (e.g., streams 2, 4, 6, and 8 of FIG. 1), where the reaction zone 10 contains: i) the same or different monomer, ii) the same or different halide component, iii) the same or different haloaluminate ionic liquid, or iv) combinations thereof. For example, i) the monomer and optionally the halide component can be introduced in a single stream periodically or continuously, and separately (or simultaneously, or separately and simultaneously) with (or from) haloaluminate ionic liquid in haloaluminate ionic liquid stream 6 to the reaction zone 10 containing the same or different monomer, the same or different halide component, and the same or different haloaluminate ionic liquid, ii) the haloaluminate ionic liquid and optionally the halide component can be introduced in a single stream periodically or continuously, and separately (or simultaneously, or separately and simultaneously) with (or from) monomer in monomer stream 2 to the reaction zone 10 containing the same or different monomer, the same or different halide component, and the same or different haloaluminate ionic liquid, iii) the monomer and haloaluminate ionic liquid can be introduced in a single stream periodically or continuously, and separately (or simultaneously, or separately and simultaneously) with (or from) the halide component in halide component stream 4 to the reaction zone 10 containing the same or different monomer, the same or different halide component, and the same or different haloaluminate ionic liquid, and iv) the monomer in monomer stream 2, optionally the halide component in halide component stream 4, and the haloaluminate ionic liquid in haloaluminate ionic liquid stream 6 can be introduced periodically or continuously, and separately (or simultaneously, or separately and simultaneously) to the reaction zone 10 containing the same or different monomer, the same or different halide component, and the same or different haloaluminate ionic liquid.

The reaction zone 10 shown in FIG. 1 can comprise a continuous stirred tank reactor (CSTR), a plug flow reactor, or any combination thereof. Alternatively, the reaction zone 10 can comprise a plug flow reactor; or alternatively, a tubular reactor. In embodiments, the reaction zone 10 can comprise at least two reactors in series, in parallel, or any combination thereof.

The conditions capable of forming an oligomer product within the reaction zone 10 can be maintained to provide the dimerization, oligomerization, polymerization, or any combination thereof of the monomer to form the oligomer product. In an embodiment, the conditions capable of forming an oligomer product can comprise a temperature, a pressure, a time, or any combination thereof; alternatively, a temperature and a pressure; alternatively, a temperature and a time; or alternatively, a temperature, a pressure and a time.

Generally, the pressure which can be utilized as a condition capable of forming an oligomer product (e.g., the pressure of the reaction zone 10) can be any pressure which can facilitate the formation of the oligomer product. In an embodiment, the minimum pressure which can be utilized as a condition capable of forming the oligomer product can be 0 psig (0 kPa), or 0.1 psig (0.69 KPa). In an embodiment, the maximum pressure which can be utilized as a condition capable of forming the oligomer product can be 4,000 psig (27.6 MPa), 2,000 psig (13.8 MPa), 1,000 psig (6.9 MPa), 500 psig (3.4 MPa), 250 psig (1.7 MPa), or 150 psig (1.0 MPa). In an embodiment, the pressure which can be utilized as a condition capable of forming the oligomer product can range from any minimum pressure which can be utilized as a condition capable of forming the oligomer product to any maximum pressure which can be utilized as a condition capable of forming the oligomer product described herein. In some embodiments, suitable ranges for the pressure which can be utilized as a condition capable of forming the oligomer product can include, but are not limited to, from 0 psig (0 KPa) to 4,000 psig (27.6 MPa); alternatively, 0.1 psig (0.69 KPa) to 2,000 psig (13.8 MPa); alternatively, 0.1 psig (0.69 KPa) to 1,000 psig (6.9 MPa); alternatively, 0.1 psig (0.69 KPa) to 500 psig (3.4 MPa); alternatively, 0.1 psig (0.69 KPa) to 250 psig (1.7 MPa); or alternatively, 0.1 psig (0.69 KPa) to 150 psig (1.0 MPa). Other suitable pressure ranges which can be utilized as a condition capable of forming the oligomer product are readily apparent from the present disclosure.

In embodiments, the oligomer product can be formed at (e.g., the reaction zone 10 has) a pressure sufficient to maintain the reaction in a liquid state to 4,000 psig (27.6 MPa); alternatively, a pressure sufficient to maintain the reaction in a liquid state to 2,000 psig (13.8 MPa); alternatively, a pressure sufficient to maintain the reaction in a liquid state to 1,000 psig (6.9 MPa); alternatively, a pressure sufficient to maintain the reaction in a liquid state to 500 psig (3.4 MPa); alternatively, a pressure sufficient to maintain the reaction in a liquid state to 250 psig (1.7 MPa); or alternatively, a pressure sufficient to maintain the reaction in a liquid state to 150 psig (1.0 MPa).

Generally, the temperature which can be utilized as a condition capable of forming an oligomer product can be (e.g., the reaction zone 10 can have) any temperature which can facilitate the formation of the oligomer product. In an embodiment, the minimum temperature which can be utilized as a condition capable of forming the oligomer product can be 0° C., 5° C., 10° C., 15° C., 20° C., or 25° C. In an embodiment, the maximum temperature which can be utilized as a condition capable of forming the oligomer product can be 300° C., 250° C., 200° C., 170° C., 150° C., 135° C., or 125° C. In an embodiment, the temperature which can be utilized as a condition capable of forming the oligomer product can range from any minimum temperature which can be utilized as a condition capable of forming the oligomer product to any maximum temperature which can be utilized as a condition capable of forming the oligomer product described herein. In some embodiments, suitable ranges for the temperature which can be utilized as a condition capable of forming the oligomer product can include, but are not limited to, from 0° C. to 300° C.; alternatively, 5° C. to 250° C.; alternatively, 10° C. to 200° C.; alternatively, 15° C. to 170° C.; alternatively, 20° C. to 150° C.; alternatively, 20° C. to 135° C.; or alternatively, 25° C. to 125° C. Other suitable temperature ranges which can be utilized as a condition capable of forming the oligomer product are readily apparent from the present disclosure.

Generally, the time over which the oligomer product can be formed (e.g., the residence time of the monomer, halide component, haloaluminate ionic liquid, or any combination thereof in the reaction zone 10) as a condition capable of forming an oligomer product can be any time which can provide the monomer conversion and/or desired oligomer distribution. In relation to continuous processes, the time over which the oligomer product can be formed as a condition capable of forming an oligomer product can be the ratio of the reactor zone volume to the volumetric introduction rate of any of the feeds, (e.g., the monomer, the catalyst (or the catalyst mixture), and any other components (e.g., promoter, among other components described herein)) charged to or introduced into the reaction zone 10. The time is in units of time. It should be noted that in some situations the time can be the average amount of time (e.g., the average residence time) the particular materials (e.g., the monomer, the catalyst system, and/or the catalyst mixture), and any other components (e.g., promoter, among other components described herein), among others) spend within the reaction zone 10. The minimum time (or minimum average time) can be 1 minute, 2 minutes, 4 minutes, 6 minutes, 8 minutes, or 10 minutes. The maximum time (or average maximum time) can be 90 minutes, 2 hours, 4 hours, 6 hours, 8 hours, or 10 hours. In an embodiment, the time (or average time) which can be utilized as a condition capable of forming the oligomer product can range from any minimum time (or average minimum time) which can be utilized as a condition capable of forming the oligomer product to any maximum time (or average maximum time) which can be utilized as a condition capable of forming the oligomer product described herein. In some embodiments, the time (or average time) which can be utilized as a condition capable of forming the oligomer product can range, but is not limited to, from 1 minute to 10 hours; alternatively, from 2 minutes to 8 hours; alternatively, from 4 minutes to 6 hours; alternatively, from 6 minutes to 4 hours, alternatively, from 8 minutes to 2 hours; or alternatively, from 10 minutes to 90 minutes. Other suitable time ranges (or average time ranges) which can be utilized as a condition capable of forming the oligomer product are readily apparent from the present disclosure.

In embodiments, the oligomer product can be formed at a molar ratio of carbon-carbon double bonds of the monomer to aluminum in the haloaluminate ionic liquid of at least 1:1, 2:1, 5:1, 10:1, 15:1, 20:1, 30:1; 40:1 or 50:1; alternatively or additionally, a maximum molar ratio of carbon-carbon double bonds of the monomer to aluminum in the haloaluminate ionic liquid of 1000:1, 750:1, 500:1, 450:1, 400:1, 350:1, 300:1, or 250:1. In an embodiment, the molar ratio of carbon-carbon double bonds of the monomer to aluminum in the haloaluminate ionic liquid can range from any minimum molar ratio of carbon-carbon double bonds of the monomer to aluminum in the haloaluminate ionic liquid to any maximum molar ratio of carbon-carbon double bonds of the monomer to aluminum in the haloaluminate ionic liquid described herein. In some embodiments, suitable ranges for the molar ratio of carbon-carbon double bonds of the monomer to aluminum in the haloaluminate ionic liquid can include, but are not limited to, a molar ratio of carbon-carbon double bonds of the monomer to aluminum in the haloaluminate ionic liquid from 1:1 to 1000:1, from 2:1 to 750:1, from 5:1 to 1000:1, from 5:1 to 500:1, from 10:1 to 1000:1, from 10:1 to 750:1 from 10:1 to 500:1, from 10:1 to 400:1, from 15:1 to 1000:1 from 15:1 to 750:1 from 15:1 to 500:1, from 15:1 to 400:1, from 20:1 to 500:1, from 20:1 to 400:1, from 20:1 to 300:1, from 30:1 to 500:1, from 30:1 to 400:1 or from 30:1 to 300:1. Other suitable molar ratios of carbon-carbon double bonds of the monomer to aluminum in the haloaluminate ionic liquid which can be utilized are readily apparent from the present disclosure. The molar ratio of carbon-carbon double bonds of the monomer to aluminum in the haloaluminate ionic liquid can be referred to as the carbon-carbon double bonds of the monomer to aluminum in the haloaluminate ionic liquid molar ratio.

In embodiments, the oligomer product can be formed at a molar ratio of halide in the halide component to aluminum in the haloaluminate ionic liquid of at least 0.0001:1, 0.001:1, 0.005:1, 0.01:1, 0.025:1, 0.05:1, 0.075:1, 0.1:1, 0.14:1, 0.18:1, or 0.2:1; alternatively or additionally, a maximum molar ratio of halide in the halide component to aluminum in the haloaluminate ionic liquid of 10:1, 7.5, 5:1, 4:1, 3:1, 2:1, 1.75:1, or 1.5:1. In an embodiment, the molar ratio of halide in the halide component to aluminum in the haloaluminate ionic liquid can range from any minimum molar ratio of halide in the halide component to aluminum in the haloaluminate ionic liquid to any maximum molar ratio of halide in the halide component to aluminum in the haloaluminate ionic liquid described herein. In some embodiments, suitable ranges for the molar ratio of halide in the halide component to aluminum in the haloaluminate ionic liquid can include, but are not limited to, a molar ratio of halide in the halide component to aluminum in the haloaluminate ionic liquid from 0.0001:1 to 10:1, from 0.001:1 to 7.5:1, from 0.01:1 to 5:1, from 0.025:1 to 5:1, from 0.05:1 to 5:1, from 0.05:1 to 5:1, from 0.1:1 to 5:1, from 0.1:1 to 4:1, from 0.1:1 to 3:1, from 0.12:1 to 4:1, from 0.14:1 to 5:1, from 0.14:1 to 4:1, from 0.14:1 to 3:1, from 0.14:1 to 2:1, from 0.16:1 to 4:1, from 0.16:1 to 3:1, from 0.16:1 to 2:1, from 0.18:1 to 4:1, from 0.18:1 to 3:1, from 0.18:1 to 2:1, from 0.2:1 to 4:1, from 0.2:1 to 3:1, or from 0.2:1 to 2:1. Other suitable molar ratios of halide in the halide component to aluminum in the haloaluminate ionic liquid which can be utilized are readily apparent from the present disclosure. The molar ratio of halide in the halide component to aluminum in the haloaluminate ionic liquid can be referred to as the halide in the halide component to aluminum in the haloaluminate ionic liquid molar ratio.

In an embodiment, the monomer can comprise, or consist essentially of, one or more olefins (linear or branched, cyclic or acyclic, aliphatic or non-aliphatic), one or more alpha olefins (linear or branched, cyclic or acyclic, aliphatic or non-aliphatic), one or more normal alpha olefins, or one or more internal olefins (linear or branched, cyclic or acyclic, aliphatic or non-aliphatic), or any combination thereof. In some embodiments, the monomer (olefin, alpha olefin, normal alpha olefin, or internal olefin) can be a hydrocarbon olefin. In other embodiments, the monomer (olefin, alpha olefin, normal alpha olefin, or internal olefin) can be an aliphatic olefin. In an embodiment, the monomer can comprise, or consist essentially of, one or more normal alpha olefins. In another embodiment, the alpha olefin (or the normal alpha olefin) which can be utilized as the monomer can comprise, consist essentially of, or can be, one or more normal alpha olefins.

A wide range of monomer carbon numbers can be utilized in the process. In any aspect and/or in any embodiment described herein, the monomer can comprise, or consist essentially of, or can be, a $C_6$ to $C_{20}$ olefin; alternatively, a $C_6$ to $C_{18}$ olefin; alternatively, a $C_6$ to $C_{14}$ olefin; or alternatively, a $C_8$ to $C_{12}$ olefin. In any aspect and/or in any embodiment described herein, the monomer can comprise, or consist essentially of, or can be, a $C_6$ to $C_{20}$ alpha olefin; alternatively, a $C_6$ to $C_{18}$ alpha olefin; alternatively, a $C_6$ to $C_{14}$ alpha olefin; or alternatively, a $C_8$ to $C_{12}$ alpha olefin. In an embodiment, the monomer can comprise, or consist essentially of, or can be, a $C_6$ alpha olefin, a $C_8$ alpha olefin, a $C_{10}$ alpha olefin, a $C_{12}$ alpha olefin, a $C_{14}$ alpha olefin, a $C_{16}$ alpha olefin, a $C_{18}$ alpha olefin, a $C_{20}$ alpha olefin, or any combination thereof; alternatively, a $C_6$ alpha olefin, a $C_8$ alpha olefin, a $C_{10}$ alpha olefin, a $C_{12}$ alpha olefin, a $C_{14}$ alpha olefin, a $C_{16}$ alpha olefin, a $C_{18}$ alpha olefin, or any combination thereof; alternatively, a $C_6$ alpha olefin, a $C_8$ alpha olefin, a $C_{10}$ alpha olefin, a $C_{12}$ alpha olefin, a $C_{14}$ alpha olefin, or any combination thereof; alternatively, a $C_8$ alpha olefin, a $C_{10}$ alpha olefin, a $C_{12}$ alpha olefin, or any combination thereof; alternatively, a $C_6$ alpha olefin; alternatively, a $C_8$ alpha olefin; alternatively, a $C_{10}$ alpha olefin; alternatively, a $C_{12}$ alpha olefin; alternatively, a $C_{14}$ alpha olefin; alternatively, a $C_{16}$ alpha olefin; or alternatively, a $C_{18}$ alpha olefin.

In any aspect and/or in any embodiment described herein, the monomer can comprise, or consist essentially of, or can be, a $C_6$ to $C_{20}$ normal alpha olefin; alternatively, a $C_6$ to $C_{18}$ normal alpha olefin; alternatively, a $C_6$ to $C_{14}$ normal alpha olefin; or alternatively, a $C_8$ to $C_{12}$ normal alpha olefin. In an embodiment, the monomer can comprise, or consist essentially of, or can be, a $C_6$ normal alpha olefin, a $C_8$ normal alpha olefin, a $C_{10}$ normal alpha olefin, a $C_{12}$ normal alpha olefin, a $C_{14}$ normal alpha olefin, a $C_{16}$ normal alpha olefin, a $C_{18}$ normal alpha olefin, a $C_{20}$ normal alpha olefin, or any combination thereof; alternatively, a $C_6$ normal alpha olefin, a $C_8$ normal alpha olefin, a $C_{10}$ normal alpha olefin, a $C_{12}$ normal alpha olefin, a $C_{14}$ normal alpha olefin, a $C_{16}$ normal alpha olefin, a $C_{18}$ normal alpha olefin, or any combination thereof; alternatively, a $C_6$ normal alpha olefin, a $C_8$ normal alpha olefin, a $C_{10}$ normal alpha olefin, a $C_{12}$ normal alpha olefin, a $C_{14}$ normal alpha olefin, or any combination thereof; alternatively, a $C_8$ normal alpha olefin, a $C_{10}$ normal alpha olefin, a $C_{12}$ normal alpha olefin, or any combination thereof; alternatively, a $C_6$ normal alpha olefin; alternatively, a $C_8$ normal alpha olefin; alternatively, a $C_{10}$ normal alpha olefin; alternatively, a $C_{12}$ normal alpha olefin; alternatively, a $C_{14}$ normal alpha olefin; alternatively, a $C_{16}$ normal alpha olefin; or alternatively, a $C_{18}$ normal alpha olefin.

In any aspect and/or in any embodiment described herein, the monomer can comprise, or consist essentially of, or can be 1-hexene, 1-octene, 1-decene, 1-dodecene, 1-tetradecene, 1-hexadecene, 1-octadecene, 1-eicocene, or any combination thereof; alternatively, 1-hexene, 1-octene, 1-decene, 1-dodecene, 1-tetradecene, 1-hexadecene, 1-octadecene, or any combination thereof; alternatively, 1-hexene, 1-octene, 1-decene, 1-dodecene, 1-tetradecene, or any combination thereof; alternatively, 1-octene, 1-decene, 1-dodecene, or any combination thereof. In other embodiments, the monomer can comprise, or consist essentially of, 1-hexene; alternatively, 1-heptene; alternatively, 1-octene; alternatively, 1-nonene; alternatively, 1-decene; alternatively, 1-undecene; alternatively, 1-dodecene; alternatively, 1-tridecene; alternatively, 1-tetradecene; alternatively, 1-pentadecene; alternatively, 1-hexadecene; alternatively, 1-heptadecene; or alternatively, 1-octadecene.

In any aspect and/or embodiment described herein, the monomer can comprise, at least 50 wt. % of any olefin described herein (e.g., alpha olefin or normal alpha olefin, among others described herein). Alternatively, the monomer can comprise at least 55 wt. %, 60 wt. %, 65 wt. %, 70 wt. %, 75 wt. %, 80 wt. %, 82.5 wt. %, 85 wt. %, 87.5 wt. %, 90 wt. %, 91 wt. %, 92 wt. %, 93 wt. %, 94 wt. %, 95 wt. %, 96 wt. %, 97 wt. %, or 98 wt. % of any olefin described herein (e.g., alpha olefin or normal alpha olefin, among others described herein). The wt. % of the components of the monomer is based upon the total weight of the monomer.

In embodiments, the monomer can comprise at least 50 mol %, 70 mol %, 75 mol %, 80 mol %, 85 mol %, 90 mol %, or 95 mol % of any olefin described herein (e.g., alpha olefin or normal alpha olefin, among others described herein). In embodiments, the olefin can comprise at least 50 mol %, 70 mol %, 75 mol %, 80 mol %, 85 mol %, 90 mol %, or 95 mol % alpha olefin; alternatively, normal alpha olefin. In embodiments, the monomer can comprise at least 75 mol %, 80 mol %, 82.5 mol %, 85 mol %, 87.5 mol %, 90 mol %, 91 mol %, 92 mol %, 93 mol %, 94 mol %, or 95 mol % 1-octene; alternatively, 1-decene; alternatively, 1-dodecene; alternatively, a mixture of octene and decene; alternatively, a mixture of 1-decene and 1-dodecene; or alternatively, a mixture of 1-octene, 1-decene, and 1-dodecene. In an embodiment, the monomer can comprise at least 75 mol % $C_6$ to $C_{20}$ olefin. In another embodiment, the monomer can comprise at least 90 mol % $C_6$ to $C_{12}$ normal alpha olefin. The mol % of the components of the monomer is based on total moles of the monomer.

In any aspect and/or embodiment described herein, the monomer can comprise a mixture of any olefins described herein (e.g., alpha olefin or normal alpha olefin, among others described herein) having different gram molecular weights (or carbon numbers). In some embodiments, the monomer comprising a mixture of olefins having different gram molecular weights (or carbon numbers) can comprise a mixture of 2, 3, 4, 5 or 6 olefins having different gram molecular weights (or carbon numbers); alternatively, 2, 3, or 4 olefins having different gram molecular weights (or carbon numbers); alternatively, 2 or 3 olefins having different gram molecular weights (or carbon numbers); alternatively, 2 olefins having different gram molecular weights (or carbon numbers); alternatively, 3 olefins having different gram molecular weights (or carbon numbers); alternatively, 4 olefins having different gram molecular weights (or carbon numbers); alternatively, 5 olefins having different gram molecular weights (or carbon numbers); or alternatively, 6 olefins having different gram molecular weights (or carbon numbers). In some embodiments, the monomer comprising any mixture of olefins having different gram molecular weights described herein can have an average gram molecular weight from 84 g/mol to 252 g/mol, from 112 g/mol to 224 g/mol, 112 g/mol to 196 g/mol; alternatively, from 126 g/mol to 168 g/mol; alternatively, 133 g/mole to 161 g/mole. In some embodiments, the monomer comprising any mixture of olefins having different carbons number described herein can have an average carbon number from 6 carbon atoms to 18 carbon atoms, 8 carbon atoms to 16 carbon atoms, 8 carbon atoms to 14 carbon atoms; alternatively, from 9 carbon atoms to 12 carbon atoms; alternatively, 9.5 carbon atoms to 11.5 carbon atoms. The average number of carbons atoms is defined as the total sum of the mole fraction of each olefin carbon number times the carbon number of the olefin ($Cav=\Sigma[(\text{mole fraction})_i (\text{number of carbons})_i]$). In embodiments, the monomer can comprise a mixture of any two or more of 1-octene, 1-decene, and 1-dodecene. The mixture can comprise at least 90, 92, 93, 94, or 95 mol % of any two of more 1-octene, 1-decene, and 1-dodecene.

Generally, any of the embodiments described herein can be operated to convert any desired quantity of the monomer to an oligomer product and/or produce an oligomer product having any desired oligomer distribution. In an embodiment, at least 60 wt. %, 70 wt. %, 75 wt. %, 80 wt. %, 85 wt. %, or 90 wt. % of the monomer can be converted to an oligomer product.

In an embodiment, the monomer can comprise, consist essentially of, or can be, any normal alpha olefin or mixture of alpha olefin described herein. Generally, the normal alpha olefin which can be utilized can be produced by any process which can produce a normal alpha olefin having the purity acceptable for the herein described processes. One readily available source of a normal alpha olefin monomer applicable to the herein described process includes without limitation the products from the oligomerization of ethylene. Commercially available normal alpha olefins produced by ethylene oligomerization are available from Chevron Phillips Chemical Company, LP, Shell, Ineos, Mitsubishi, and Idemitsu among other sources. Depending upon the particular process and alpha carbon number, the normal alpha olefin content of the commercial normal alpha olefin feedstocks can vary. However, all are generally usable within the process disclosed herein.

In an embodiment the oligomer product can be formed in the presence of (e.g., the reaction zone 10 contains) less than 10 mol %, 9 mol %, 8 mol %, 7 mol %, 6 mol %, 5 mol %, 4 mol %, 3 mol %, 2 mol %, 1 mol % isoparaffins. Generally, the amount of isoparaffins in which the oligomer product can be formed is based upon the moles of monomer.

The use of a haloaluminate ionic liquid in combinations with one or more halide components can be referred to herein as a "catalyst system." FIG. 1 illustrates use of a catalyst system comprising 1) a haloaluminate ionic liquid (e.g., flowing in stream 6), and 2) a halide component (e.g., flowing in stream 4).

The halide component can be referred to as a co-catalyst, a promoter, modifier, or activator.

In embodiments, the halide component can be a Brönsted acid or an organohalide. In embodiments, the halide component can be a hydrogen halide; alternatively, the halide component can be hydrogen chloride, hydrogen bromide, or any combination thereof; alternatively, hydrogen chloride; or alternatively, hydrogen bromide. In embodiments, the halide component can be a $C_1$ to $C_{12}$ organohalide; alternatively, a $C_2$ to $C_{12}$ organohalide; alternatively, a $C_3$ to $C_{12}$ organohalide; alternatively, a $C_1$ to $C_{12}$ alkyl halide; alternatively, a $C_2$ to $C_{12}$ alkyl halide; or alternatively, a $C_3$ to $C_{12}$ alkyl halide.

In embodiments, the halide component can be a propyl halide, a butyl halide, a pentyl halide, a hexyl halide, a heptyl halide, an octyl halide, a nonyl halide, a decyl halide, or any combination thereof. In an embodiment, the halide component can be a propyl chloride, a butyl chloride, a pentyl chloride, a hexyl chloride, a heptyl chloride, an octyl chloride, a nonyl chloride, a decyl chloride, or any combination thereof. In some embodiments, the halide component can be a propyl bromide, a butyl bromide, a pentyl bromide, a hexyl bromide, a heptyl bromide, an octyl bromide, a nonyl bromide, a decyl bromide, or any combination thereof.

In embodiments, the organohalide can be a primary organohalide (or a primary alkyl halide), a secondary organohalide (or a secondary alkyl halide), a tertiary organohalide (or a tertiary alkyl halide), or any combination thereof; alternatively, a secondary organohalide (or a secondary alkyl halide), a tertiary organohalide (or a tertiary alkyl halide), or any combination thereof; alternatively, a primary organohalide (or a primary alkyl halide); alternatively, a secondary organohalide (or a secondary alkyl halide); or alternatively, a tertiary organohalide (or a tertiary alkyl halide). In embodiments, the organohalide (or an alkyl halide) can be an organo chloride (or an alkyl halide), an organo bromide (or an alkyl bromide), an organo iodide (or an alkyl iodide), or any combination thereof; alternatively, an organo chloride (or an alkyl halide); alternatively, an organo bromide (or an alkyl bromide); or alternatively, an organo iodide (or an alkyl iodide).

Ionic liquids are a category of compounds which are made up entirely of ions and are generally liquids at or below process temperatures. Often salts which are composed entirely of ions are solids with high melting points, for example, above 450° C. These solids are commonly known as 'molten salts' when heated to above their melting points. Sodium chloride, for example, is a common 'molten salt', with a melting point of 800° C. Ionic liquids differ from 'molten salts', in that they have low melting points, for example, from −100° C. to 200° C. Ionic liquids tend to be liquids over a very wide temperature range, with some having a liquid range of up to 300° C. or higher. Ionic liquids are generally non-volatile, with effectively no vapor pressure. Many are air and water stable, and can be good solvents for a wide variety of inorganic, organic, and polymeric materials.

The properties of ionic liquids can be tailored by varying the cation and anion pairing. Ionic liquids and some of their commercial applications are described, for example, in J. Chem. Tech. Biotechnol, 1997, vol. 68(4), pp. 351-356; J. Phys. Condensed Matter, 5:(supp 34B):B99-B106 (1993); Chemical and Engineering News, Mar. 30, 1998, pp. 32-37; J. Mater. Chem., 1998, vol. 8, pp. 2627-2636; and Chem. Rev., 1999, vol. 99, pp. 2071-2084.

Many ionic liquids are amine-based. Among the most common ionic liquids are those formed by reacting a nitrogen-containing heterocyclic ring (cyclic amines), preferably nitrogen-containing aromatic rings (aromatic amines), with an alkylating agent (for example, an alkyl halide) to form a quaternary ammonium salt, followed by ion exchange or other suitable reactions to introduce the appropriate counter anionic species to form ionic liquids. Examples of suitable heteroaromatic rings include pyridine and its derivatives, imidazole and its derivatives, and pyrrole and its derivatives. These rings can be alkylated with varying alkylating agents to incorporate a broad range of alkyl groups on the nitrogen including straight, branched or cyclic $C_{1-20}$ alkyl group. Frequently, $C_{1-12}$ alkyl groups are used since alkyl groups larger than $C_{12}$ can produce undesirable solid products with some amines. Pyridinium and imidazolium-based ionic liquids are perhaps the most commonly used ionic liquids. Other amine-based ionic liquids including cyclic and non-cyclic quaternary ammonium salts are frequently used. Phosphonium and sulphonium-based ionic liquids have also been used.

Counter anions which have been used in ionic liquids include chloroaluminate, bromoaluminate, gallium chloride, tetrafluoroborate, tetrachloroborate, hexafluorophosphate, nitrate, trifluoromethane sulfonate, methylsulfonate, p-toluenesulfonate, hexafluoroantimonate, hexafluoroarsenate, tetrachloroaluminate, tetrabromoaluminate, perchlorate, hydroxide anion, copper dichloride anion, iron trichloride anion, antimony hexafluoride, copper dichloride anion, zinc trichloride anion, as well as various lanthanum, potassium, lithium, nickel, cobalt, manganese, and other metal ions. The ionic liquids which can be used advantageous in the present disclosure include acidic haloaluminates; alternatively, chloroaluminates, bromoaluminates, or a combination thereof; alternatively, chloroaluminates; or alternatively, bromoaluminates.

In embodiments, the haloaluminate ionic liquid can be a trialkylammonium haloaluminate ionic liquid, a tetraalkylammonium haloaluminate ionic liquid, hydrogen pyridinium haloaluminate ionic liquid, an N-alkylpyridinium haloaluminate ionic liquid, an N,N'-dialkylimidizolium haloaluminate ionic liquid, or any combination thereof; alternatively, a tetraalkylammonium haloaluminate ionic liquid, an N-alkylpyridinium haloaluminate ionic liquid, an N,N'-dialkylimidizolium haloaluminate ionic liquid, or any combination thereof; alternatively, a tetraalkylammonium haloaluminate ionic liquid; alternatively, an N-alkylpyridinium haloaluminate ionic liquid; or alternatively, an N,N'-dialkylimidizolium haloaluminate ionic liquid.

In embodiments, the haloaluminate ionic liquid can be a chloroaluminate ionic liquid, a bromoaluminate ionic liquid, or any combination thereof; alternatively, a chloroaluminate ionic liquid; or alternatively, a bromoaluminate ionic liquid.

In embodiments, the haloaluminate ionic liquid can be N-(n-butyl)pyridinium chloroaluminate, N-(n-butyl)pyridinium bromoaluminate, or any combination thereof; alternatively, N-(n-butyl)pyridinium bromoaluminate; or alternatively, N-(n-butyl)pyridinium chloroaluminate.

In embodiments, the haloaluminate ionic liquid can have a cationic portion comprising trialkylammonium, tetraalkylammonium, N-alkylpyridinium, or N',N"-dialkylimidizolium; alternatively, tetraalkylammonium, N-alkylpyridinium, or N',N"-dialkylimidizolium; alternatively, trialkyl ammonium; alternatively, tetraalkylammonium; alternatively, N-alkylpyridinium; or alternatively, N',N"-dialkylimidizolium. In embodiments where the cationic portion is trialkylammonium, the cationic portion can have Structure ILC 1. In embodiments where the cationic portion is tetraalkylammonium, the cationic portion can have Structure ILC 2. In embodiments where the cationic portion is N-alkylpyridinium, the cationic portion can have Structure ILC 3 or Structure ILC 4; alternatively, Structure ILC 3; or alternatively, Structure ILC 4. In embodiments where the cationic portion is N',N"-dialkylimidizolium, the cationic portion can have Structure ILC 5 or Structure ILC 6; alternatively, Structure ILC 5; or alternatively, Structure ILC 6.

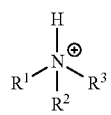

ILC 1

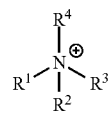

ILC 2

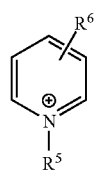

ILC 3

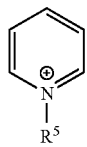

ILC 4

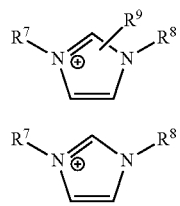

ILC 5

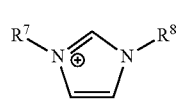

ILC 6

Each $R^1$, $R^2$, and $R^3$ of the trialkylammonium having Structure ILC 1, each $R^1$, $R^2$, $R^3$, and $R^4$ of the tetraalkylammonium having Structure ILC 2, each $R^5$ and $R^6$ of the N-alkylpyridinium having Structure ILC 3, each $R^5$ of the N-alkylpyridinium having Structure ILC 4, each $R^7$, $R^8$, and $R^9$ of the N',N"-dialkylimidizolium having Structure ILC 5, or each $R^7$ and $R^8$ of the N',N"-dialkylimidizolium having Structure ILC 6 independently can be a hydrocarbyl group.

In some embodiments, each hydrocarbyl group which can be utilized as $R^1$, $R^2$, and $R^3$ of the trialkylammonium having Structure ILC 1, as $R^1$, $R^2$, $R^3$, and $R^4$ of the tetraalkylammonium having Structure ILC 2, as $R^5$ and $R^6$ of the N-alkylpyridinium having Structure ILC 3, as $R^5$ of the N-alkylpyridinium having Structure ILC 4, as $R^7$, $R^8$, and $R^9$ of the N',N"-dialkylimidizolium having Structure ILC 5, or $R^7$ and $R^8$ of the N',N"-dialkylimidizolium having Structure ILC 6 independently can be an alkyl group, a phenyl group, or an alkyl substituted phenyl group; alternatively, a phenyl group or an alkyl substituted phenyl group; alternatively, an alkyl group; alternatively, a phenyl group; or alternatively, an alkyl substituted phenyl group.

In embodiments, each hydrocarbyl group which can be utilized as $R^1$, $R^2$, and $R^3$ of the trialkylammonium having Structure ILC 1, as $R^1$, $R^2$, $R^3$, and $R^4$ of the tetraalkylammonium having Structure ILC 2, as $R^5$ and $R^6$ of the N-alkylpyridinium having Structure ILC 3, as $R^5$ of the N-alkylpyridinium having Structure ILC 4, as $R^7$, $R^8$, and $R^9$ of the N',N"-dialkylimidizolium having Structure ILC 5, or $R^7$ and $R^8$ of the N',N"-dialkylimidizolium having Structure ILC 6 independently can be a $C_1$ to $C_{20}$ hydrocarbyl group; alternatively, a $C_1$ to $C_{15}$ hydrocarbyl group; alternatively, a $C_1$ to $C_{10}$ hydrocarbyl group; alternatively, a $C_1$ to $C_5$ hydrocarbyl group; alternatively, a phenyl group; alternatively, a $C_7$ to $C_{20}$ alkyl substituted phenyl group; alternatively, a $C_7$ to $C_{15}$ alkyl substituted phenyl group; or alternatively, a $C_7$ to $C_{10}$ alkyl substituted group; alternatively, a $C_1$ to $C_{20}$ alkyl group; alternatively, a $C_1$ to $C_{15}$ alkyl group; or alternatively, a $C_1$ to $C_{10}$ alkyl group; or alternatively, a $C_1$ to $C_5$ alkyl group.

Each alkyl group which can be utilized as $R^1$, $R^2$, and $R^3$ of the trialkyl ammonium having Structure ILC 1, as $R^1$, $R^2$, $R^3$, and $R^4$ of the trialkylammonium having Structure ILC 2, as $R^5$ and $R^6$ of the N-alkylpyridinium having Structure ILC 3, as $R^5$ of the N-alkylpyridinium having Structure ILC 4, as $R^7$, $R^8$, and $R^9$ of the N',N"-dialkylimidizolium having Structure ILC 5, as $R^7$ and $R^8$ of the N',N"-dialkylimidizolium having Structure ILC 6, or the alkyl substituent(s) for the alkyl substituted phenyl groups independently can be a methyl group, a ethyl group, a propyl group, a butyl group, a pentyl group, or a hexyl group; alternatively a methyl group, an ethyl group, an n-propyl group, an isopropyl group, an n-butyl group, a sec-butyl group, an isobutyl group, a tert-butyl group, an n-pentyl group, a 2-pentyl group, a 3-pentyl group, a 2-methyl-1-butyl group, a tert-pentyl group, a 3-methyl-1-butyl group, a 3-methyl-2-butyl group, or a neo-pentyl group; alternatively, a methyl group, an ethyl group, an isopropyl group, a tert-butyl group, or a neo-pentyl group; alternatively, a methyl group; alternatively, an ethyl group; alternatively, an isopropyl group; alternatively, a tert-butyl group; or alternatively, a neo-pentyl group.

As discussed above, the embodiments described herein can be operated to produce an oligomer product. In embodiments, the oligomer product can generally comprise dimers, trimers, and/or higher oligomers. In embodiments, the oligomer product can comprise i) at least 75 wt. %, 80 wt. %, 85 wt. %, 90 wt. %, or 95 wt. % dimers, trimers, tetramers, pentamers, hexamers, heptamers, octamers, nonamers, and/or decamers; ii) at least 50 wt. %, 55 wt. %, 60 wt. %, 65 wt. %, 70 wt. %, 80 wt. %, 85 wt. %, or 90 wt. % trimers, tetramers, pentamers, hexamers, heptamers, octamers, nonamers, and/or decamers; iii) at least 75 wt. %, 80 wt. %, 85 wt. %, 90 wt. %, or 95 wt. % dimers, trimers, tetramers, pentamers, hexamers, and/or heptamers; iv) at least 50 wt. %, 55 wt. %, 60 wt. %, 65 wt. %, 70 wt. %, 80 wt. %, 85 wt. %, or 90 wt. % trimers, tetramers, pentamers, hexamers, and/or heptamers; v) at least 30 wt. %, 35 wt. %, 40 wt. %, 45 wt. %, 50 wt. %, 55 wt. %, or 60 wt. % dimers trimers, tetramers, and/or pentamers; vi) at least 25 wt. %, 30 wt. %, 35 wt. %, 40 wt. %, 45 wt. %, or 50 wt. % trimers, tetramers, and/or pentamers; vii) at least 25 wt. %, 30 wt. %, 35 wt. %, 40 wt. %, 45 wt. %, 50 wt. %, 55 wt. %, or 60 wt. % dimers, trimers, and/or tetramers; viii) at least 20 wt. %, 25 wt. %, 30 wt. %, 35 wt. %, 40 wt. %, 45 wt. %, or 50 wt. % trimers and/or tetramers; or ix) any combination thereof.

In additional or alternative embodiments, the oligomer product can comprise a total of at least 50 wt. %, 60 wt. %, 70 wt. %, 75 wt. %, 80 wt. %, 85 wt. %, or 90 wt. % dimer, trimer, tetramer and pentamer; alternatively or additionally, a maximum total of 100 wt. %, 98 wt. %, 96 wt. %, 95 wt. %, or 94 wt. % dimer, trimer, tetramer and pentamer. In some embodiments, the oligomer product can comprise a total of from 50 wt. % to 100 wt. %, from 60 wt. % to 98 wt. %, from 70 wt. % to 98 wt. %, from 70 wt. % to 95 wt. %, from 75 wt. % to 96 wt. %, from 80 wt. % to 96 wt. %, or from 85 wt. % to 96 wt. % dimer, trimer, tetramer, and pentamer.

In additional or alternative embodiments, the oligomer product can comprise a total of at least 35 wt. %, 45 wt. %, 45 wt. %, 50 wt. %, 55 wt. %, 60 wt. %, or 65 wt. % trimer, tetramer and pentamer; alternatively or additionally, a maximum total of 100 wt. %, 95 wt. %, 90 wt. %, or 85 wt. % trimer, tetramer and pentamer. In some embodiments, the oligomer product can comprise a total of from 35 wt. % to 100 wt. %, from 40 wt. % to 95 wt. %, from 45 wt. % to 90 wt. %, from 40 wt. % to 85 wt. %, from 50 wt. % to 90 wt. %, or from 50 wt. % to 85 wt. %, trimer, tetramer and pentamer.

In additional or alternative embodiments, the oligomer product can comprises a total of at least 30 wt. %, 35 wt. %, 40 wt. %, 45 wt. %, or 50 wt. % trimer and tetramer; alternatively or additionally, a maximum total of 90 wt. %, or 85 wt. %, 80 wt. %, or 75 wt. % trimer and tetramer. In some embodiments, the oligomer product can comprise a total of from 30 wt. % to 90 wt. %, from 40 wt. % to 95 wt. %, from 40 wt. % to 90 wt. %, from 40 wt. % to 85 wt. %, from 45 wt. % to 90 wt. %, from 45 wt. % to 85 wt. %, or from 45 wt. % to 80 wt. % trimer and tetramer.

In embodiments, the oligomer product can comprise less than 40 wt. %, 30 wt. %, 25 wt. %, 20 wt. %, 18 wt. %, 16 wt. %, 14 wt. %, 12 wt. %, or 10 wt. % dimer. Additionally or alternatively, the oligomer product can comprise less than 30 wt. %, 25 wt. %, 20 wt. %, 15 wt. %, 10 wt. %, 8 wt. %, 6 wt. %, 5 wt. %, 4 wt. %, 3 wt. %, or 2 wt. % oligomer containing 7 or more monomer units.

The oligomer product can have a minimum average molecular weight (Mn) of at least 375 g/mole, 400 g/mol, 425 g/mol, 450 g/mol, 475 g/mol, or 500 g/mol; additionally or alternatively, a maximum average molecular weight (Mn) of 850 g/mol, 825 g/mol, 800 g/mol, 775 g/mol, 750 g/mol, 725 g/mol, 700 g/mol, 675 g/mol, or 650 g/mol. In an embodiment, the average molecular weight (Mn) of the oligomer product can range from any minimum average molecular weight (Mn) to any maximum average molecular weight (Mn) described herein. In some embodiments, suitable ranges for the average molecular weight (Mn) can include, but are not limited to, an average molecular weight (Mn) ranging from 375 g/mol to 850 g/mol, from 400 g/mol to 800 g/mol, from 425 g/mol to 750 g/mol, from 425 g/mol to 700 g/mol, from 450 g/mol to 700 g/mol, from 450 g/mol to 675 g/mol, or from 450 g/mol to 650 g/mol. Other suitable average molecular weight (Mn) ranges are readily apparent from the present disclosure.

In embodiments, the oligomer product can comprise at least 50 wt. %, 60 wt. %, 70 wt. %, 75 wt. %, 80 wt. %, 85 wt. %, 90 wt. %, or 95 wt. % $C_{18}$ to $C_{64}$ oligomers. In other embodiments, the oligomer product can comprise at least 50 wt. %, 60 wt. %, 70 wt. %, 75 wt. %, 80 wt. %, 85 wt. %, or 90 wt. % $C_{18}$ to $C_{54}$ oligomers. Alternatively or additionally, the oligomer product can comprise a maximum of 100 wt. %, 98 wt. %, 96 wt. %, 95 wt. %, or 94 wt. % $C_{18}$ to $C_{54}$ oligomers. In other embodiments, the oligomer product can comprise from 50 wt. % to 100 wt. %, from 60 wt. % to 98 wt. %, from 70 wt. % to 98 wt. %, from 70 wt. % to 95 wt. %, from 75 wt. % to 96 wt. %, from 80 wt. % to 96 wt. %, or from 85 wt. % to 96 wt. % $C_{18}$ to $C_{54}$ oligomers. In yet other embodiments, the oligomer product can comprise at least 35 wt. %, 40 wt. %, 45 wt. %, 50 wt. %, 55 wt. %, 60 wt. %, or 65 wt. % $C_{26}$ to $C_{54}$ oligomers. Additionally or alternatively, the oligomer product can comprise a maximum of 100 wt. %, 95 wt. %, 90 wt. %, or 85 wt. % $C_{26}$ to $C_{54}$ oligomers. In other embodiments, the oligomer product can comprise from 35 wt. % to 100 wt. %, from 40 wt. % to 95 wt. %, from 45 wt. % to 90 wt. %, from 40 wt. % to 85 wt. %, from 50 wt. % to 90 wt. %, or from 50 wt. % to 85 wt. %, $C_{26}$ to $C_{54}$ oligomers. In embodiments, the oligomer product can comprise less than 40 wt. %, 30 wt. %, 25 wt. %, 20 wt. %, 18 wt. %, 16 wt. %, 14 wt. %, 12 wt. %, or 10 wt. % ≤$C_{18}$ oligomers. In embodiments, the oligomer product can comprise less than 30 wt. %, 25 wt. %, 20 wt. %, 15 wt. %, 10 wt. %, 8 wt. %, 6 wt. %, 5 wt. %, 4 wt. %, 3 wt. %, or 2 wt. % ≥$C_{70}$ oligomers. The wt. % of the oligomer(s) disclosed herein is based upon the total weight of the oligomer product.

In embodiments, the oligomer product can be formed in the presence of (e.g., the reaction zone 10 contains) an organic reaction medium. The organic reaction medium can be a $C_3$ to $C_{18}$ saturated hydrocarbon. The organic reaction medium can be introduced to the reaction zone 10 prior to, simultaneously with, or after the introduction of i) the monomer, ii) the halide component, iii) the haloaluminate ionic liquid, or iv) combinations thereof to the reaction zone 10. In an embodiment, the organic reaction medium can be combined with any of the monomer, the halide component, the haloaluminate ionic liquid, or a combination thereof before introduction of the organic reaction medium to the reaction zone 10. In embodiments, the organic reaction medium can be introduced to the reaction zone 10 periodically or continuously. In embodiments having the organic reaction medium, said medium can be substantially devoid of isoparaffins. "Substantially devoid of isoparaffins" can include embodiments where the oligomer product can be formed in the presence of (e.g., the reaction zone 10 contains) less than 10 mol %, 9 mol %, 8 mol %, 7 mol %, 6 mol %, 5 mol %, 4 mol %, 3 mol %, 2 mol %, 1 mol % isoparaffins, based on moles of the monomer. In embodiments where the oligomer product is formed in the presence of (e.g., the reaction zone 10 contains) an organic reaction medium, an organic reaction medium to monomer volume ratio can be in the range of 0.25 to 20:1; alternatively, 0.25 to 15:1; alternatively, 0.5 to 10:1; alternatively, 0.5 to 7.5:1; or alternatively, 0.5 to 5:1. In alternative embodiments, the oligomer product can be formed in (e.g., the reaction zone 10 contains) a substantial absence of an organic reaction medium.

In embodiments, the oligomer product can be formed in (e.g., the reaction zone 10 contains) an inert atmosphere. An inert atmosphere can include the presence or absence of the organic reaction medium.

Returning to FIG. 1, the reaction zone effluent discharges from the reaction zone 10 via stream 12. The discharging of the reaction zone effluent can occur periodically or continuously. The separator 20 can separate the reaction zone effluent received from stream 12 into a first stream 22 and a second stream 24. The first stream 22 can comprise all or a portion of the haloaluminate ionic liquid (optionally, all or a portion of any halide component and/or organic reaction medium, if utilized) received in the separator 20 from the stream 12 (e.g., all or a portion of the haloaluminate ionic liquid in the reaction zone effluent). The second stream 24 can comprise, consist essentially of, or consist of the unreacted monomer, the oligomer product, and optionally, residual haloaluminate ionic liquid and/or organic reaction medium (if utilized). In embodiments, the separator 20 can be a coalescer, a centrifuge, a membrane, or any combination thereof. The operating configuration and conditions for the separator 20 can be the conditions known to those skilled in the art with the aid of this disclosure.

The haloaluminate ionic liquid (optionally, and any halide component) in first stream 22 can be recycled to the reaction zone 10. In an embodiment, the haloaluminate liquid in the first stream 22 flows to a regenerator 30, where the haloaluminate ionic liquid can be regenerated prior to re-introduction to the reaction zone 10. The haloaluminate ionic liquid can be regenerated by contacting the haloaluminate ionic liquid with aluminum under regeneration conditions.

It should be noted that the regenerator 30 can be comprised of one or more pieces of equipment; e.g., a reactor and a separator, among other options. Generally, the haloaluminate ionic liquid can be regenerated by contact with aluminum metal. In some embodiments, the haloaluminate ionic liquid and aluminum metal are contacted in the presence of hydrogen. The aluminum can be in the form of fine particles, granules, sponges, gauzes, etc.; alternatively, the aluminum can be in a macroscopic form that can include wires, foils, fine particles, sponges, gauzes, granules, etc.; or alternatively, the aluminum can be in a microscopic form that can include powders, smokes, colloidal suspensions, and condensed metal films. Generally, the hydrogen partial pressure at which the haloaluminate ionic liquid and aluminum can be contacted, when hydrogen is utilized, can range from 50 psig (345 kPa) to 2500 psig (17.2 MPa); or alternatively, 100 psig (689 kPa) to 2,500 psig (17.2 MPa). The ionic liquid regeneration conditions can include temperatures of −20° C. to 200° C. (or alternatively, 50° C. to 100° C.), and a contact time ranging from 0.1 minute to 24 hours (or alternatively, from 30 minutes to 2 hours. In some embodiments the ionic liquid regeneration can be performed in an inert hydrocarbon solvent (e.g., a $C_5$ to $C_{15}$ hydrocarbon; alternatively, a $C_5$ to $C_{18}$ hydrocarbon; alternatively, a $C_5$ to $C_{15}$ normal hydrocarbon; alternatively, a $C_5$ to $C_{18}$ normal hydrocarbon). Further information regarding the regeneration of the haloaluminate ionic liquid can be found in U.S. Pat. Nos. 7,732,364B2, 7,807,597B2, 7,732,363B2, and 7,691,771B2.

In FIG. 1, the regenerated haloaluminate ionic liquid flows from the regenerator 30 via stream 32. The fresh haloaluminate ionic liquid in stream 6 combines with the recycled haloaluminate ionic liquid of stream 32. The amount of haloaluminate ionic liquid flowing in feed stream 8 can equal the amount of the fresh haloaluminate ionic liquid flowing in stream 6 plus the amount of recycled haloaluminate ionic liquid flowing in stream 32. In embodiments, the weight ratio of fresh haloaluminate ionic liquid to recycled haloaluminate ionic liquid (e.g., in feed stream 8, reaction zone 10, or both) can be from 0.1:1 to 10:1. In some embodiments, the recycled haloaluminate ionic liquid may not be regenerated. In the embodiments where the haloaluminate ionic liquid is not regenerated, the weight ratio of fresh haloaluminate ionic liquid to recycled haloaluminate ionic liquid can be the same as the weight ratio of fresh haloaluminate ionic liquid to recycled haloaluminate ionic liquid when the ionic liquid is regenerated. In other embodiments, the recycled haloaluminate ionic liquid (regenerated or not regenerated) can be introduced directly to the reaction zone 10; or alternatively the recycled haloaluminate ionic liquid (regenerated or not regenerated) can be introduced into any feed stream to reaction zone 10 containing haloaluminate ionic liquid disclosed herein.

In embodiments, the second stream 24 can optionally be treated to remove any residual catalyst system components (e.g., haloaluminate ionic liquid, halide component, or both) present in the second stream 24. In embodiments where the second stream 24 is treated to remove residual catalyst system components, the second stream 24 can flow to a treating unit (not shown) to quench or remove the residual catalyst system components such that substantially all the haloaluminate ionic liquid and/or the halide component is separated from the unreacted monomer and the oligomer product. Removal of "substantially all" the haloaluminate ionic liquid can refer to removal of the haloaluminate ionic liquid from stream 24 to form a stream containing less than 5, 4, 3, 2, 1, 0.5, 0.4, 0.3, 0.2, or 0.1 mol % of the haloaluminate ionic liquid in reaction zone effluent (stream 12). Likewise, removal of "substantially all" the halide component can refer to removal of the halide component from stream 24 to form a stream containing less than 5, 4, 3, 2, 1, 0.5, 0.4, 0.3, 0.2, or 0.1 mol % of the halide component in reaction zone effluent (stream 12). In embodiments having a treating unit, a washing agent (e.g., aqueous alkali metal hydroxide or anhydrous ammonia) can be contacted with the second stream 24 in the treating unit. The washing agent can facilitate the removal of residual catalyst system components (e.g., haloaluminate ionic liquid and/or halide component) from the unreacted monomer and the oligomer product. Once treated in the treating unit, the treated second stream 24 comprising unreacted monomer and oligomer product (and any organic reaction medium, if utilized) and the washing agent contacted with the second stream 24 can flow from the treating unit via separate streams and further processed as described herein.

Embodiments of the oligomerization shown in FIG. 1 can include controlling certain parameters to achieve a selected average molecular weight (Mn) of the oligomer product. For example, the average molecular weight (Mn) of the oligomer product can be controlled by selecting an average molecular weight for the oligomer product and adjusting (i) a molar ratio of carbon-carbon double bonds of the monomer to aluminum in the haloaluminate ionic liquid, (ii) molar ratio of halide in the halide component to aluminum in the haloaluminate ionic liquid, or a combination of (i) and (ii) to achieve the selected average molecular weight of the oligomer product. Alternatively, or additionally, the average molecular weight (Mn) of the oligomer product can be controlled by selecting an average molecular weight for the oligomer product and adjusting (i) the temperature at which the oligomer product is formed, (ii) the time over which the oligomer product can be formed, or iii) any combination of (i) and (ii).

Embodiments of the disclosure include producing one or more hydrogenated fractions comprising all or a portion of the hydrogenated oligomer product. In embodiments of the disclosure, the production of the one or more hydrogenated fractions comprising all or a portion of the hydrogenated oligomer product can include isolating one or more fractions of all or a portion of the oligomer product followed by hydrogenating at least one of the one or more fractions. In other embodiments, a stream comprising all or a portion of the oligomer product can be hydrogenated to produce a fraction comprising all or a portion of the hydrogenated oligomer product and the fraction comprising all or a portion of the hydrogenated oligomer product can then be separated into one or more hydrogenated fractions comprising all or a portion of the hydrogenated oligomer product. In other embodiments, a stream consisting essentially of all or a portion of the oligomer product can be hydrogenated to produce a fraction comprising all or a portion of the hydrogenated oligomer product and the fraction comprising all or a portion of the hydrogenated oligomer product can then be separated into one or more hydrogenated fractions containing all or a portion of the hydrogenated oligomer product. Generally, the production of one or more hydrogenated fractions comprising all or a portion of the hydrogenated oligomer product can include a combination of separation steps and hydrogenation steps.

In an embodiment, the processes described herein can include isolating the one or more fractions of all or a portion of the oligomer product. Isolating the one or more fractions of all or a portion of the oligomer product can include: i) separating the oligomer product from the unreacted monomer, fractionating the oligomer product into one or more fractions, and optionally recycling the unreacted monomer to the reaction zone 10; separating the oligomer product from the monomer and the organic reaction medium (if utilized), fractionating the oligomer product into one or more fractions, and optionally recycling the unreacted monomer and organic reaction medium to the reaction zone 10; separating a heavier portion of the oligomer product from the unreacted monomer and a lighter portion of the oligomer product, fractionating the heavier portion into one or more fractions, and optionally recycling the unreacted monomer and the lighter portion of the oligomer product to the reaction zone 10; or separating the heavier portion of the oligomer product from the monomer, the lighter portion of the oligomer product, and the organic reaction medium, fractionating the heavier portion of the oligomer product, and optionally recycling the unreacted monomer, the lighter portion of the oligomer product, and/or the organic reaction medium to the reaction zone 10. The separations and fractionations can be performed using any known process. In some embodiments, one or more of the separating and fractionating step(s) can be performed by distillation.

Figure 2:
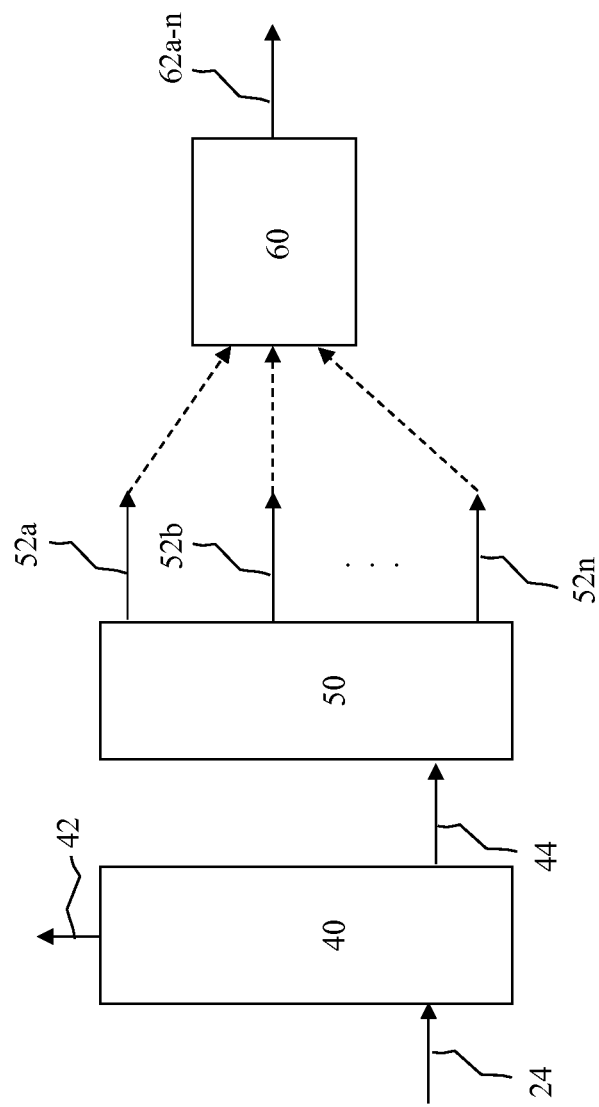
FIG. 2 illustrates an embodiment for isolating one or more fractions of the oligomer product.
Figure 3:
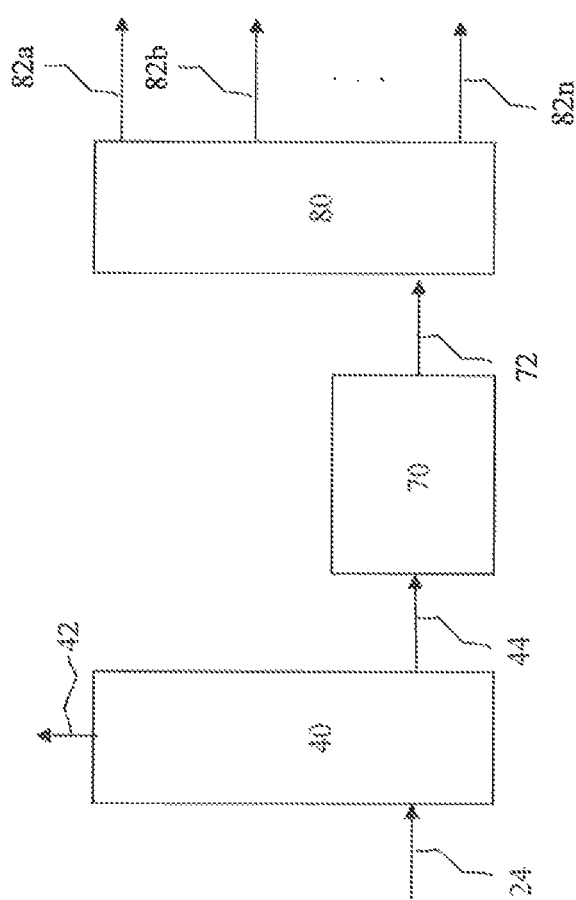
FIG. 3 illustrates an alternative embodiment for isolating one or more fractions of the oligomer product.
Figure 4:
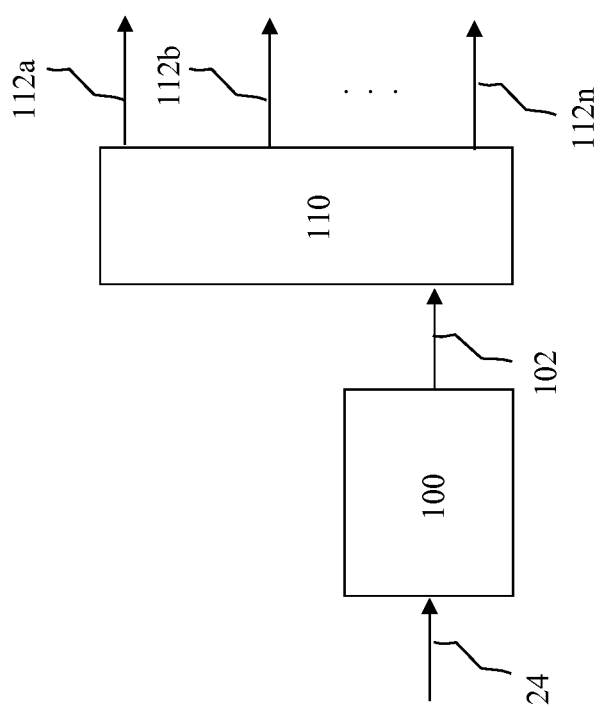
FIG. 4 illustrates another alternative embodiment for isolating one or more fractions of the oligomer product.

FIGS. 2 to 4 illustrate various embodiments for isolating the one or more fractions of all or a portion of the oligomer product and hydrogenating at least one of the one or more fractions of all or a portion of the oligomer product.

Referring to FIG. 2, a separator 40 receives the second stream 24 (which can be optionally treated to remove residual catalyst system components). In separator 40, the unreacted monomer, organic reaction medium (if utilized) and oligomer product can be separated into a third stream 42 and a fourth stream 44. The compositions of the third stream 42 and fourth stream 44 include several embodiments. A first embodiment of the third stream 42 and fourth stream 44 includes a third stream 42 which comprises, consists essentially of, or consists of unreacted monomer, organic reaction medium (if utilized), and ≤$C_{18}$ oligomers and a fourth stream 44 which comprises, consists essentially of, or consists of ≥$C_{19}$ oligomers. A second embodiment of the third stream 42 and fourth stream 44 includes a third stream which comprises, consists essentially of, or consists of unreacted monomer, organic reaction medium (if utilized), and ≤$C_{25}$ oligomers and a fourth stream 44 which comprises, consists essentially of, or consists of ≥$C_{26}$ oligomers. A third embodiment of the third stream 42 and fourth stream 44 includes a third stream 42 which comprises, consists essentially of, or consists of unreacted monomer, organic reaction medium (if utilized), and a fourth stream 44 which comprises, consists essentially of, or consists of the oligomer product. A fourth embodiment of the third stream 42 and the fourth stream 44 includes a third stream 42 which comprises, consists essentially of, or consists of or unreacted monomer, organic reaction medium (if utilized), and dimer and a fourth stream 44 which comprises, consists essentially of, or consists of trimer and heavier oligomers (also referred to herein as "trimer+ oligomers"). The "≤$C_{18}$ oligomers," "≤$C_{25}$ oligomers," and "dimer" of the embodiments of the third stream 42 can be referred to as "lighter oligomers." The "≥$C_{19}$ oligomers," "≥$C_{26}$ oligomers," and "trimer+ oligomers" of the embodiments of the fourth stream 44 can be referred to as "heavier oligomers." Embodiments contemplate that the organic reaction medium, if utilized, can be included in the stream 24 and can be separated from the monomer and oligomer product prior to separator 40 or can be separated from any all or portion of the oligomer product described herein by separator 40 into third stream 42.

FIG. 2 illustrates the components (e.g., unreacted monomer, lighter oligomers, organic reaction medium (if utilized), or any combination thereof) in the third stream 42 can optionally be recycled to the reaction zone 10. In embodiments where the component of the third stream are recycled to the reactor, the components of the third stream 42 can be optionally contacted with a molecular sieve, alumina, silica gel, activated carbon, or any combination thereof (not shown) prior to being recycled to the reaction zone 10. In an embodiment wherein the third stream 42 can be optionally contacted with a molecular sieve, alumina, silica gel, activated carbon, or any combination thereof, the components of the third stream 42 can flow from the separator 40 to a contacting unit (not shown), where the components are contacted with a molecular sieve, alumina, silica gel, activated carbon, or any combination thereof. The contacted components (e.g., unreacted monomer, lighter oligomers, organic reaction medium (if utilized), or any combination thereof) can flow from the contacting unit and can be recycled to the reaction zone 10 of FIG. 1. In an embodiment, the separator 40 is a distillation column. It should be noted that while FIG. 2 shows all of the third stream 42 is recycled to the reactor, it is contemplated that only a portion of the third stream 42 can be recycled to the reaction, can be subjected to further separations to provide streams comprising the unreacted monomer, the lighter oligomers (if present in the third stream 42), and/or all or portion of the components can be stored for a period of time prior to being recycled to reaction zone 10 of FIG. 1.

In FIG. 2, the fourth stream 44 flows to fractionation zone 50. In fractionation zone 50, the components of the fourth stream 44 (e.g., all or a portion of the oligomer product, e.g., heavier oligomers of the oligomer product) can be fractionated into one or more fractions using one or more separation devices (e.g., distillation columns). In the embodiment where the fourth stream 44 comprises the oligomer product, the fractionation zone 50 can fractionate the oligomer product into one or more fractions comprising all or a portion of the oligomer product. In the embodiment where the fourth stream 44 comprises the ≥$C_{19}$ oligomers of the oligomer product, the fractionation zone 50 can fractionate the ≥$C_{19}$ oligomers into one or more fractions comprising all or a portion of the ≥$C_{19}$ oligomers. In the embodiment where the fourth stream 44 comprises the ≥$C_{26}$ oligomers of the oligomer product, the fractionation zone 50 can fractionate the ≥$C_{26}$ oligomers into one or more fractions comprising all or a portion of the ≥$C_{26}$ oligomers. In the embodiment where the fourth stream 44 comprises the trimer+ oligomers of the oligomer product, the fractionation zone 50 can fractionate the trimer+ oligomers into one or more fractions comprising all or a portion of the trimer+ oligomers.

In an embodiment where the fourth stream 44 can comprise the oligomer product, the one or more fractions comprising all or a portion of the oligomer product can be selected from the group consisting of: a) a fraction comprising from 90 wt. % to 100 wt. % dimer, b) a fraction comprising 80 wt. % to 90 wt. % trimer and 8 wt. % to 18 wt. % tetramer, c) a fraction comprising 85 wt. % to 95 wt. % trimer and 3 wt. % to 13 wt. % tetramer, d) a fraction comprising 20 wt. % to 35 wt. % trimer, 40 wt. % to 60 wt. % tetramer, and 13 wt. % to 27 wt. % pentamer, e) a fraction comprising 35 wt. % to 55 wt. % trimer and 40 wt. % to 60 wt. % tetramer, f) a fraction comprising 45 wt. % to 65 wt. % tetramer, 22 wt. % to 34 wt. % pentamer, and 5 wt. % to 15 wt. % $C_{56}$ to $C_{64}$ hexamer, g) a fraction comprising 12 wt. % to 24 wt. % trimer, 37 wt. % to 57 wt. % tetramer, 13 wt. % to 25 wt. % pentamer, and 6 wt. % to 18 wt. % hexamer+, h) a fraction comprising 30 wt. % to 42 wt. % tetramer, 27 wt. % to 39 wt. % pentamer, 10 wt. % to 22 wt. % hexamer, and 9 wt. % to 21 wt. % heptamer+, and i) any combination of fractions a) to h).

In an embodiment where the fourth stream 44 can comprise the $\geq C_{19}$ oligomers of the oligomer product, the one or more fractions comprising all or a portion of the $\geq C_{19}$ oligomers can be selected from the group consisting of: a) a fraction comprising from 90 wt. % to 100 wt. % $C_{19}$ to $C_{22}$ oligomers, b) a fraction comprising 90 wt. % to 100 wt. % $C_{22}$ to $C_{26}$ oligomers, c) a fraction comprising 80 wt. % to 90 wt. % $C_{26}$ to $C_{34}$ oligomers and 8 wt. % to 18 wt. % $C_{36}$ to $C_{44}$ oligomers, d) a fraction comprising 85 wt. % to 95 wt. % $C_{32}$ to $C_{40}$ oligomers and 3 wt. % to 13 wt. % $C_{44}$ to $C_{52}$ oligomers, e) a fraction comprising 20 wt. % to 35 wt. % $C_{26}$ to $C_{34}$ oligomers, 40 wt. % to 60 wt. % $C_{36}$ to $C_{44}$ oligomers, and 13 wt. % to 27 wt. % $C_{46}$ to $C_{54}$ oligomers, f) a fraction comprising 35 wt. % to 55 wt. % $C_{32}$ to $C_{40}$ oligomers and 40 wt. % to 60 wt. % $C_{44}$ to $C_{52}$ oligomers, g) a fraction comprising 45 wt. % to 65 wt. % $C_{36}$ to $C_{44}$ oligomers, 22 wt. % to 34 wt. % $C_{46}$ to $C_{54}$ oligomers, and 5 wt. % to 15 wt. % $C_{56}$ to $C_{64}$ oligomers, h) a fraction comprising 12 wt. % to 24 wt. % $C_{32}$ to $C_{40}$ oligomers, 37 wt. % to 57 wt. % $C_{44}$ to $C_{52}$ oligomers, 13 wt. % to 25 wt. % $C_{56}$ to $C_{64}$ oligomers, and 6 wt. % to 18 wt. % $\geq C_{68}$ oligomers, i) a fraction comprising 30 wt. % to 42 wt. % $C_{36}$ to $C_{44}$ oligomers, 27 wt. % to 39 wt. % $C_{46}$ to $C_{54}$ oligomers, 10 wt. % to 22 wt. % $C_{56}$ to $C_{64}$ oligomers, and 9 wt. % to 21 wt. % $\geq C_{66}$ oligomers, and j) any combination of fractions a) to i).

In an embodiment where the fourth stream 44 can comprise the $\geq C_{26}$ oligomers of the oligomer product, the one or more fractions comprising all or a portion of the $\geq C_{26}$ oligomers can be selected from the group consisting of: a) a fraction comprising 80 wt. % to 90 wt. % $C_{26}$ to $C_{34}$ oligomers and 8 wt. % to 18 wt. % $C_{26}$ to $C_{34}$ oligomers, b) a fraction comprising 85 wt. % to 95 wt. % $C_{32}$ to $C_{40}$ oligomers and 3 wt. % to 13 wt. % $C_{44}$ to $C_{52}$ oligomers, c) a fraction comprising 20 wt. % to 35 wt. % $C_{26}$ to $C_{34}$ oligomers, 40 wt. % to 60 wt. % $C_{36}$ to $C_{44}$ oligomers, and 13 wt. % to 27 wt. % $C_{46}$ to $C_{54}$ oligomers, d) a fraction comprising 35 wt. % to 55 wt. % $C_{32}$ to $C_{40}$ oligomers and 40 wt. % to 60 wt. % $C_{44}$ to $C_{52}$ oligomers, e) a fraction comprising 45 wt. % to 65 wt. % $C_{36}$ to $C_{44}$ oligomers, 22 wt. % to 34 wt. % $C_{46}$ to $C_{54}$ oligomers, and 5 wt. % to 15 wt. % $C_{56}$ to $C_{64}$ oligomers, f) a fraction comprising 12 wt. % to 24 wt. % $C_{32}$ to $C_{40}$ oligomers, 37 wt. % to 57 wt. % $C_{44}$ to $C_{52}$ oligomers, 13 wt. % to 25 wt. % $C_{56}$ to $C_{64}$ oligomers, and 6 wt. % to 18 wt. % $\geq C_{68}$ oligomers, g) a fraction comprising 30 wt. % to 42 wt. % $C_{36}$ to $C_{44}$ oligomers, 27 wt. % to 39 wt. % $C_{46}$ to $C_{54}$ oligomers, 10 wt. % to 22 wt. % $C_{56}$ to $C_{64}$ oligomers, and 9 wt. % to 21 wt. % $\geq C_{66}$ oligomers, and h) any combination of fractions a) to g).

In an embodiment where the fourth stream 44 comprise the trimer+ oligomers of the oligomer product, the one or more fractions comprising all or a portion of the trimer+ oligomers can be selected from the group consisting of: a) a fraction comprising 80 wt. % to 90 wt. % trimer and 8 wt. % to 18 wt. % tetramer, b) a fraction comprising 85 wt. % to 95 wt. % trimer and 3 wt. % to 13 wt. % tetramer, c) a fraction comprising 20 wt. % to 35 wt. % trimer, 40 wt. % to 60 wt. % tetramer, and 13 wt. % to 27 wt. % pentamer, d) a fraction comprising 35 wt. % to 55 wt. % trimer and 40 wt. % to 60 wt. % tetramer, e) a fraction comprising 45 wt. % to 65 wt. % tetramer, 22 wt. % to 34 wt. % pentamer, and 5 wt. % to 15 wt. % $C_{56}$ to $C_{64}$ hexamer, f) a fraction comprising 12 wt. % to 24 wt. % trimer, 37 wt. % to 57 wt. % tetramer, 13 wt. % to 25 wt. % pentamer, and 6 wt. % to 18 wt. % hexamer+, g) a fraction comprising 30 wt. % to 42 wt. % tetramer, 27 wt. % to 39 wt. % pentamer, 10 wt. % to 22 wt. % hexamer, and 9 wt. % to 21 wt. % heptamer+, and h) any combination fractions a) to g).

FIG. 2 shows that the one or more fractions can flow from the fractionation zone 50 via streams 52a, 52b, . . . 52n, where "n" represents the number of streams which are formed by the fractionation zone 50. The present disclosure contemplates that a single fraction or more than one fraction can be formed in fractionation zone 50 (e.g., streams 52a, 52b, . . . 52n). In an embodiment, "n" for the number of streams 52a-n formed by fractionation zone 50 can be 2, 3, 4, 5, 6, 7, 8, 9, 10, or more.

Following the fractionation of the oligomer product (or a heavier oligomer portion thereof) into the one or more fractions, the unsaturation in at least one of the one or more fractions can be reduced by hydrogenating at least one of the one or more fractions (e.g., at least one fraction formed from the stream comprising all or a portion of the oligomer product, comprising all or a portion of the $\geq C_{19}$ oligomers, comprising all or a portion of the $\geq C_{26}$ oligomers, comprising all or a portion of the trimer+ oligomers) to form a polyalphaolefin(s). FIG. 2 shows at least one of the one or more fractions in streams 52a-n (designated by dashed lines) can flow to a hydrogenation zone 60 for hydrogenation. The present disclosure contemplates that at least one (one or any combination) of streams 52a-n can feed (separately, simultaneously, separately and simultaneously, periodically, continuously, or any combination thereof) to the hydrogenation zone 60. For example, the disclosed embodiments contemplate streams 52a and 52b may feed to hydrogenation zone 60 and stream 52n may not feed to hydrogenation zone 60; alternatively, stream 52a may feed to hydrogenation zone 60 and streams 52b and 52n may not feed to hydrogenation zone 60; and so on. It is further contemplated that hydrogenation zone 60 can include one or more hydrogenation units (e.g., one hydrogenation unit per stream to be hydrogenated. Additionally, it is contemplated that each stream to be hydrogenated can be separately hydrogenated in a single hydrogenation unit.

In a hydrogenation unit within hydrogenation zone 60, hydrogenation of the one or more fractions can be accomplished by any means known to those with ordinary skill in the art with the aid of this disclosure. A hydrogenation unit within hydrogenation zone 60 can hydrogenate unsaturated double bonds of the one or more fractions to yield a hydrogenated product comprising, for example, polyalphaolefins. In some embodiments, the one or more fractions can be stored for a period of time prior to hydrogenation in a hydrogenation unit within hydrogenation zone 60.

In an embodiment, any of the one or more fractions of all or a portion of the oligomer product isolated by the embodiments described herein can be hydrogenated by reaction with hydrogen gas to form a polyalphaolefin. Generally, the hydrogenation can comprise contacting the one or more fractions of all or a portion of the oligomer product and a hydrogenation catalyst to form a polyalphaolefin under conditions capable of hydrogenating the one or more fractions of all or a portion of the oligomer product. In some embodiments, the one or more fractions of all or a portion of the oligomer product can be hydrogenated to produce a polyalphaolefin having any bromine number or bromine index described herein.

In an embodiment, the hydrogenation catalyst can comprise, or consist essentially of, a supported Group 7, 8, 9, and 10 metals. In some embodiments, the hydrogenation catalyst can be selected from the group consisting of one or more of Ni, Pd, Pt, Co, Rh, Fe, Ru, Os, Cr, Mo, and W, supported on silica, alumina, clay, titania, zirconia, or a mixed metal oxide supports. In other embodiments, the hydrogenation catalyst can be nickel supported on kieselguhr, platinum or palladium supported on alumina, or cobalt-molybdenum supported on alumina; alternatively, nickel supported on kieselguhr; alternatively, platinum or palladium supported on alumina; or alternatively, cobalt-molybdenum supported on alumina. In yet other embodiments, the hydrogenation catalyst can be one or more of the group consisting of nickel supported on kieselguhr, silica, alumina, clay or silica-alumina.

Generally, the hydrogenation of the one or more fractions of all or a portion of the oligomer product to form a polyalphaolefin can be performed in any type of process and/or reactor which can hydrogenate the one or more fractions of all or a portion of the oligomer product to the desired bromine number or bromine index. In an embodiment, the hydrogenation of the one or more fractions to form a polyalphaolefin can be performed in a batch process, a continuous process; or any combination thereof, alternatively a batch process; or alternatively a continuous process. In some embodiments, the hydrogenation of the one or more fractions of all or a portion of the oligomer product to form a polyalphaolefin can be performed in a slurry reactor, a continuous stirred tank reactor, a fixed bed reactor or any combination thereof; alternatively, a slurry reactor; alternatively, a continuous stirred tank reactor; or alternatively, a fixed bed reactor.

Generally, the product polyalphaolefin (i.e., a hydrogenated fraction of all or a portion of the oligomer product) is removed from the hydrogenation unit as stream 62a-n. The product polyalphaolefin can be filtered to separate the hydrogenation catalyst and/or catalyst fines from the polyalphaolefin. Further, the polyalphaolefin can be distilled to further purify the polyalphaolefin; alternatively, distilled to form two or more compositions comprising, or consisting essentially of, polyalphaolefins having different nominal viscosities; or alternatively, distilled to further purify the polyalphaolefin and form two or more compositions comprising, or consisting essentially of, polyalphaolefins having different nominal viscosities.

The quantity of hydrogenation catalyst utilized to hydrogenate the one or more fractions is dependent upon the identity of the hydrogenation catalyst and the particular hydrogenation process utilized. Generally, the amount of hydrogenation catalyst used can be any amount which can produce the desired polyalphaolefin bromine number (or bromine index) under the desired conditions capable of forming the polyalphaolefin. In a non-fixed bed hydrogenation process (e.g., slurry reactors or continuous stirred tank reactors, among others), the amount of hydrogenation catalyst used in the hydrogenation can range from 0.001 wt. % to 20 wt. %, 0.01 wt. % to 15 wt. %, 0.1 wt. % to 10 wt. %, or 1 wt. % to 5 wt. %. In a fixed bed processes, the WHSV (weight hourly space velocity) of the one or more fractions over the hydrogenation catalyst can range from 0.01 to 10, 0.05 to 7.5, or 0.1 to 5. The wt. % of the hydrogenation catalyst is based upon the total weight of the hydrogenation catalyst and one or more fractions being subjected to hydrogenation.

Generally, the conditions capable of hydrogenating the one or more fractions of all or a portion of the oligomer product can comprise a hydrogen pressure, a temperature, a contact time, or any combination thereof; alternatively, a hydrogen pressure and a temperature; alternatively, a hydrogen pressure, a temperature, and a contact time. In an embodiment, the temperature of the hydrogenation that can be utilized as a condition capable of hydrogenating the one or more fractions of all or a portion of the oligomer product can range from 25° C. to 350° C., from 50° C. to 300° C., from 60° C. to 250° C., or from 70° C. to 200° C. In an embodiment, the hydrogen pressure that can be utilized as a condition capable of hydrogenating the one or more fractions of all or a portion of the oligomer product can range from 100 kPa to 10 MPa, 250 kPa to 7 MPa, 500 kPa to 5 MPa, or 750 kPa to 2 MPa. In an embodiment, the contact time that can be utilized as a condition capable of hydrogenating the one or more fractions of all or a portion of the oligomer product can range from 1 minutes to 100 hours, from 2 minutes to 50 hours, 5 minutes to 25 hour, or 10 minute to 10 hours. Additional information on the hydrogenation to produce a polyalphaolefin (e.g., olefin oligomer such as the one or more fractions that can be produced by the embodiments described herein) to form polyalphaolefins can be found in U.S. Pat. No. 5,573,657 and "Lubricant Base Oil Hydrogen Refining Processes" (page 119 to 152 of Lubricant Base Oil and Wax Processing, by Avilino Sequeira, Jr., Marcel Dekker, Inc., NY (1994)).

The present disclosure contemplates that separator 40 and fractionation zone 50 of FIG. 2 can be combined into a single unit where all or a portion of the components in second stream 24 (e.g., unreacted monomer, oligomer product, organic reaction medium, if utilized) can be fractionated as well as separated such that the unreacted monomer, any organic reaction medium (if utilized), or any combination thereof can be recovered in a first group of the one or more fractions and the oligomer product can be recovered in a second group of the one or more fractions of the oligomer product; or alternatively, the unreacted monomer, any organic reaction medium (if utilized), lighter oligomers (e.g., dimer, $\leq C_{18}$ oligomers, or $\leq C_{25}$ oligomers), or any combination thereof can be recovered in a first group of the one or more fractions and the heavier oligomers can be recovered in a second group of the one or more fractions. That is, in some embodiments, the oligomer product or heavier portion of the oligomer product can be separated concurrently with the separation from the unreacted monomer and organic reaction medium (if utilized) into one or more fractions comprising, consisting of, or consisting essentially of all or a portion of the oligomer product or the heavier oligomers (e.g., the $\geq C_{19}$ oligomers, the $\geq C_{26}$ oligomers, or the trimers+ oligomers). In such embodiments, the unreacted monomer and organic reaction medium (if utilized) flowing from the single unit can be optionally recycled and optionally contacted with a molecular sieve, alumina, silica gel, activated carbon, or any combination thereof, in the contacting unit (not shown) described for FIG. 2 before being recycled, to the reaction zone 10.

FIG. 3 shows another embodiment for isolating one or more fractions of hydrogenated oligomer product and hydrogenating at least one of the one or more fractions of all or a portion of the oligomer product. In the embodiment of FIG. 3, the second stream 24 (which can be optionally treated to remove residual catalyst system components) is received by the separator 40, and the separator produces third stream 42 and fourth stream 44 having the embodiments discussed for FIG. 2. Moreover, as in FIG. 2, the components of the third stream 42 can be optionally contacted with a molecular sieve, alumina, silica gel, activated carbon, or any combination thereof in a contacting unit prior to being optionally recycled to the reaction zone 10 of FIG. 1. It should be noted that while FIG. 3 shows all of the third stream 42 is recycled to the reactor, it is contemplated that only a portion of the third stream 42 can be recycled to the reaction, can be subjected to further separations to provide streams comprising the unreacted monomer, the lighter oligomers (if present in the third stream 42), and/or all or portion of the components can be stored for a period of time prior to being recycled to the reaction zone 10 of FIG. 1.

Different from the embodiment in FIG. 2, the fourth stream 44 in FIG. 3 flows to a hydrogenation unit 70 where the oligomer product or a heavier portion of the oligomer product (e.g., $\geq C_{19}$ oligomers, $\geq C_{26}$ oligomers, or trimer+ oligomers) is hydrogenated to yield a hydrogenated oligomer product or hydrogenated heavier portion of the oligomer product. In some embodiments, the oligomer product or a heavier portion of the oligomer product (e.g., $\geq C_{19}$ oligomers, $\geq C_{26}$ oligomers, or trimer+ oligomers) can be stored for a period of time prior to entering hydrogenation unit 70. The hydrogenated oligomer product can comprise, consist essentially of, or consist of all or a portion of the oligomer product. The hydrogenated heavier portion of the oligomer product can comprise, consist essentially of, or consist of all or a portion of the heavier oligomer product. The hydrogenation conditions for hydrogenation unit 70 can be similar to those disclosed for the hydrogenation units of hydrogenation zone 60 in FIG. 2. The hydrogenated oligomer product or the hydrogenated heavier portion of the oligomer product (e.g. ≥hydrogenated $C_{19}$ oligomers, hydrogenated $\geq C_{26}$ oligomers, or hydrogenated trimer+ oligomers) flows in stream 72 from the hydrogenation unit 70 to fractionation zone 80. In some embodiments, the hydrogenated oligomer product or the hydrogenated heavier portion of the oligomer product (e.g. ≥hydrogenated $C_{19}$ oligomers, hydrogenated $\geq C_{26}$ oligomers, or hydrogenated trimer+ oligomers) can be stored for a period of time prior to entering fractionation zone 80. Fractionation zone 80 can operate under similar conditions as disclosed for fractionation zone 50 in FIG. 2, except fractionation zone 80 and the conditions therein are configured to facilitate fractionation of the hydrogenated oligomer product or hydrogenated heavier portion of the oligomer product into one or more hydrogenated fractions. In embodiments, the hydrogenated oligomer product is fractionated into one or more hydrogenated fractions comprising all or a portion of the hydrogenated oligomer product; the hydrogenated $\geq C_{19}$ oligomers are fractionated into one or more hydrogenated fractions comprising all or a portion of the hydrogenated $\geq C_{19}$ oligomers; the hydrogenated $\geq C_{26}$ oligomers are fractionated into one or more hydrogenated fractions comprising all or a portion of the hydrogenated $\geq C_{26}$ oligomers; or the hydrogenated trimer+ oligomers are fractionated into one or more hydrogenated fractions comprising all or a portion of the hydrogenated trimer+ oligomers. Generally, fractionation zone 80 in FIG. 3 can form a hydrogenated version of any of the one or more fractions comprising all or a portion of the oligomer product, a hydrogenated version of any of the one or more fractions comprising all or a portion of the $\geq C_{19}$ oligomers, the hydrogenated version of the one or more fractions comprising all or a portion of the $\geq C_{26}$ oligomers, or the hydrogenated version of the one or more fractions comprising all or a portion of the trimer+ oligomers which can be formed the fourth stream 44 of FIG. 2. The hydrogenated versions of any these one or more fractions are described in further detail herein and can be utilized to further describe the process described herein.

FIG. 3 shows that the one or more hydrogenated fractions can flow from the fractionation zone 80 via streams 82a, 82b, . . . 82n, where "n" represents the number of hydrogenated streams formed in fractionation zone 80. The present disclosure contemplates that a single hydrogenated fraction or more than one hydrogenated fraction can be formed in fractionation zone 80 (e.g., streams 82a, 82b, . . . 82n). In an embodiment, "n" for the number of streams 82a-n formed by fractionation zone can be 2, 3, 4, 5, 6, 7, 8, 9, 10, or more.

Embodiments of the disclosure contemplate that following the fractionation of the hydrogenated oligomer product (or a hydrogenated heavier portion of the oligomer product) in fractionation zone 80 into the one or more hydrogenated fractions, any one of the one or more hydrogenated fractions in streams 82a-n can undergo a finishing hydrogenation by hydrogenating any one of the one or more hydrogenated fractions. In embodiments having a finishing hydrogenation step, any of streams 82a-n can feed to a finishing hydrogenation unit in the same manner as described for streams 52a-n feeding to a hydrogenation unit in hydrogenation zone 60 in FIG. 2. In some embodiments, the one or more hydrogenated fractions can be stored for a period of time prior to a finishing hydrogenation.

FIG. 4 shows another alternative embodiment for isolating one or more fractions of hydrogenated oligomer product. In the embodiment of FIG. 4, the second stream 24 (which may be optionally treated to remove residual catalyst system components) is received by a hydrogenating unit 100. As can be seen, there is no separating unit 40 as is shown in FIGS. 2 and 3, and no components are recycled to the reaction zone 10 prior to the hydrogenation in the embodiment of FIG. 4. Instead, all components (e.g., unreacted monomer, organic reaction medium, oligomer product, or combinations thereof) flow to the hydrogenating unit 100 in second stream 24. The unreacted monomer, organic reaction medium (if utilized), and the oligomer product in the second stream 24 are hydrogenated in hydrogenation unit 100 to yield a hydrogenated stream 102 comprising, consisting essentially of, or consisting of a hydrogenated oligomer product, organic reaction medium (if utilized), and hydrogenated unreacted monomer. The hydrogenated oligomer product can comprise all or a portion of the oligomer product. The hydrogenation conditions for hydrogenation unit 100 can be similar to those disclosed for a hydrogenation unit in the hydrogenation zone 60 in FIG. 2.

The hydrogenated stream 102 can flow from the hydrogenating unit 100 to fractionation zone 110. In fractionation zone 110, the hydrogenated oligomer product is separated from the hydrogenated stream 102 into one or more hydrogenated fractions comprising all or a portion of the hydrogenated oligomer product to yield a polyalphaolefin. In some embodiments, hydrogenated stream 102 can be stored for a period of time prior to entering fractionation zone 110. Fractionation zone can further provide 1) a stream comprising the hydrogenated unreacted monomer, a stream comprising the organic reaction medium, or 3) a combination of 1) and 2). In some embodiments, the organic reaction medium can be recycled to reaction zone 10 of FIG. 1. In some embodiments, the organic reaction medium can be stored for a period of time prior to prior being recycled to reaction zone 10 of FIG. 1.

Fractionation zone 110 can operate under the conditions similar to those disclosed for fractionation zone 50 in FIG. 2, except fractionation zone 110 and the conditions therein are configured to facilitate fractionation of the hydrogenated oligomer product into one or more hydrogenated fractions. In embodiments, the hydrogenated oligomer product is fractionated into one or more hydrogenated fractions comprising all or a portion of the hydrogenated oligomer product; the hydrogenated $\geq C_{19}$ oligomers are fractionated into one or more hydrogenated fractions comprising all or a portion of the hydrogenated $\geq C_{19}$ oligomers; the hydrogenated $\geq C_{26}$ oligomers are fractionated into one or more hydrogenated fractions comprising all or a portion of the hydrogenated $\geq C_{26}$ oligomers; or the hydrogenated trimer+ oligomers are fractionated into one or more hydrogenated fractions comprising all or a portion of the hydrogenated trimer+ oligomers. Generally, fractionation zone 110 in FIG. 4 can form a hydrogenated version of any of the one or more fractions comprising all or a portion of the oligomer product, a hydrogenated version of any of the one or more fractions comprising all or a portion of the $\geq C_{19}$ oligomers, the hydrogenated version of the one or more fractions comprising all or a portion of the $\geq C_{26}$ oligomers, or the hydrogenated version of the one or more fractions comprising all or a portion of the trimer+ oligomers which can be formed the forth stream 44 of FIG. 2.

FIG. 4 shows the one or more hydrogenated fractions can flow from the fractionation zone 110 via streams 112a, 112b, . . . 112n, where "n" represents the number of hydrogenated streams formed in the fractionation zone 110. The present disclosure contemplates that a single hydrogenated fraction or more than one hydrogenated fraction can be formed in fractionation zone 110 (e.g., streams 112a, 112b, . . . 112n. In an embodiment, "n" for the number of streams 112a-n formed by fractionation zone 110 can be 2, 3, 4, 5, 6, 7, 8, 9, 10, or more.

Embodiments contemplate that following the fractionation of the hydrogenated stream 102 in fractionation zone 110 into the one or more hydrogenated fractions, any one of the one or more hydrogenated fractions in streams 112a-n can undergo a finishing hydrogenation by hydrogenating any one of the one or more hydrogenated fractions. In embodiments having a finishing hydrogenation step, any of streams 112a-n can feed to a finishing hydrogenation unit in the same manner as described for streams 52a-n feeding to a hydrogenation unit in hydrogenation zone 60 in FIG. 2. In some embodiments, the one or more hydrogenated fractions can be stored for a period of time prior to a finishing hydrogenation.

Generally, the polyalphaolefins can be any one of the hydrogenated fractions produced by the processes described herein. These polyalphaolefins can be the hydrogenated oligomer product, the hydrogenated $\geq C_{26}$ oligomers of the oligomer product, the hydrogenated $\geq C_{19}$ oligomers of the oligomer product, the hydrogenated trimer+ oligomers of the oligomer product, a fraction formed from a fractionated and hydrogenated oligomer product (e.g., any one of the at least one hydrogenated fraction formed from a fractionated and hydrogenated oligomer product), a fraction formed from a fractionated hydrogenated oligomer product (e.g., any one of the at least one hydrogenated fraction formed from a fractionated hydrogenated oligomer product), a fraction formed from a fractionated and hydrogenated $\geq C_{19}$ oligomers of the oligomer product (e.g., any one of the at least one hydrogenated fraction formed from a fractionated and hydrogenated $\geq C_{19}$ oligomers of the oligomer product), a fraction formed from a fractionated hydrogenated $\geq C_{19}$ oligomers of the oligomer product (e.g., any one of the at least one hydrogenated fraction formed from a fractionated hydrogenated $\geq C_{19}$ oligomers of the oligomer product) a fraction formed from a fractionated and hydrogenated $\geq C_{26}$ oligomers of the oligomer product (e.g., any one of the at least one hydrogenated fraction formed from a fractionated and hydrogenated $\geq C_{26}$ oligomers of the oligomer product), a fraction formed from a fractionated hydrogenated $\geq C_{26}$ oligomers of the oligomer product (e.g., any one of the at least one hydrogenated fraction formed from a fractionated hydrogenated $\geq C_{26}$ oligomers of the oligomer product) a fraction formed from a fractionated and hydrogenated trimer+ oligomers of the oligomer product (e.g., any one of the at least one hydrogenated fraction formed from a fractionated and hydrogenated trimer+ oligomers of the oligomer product), or a fraction formed from a fractionated hydrogenated trimer+ oligomers of the oligomer product (e.g., any one of the at least one hydrogenated fraction formed from a fractionated hydrogenated trimer+ oligomers of the oligomer product).

In an embodiment, the at least one hydrogenated one or more fractions that can be formed from a fractionated and hydrogenated oligomer product, or fractionated hydrogenated oligomer product using the processes described herein can be selected from the group consisting of: a) a fraction comprising from 90 wt. % to 100 wt. % hydrogenated dimer, b) a fraction comprising 80 wt. % to 90 wt. % hydrogenated trimer and 8 wt. % to 18 wt. % hydrogenated tetramer, c) a fraction comprising 85 wt. % to 95 wt. % hydrogenated trimer and 3 wt. % to 13 wt. % hydrogenated tetramer, d) a fraction comprising 20 wt. % to 35 wt. % hydrogenated trimer, 40 wt. % to 60 wt. % hydrogenated tetramer, and 13 wt. % to 27 wt. % hydrogenated pentamer, e) a fraction comprising 35 wt. % to 55 wt. % hydrogenated trimer and 40 wt. % to 60 wt. % hydrogenated tetramer, f) a fraction comprising 45 wt. % to 65 wt. % hydrogenated tetramer, 22 wt. % to 34 wt. % hydrogenated pentamer, and 5 wt. % to 15 wt. % hydrogenated hexamer, g) a fraction comprising 12 wt. % to 24 wt. % hydrogenated trimer, 37 wt. % to 57 wt. % hydrogenated tetramer, 13 wt. % to 25 wt. % hydrogenated pentamer, and 6 wt. % to 18 wt. % hydrogenated hexamer+, h) a fraction comprising 30 wt. % to 42 wt. % hydrogenated tetramer, 27 wt. % to 39 wt. % hydrogenated pentamer, 10 wt. % to 22 wt. % hydrogenated hexamer, and 9 wt. % to 21 wt. % hydrogenated heptamer+, and i) any combination of hydrogenated fractions a) to h). In an embodiment, the at least one hydrogenated one or more fractions that can be formed from a fractionated and hydrogenated $\geq C_{19}$ oligomers of the oligomer product, or fractionated hydrogenated $\geq C_{19}$ oligomers of the oligomer product using the processes described herein can be selected from the group consisting of: a) a fraction comprising from 90 wt. % to 100 wt. % hydrogenated $C_{19}$ to $C_{22}$ oligomers, b) a fraction comprising 90 wt. % to 100 wt. % hydrogenated $C_{22}$ to $C_{26}$ oligomers, c) a fraction comprising 80 wt. % to 90 wt. % hydrogenated $C_{26}$ to $C_{34}$ oligomers and 8 wt. % to 18 wt. % hydrogenated $C_{36}$ to $C_{44}$ oligomers, d) a fraction comprising 85 wt. % to 95 wt. % hydrogenated $C_{32}$ to $C_{40}$ oligomers and 3 wt. % to 13 wt. % hydrogenated $C_{44}$ to $C_{52}$ oligomers, e) a fraction comprising 20 wt. % to 35 wt. % hydrogenated $C_{26}$ to $C_{34}$ oligomers, 40 wt. % to 60 wt. % hydrogenated $C_{36}$ to $C_{44}$ oligomers, and 13 wt. % to 27 wt. % hydrogenated $C_{46}$ to $C_{54}$ oligomers, f) a fraction comprising 35 wt. % to 55 wt. % hydrogenated $C_{32}$ to $C_{40}$ oligomers and 40 wt. % to 60 wt. % hydrogenated $C_{44}$ to $C_{52}$ oligomers, g) a fraction comprising 45 wt. % to 65 wt. % hydrogenated $C_{36}$ to $C_{44}$ oligomers, 22 wt. % to 34 wt. % hydrogenated $C_{46}$ to $C_{54}$ oligomers, and 5 wt. % to 15 wt. % hydrogenated $C_{56}$ to $C_{64}$ oligomers, h) a fraction comprising 12 wt. % to 24 wt. % hydrogenated $C_{32}$ to $C_{40}$ oligomers, 37 wt. % to 57 wt. % hydrogenated $C_{44}$ to $C_{52}$ oligomers, 13 wt. % to 25 wt. % hydrogenated $C_{56}$ to $C_{64}$ oligomers, and 6 wt. % to 18 wt. % hydrogenated $\geq C_{68}$ oligomers, i) a fraction comprising 30 wt. % to 42 wt. % hydrogenated $C_{36}$ to $C_{44}$ oligomers, 27 wt. % to 39 wt. % hydrogenated $C_{46}$ to $C_{54}$ oligomers, 10 wt. % to 22 wt. % hydrogenated $C_{56}$ to $C_{64}$ oligomers, and 9 wt. % to 21 wt. % hydrogenated $\geq C_{66}$ oligomers, and j) any combination of fractions a) to i). In an embodiment, the at least one hydrogenated one or more fractions that can be formed from a fractionated and hydrogenated ≥$C_{26}$ oligomers of the oligomer product, or fractionated hydrogenated ≥$C_{26}$ oligomers of the oligomer product using the processes described herein can be selected from the group consisting of: a) a fraction comprising 80 wt. % to 90 wt. % hydrogenated $C_{26}$ to $C_{34}$ oligomers and 8 wt. % to 18 wt. % hydrogenated $C_{26}$ to $C_{34}$ oligomers, b) a fraction comprising 85 wt. % to 95 wt. % hydrogenated $C_{32}$ to $C_{40}$ oligomers and 3 wt. % to 13 wt. % hydrogenated $C_{44}$ to $C_{52}$ oligomers, c) a fraction comprising 20 wt. % to 35 wt. % hydrogenated $C_{26}$ to $C_{34}$ oligomers, 40 wt. % to 60 wt. % hydrogenated $C_{36}$ to $C_{44}$ oligomers, and 13 wt. % to 27 wt. % hydrogenated $C_{46}$ to $C_{54}$ oligomers, d) a fraction comprising 35 wt. % to 55 wt. % hydrogenated $C_{32}$ to $C_{40}$ oligomers and 40 wt. % to 60 wt. % hydrogenated $C_{44}$ to $C_{52}$ oligomers, e) a fraction comprising 45 wt. % to 65 wt. % hydrogenated $C_{36}$ to $C_{44}$ oligomers, 22 wt. % to 34 wt. % hydrogenated $C_{46}$ to $C_{54}$ oligomers, and 5 wt. % to 15 wt. % hydrogenated $C_{56}$ to $C_{64}$ oligomers, f) a fraction comprising 12 wt. % to 24 wt. % hydrogenated $C_{32}$ to $C_{40}$ oligomers, 37 wt. % to 57 wt. % hydrogenated $C_{44}$ to $C_{52}$ oligomers, 13 wt. % to 25 wt. % hydrogenated $C_{56}$ to $C_{64}$ oligomers, and 6 wt. % to 18 wt. % hydrogenated ≥$C_{68}$ oligomers, g) a fraction comprising 30 wt. % to 42 wt. % hydrogenated $C_{36}$ to $C_{44}$ oligomers, 27 wt. % to 39 wt. % hydrogenated $C_{46}$ to $C_{54}$ oligomers, 10 wt. % to 22 wt. % hydrogenated $C_{56}$ to $C_{64}$ oligomers, and 9 wt. % to 21 wt. % hydrogenated ≥$C_{66}$ oligomers, and h) any combination of fractions a) to g). In an embodiment, the at least one hydrogenated one or more fractions that can be formed from a fractionated and hydrogenated trimer+ oligomers of the oligomer product, or fractionated hydrogenated trimer+ oligomers of the oligomer product using the processes described herein can be selected from the group consisting of: a) a fraction comprising 80 wt. % to 90 wt. % hydrogenated trimer and 8 wt. % to 18 wt. % hydrogenated tetramer, b) a fraction comprising 85 wt. % to 95 wt. % hydrogenated trimer and 3 wt. % to 13 wt. % hydrogenated tetramer, c) a fraction comprising 20 wt. % to 35 wt. % hydrogenated trimer, 40 wt. % to 60 wt. % hydrogenated tetramer, and 13 wt. % to 27 wt. % hydrogenated pentamer, d) a fraction comprising 35 wt. % to 55 wt. % hydrogenated trimer and 40 wt. % to 60 wt. % hydrogenated tetramer, e) a fraction comprising 45 wt. % to 65 wt. % hydrogenated tetramer, 22 wt. % to 34 wt. % hydrogenated pentamer, and 5 wt. % to 15 wt. % $C_{56}$ to $C_{64}$ hydrogenated hexamer, f) a fraction comprising 12 wt. % to 24 wt. % hydrogenated trimer, 37 wt. % to 57 wt. % hydrogenated tetramer, 13 wt. % to 25 wt. % hydrogenated pentamer, and 6 wt. % to 18 wt. % hydrogenated hexamer+, g) a fraction comprising 30 wt. % to 42 wt. % hydrogenated tetramer, 27 wt. % to 39 wt. % hydrogenated pentamer, 10 wt. % to 22 wt. % hydrogenated hexamer, and 9 wt. % to 21 wt. % hydrogenated heptamer+, and h) any combination fractions a) to g).

In embodiments, i) at least one of the one or more hydrogenated fractions comprising all or a portion of the ≥$C_{19}$ oligomers, ii) at least one of the one or more hydrogenated fractions comprising all or a portion of the ≥$C_{26}$ oligomers, iii) at least one of the one or more hydrogenated fractions comprising all or a portion of the hydrogenated ≥$C_{19}$ oligomers, iv) at least one of the one or more hydrogenated fractions comprising all or a portion of the hydrogenated ≥$C_{26}$ oligomers, v) at least one of the one or more hydrogenated fractions of all or a portion of the oligomer product, or vi) at least one of the one or more of the hydrogenated fractions of all or a portion of the hydrogenated oligomer product can have a 100° C. kinematic viscosity of from 1.8 cSt to 2.2 cSt, from 2.3 cSt to 2.7 cSt, from 2.6 cSt to 3.4 cSt, from 3.6 cSt to 4.4 cSt, from 4.6 cSt to 5.4 cSt, from 5.6 cSt to 6.4 cSt, from 6.6 cSt to 7.4 cSt, from 7.6 cSt to 8.4 cSt, from 8.6 cSt to 9.4 cSt, or from 9.6 cSt to 10.4 cSt.

In embodiments, i) at least one of the one or more hydrogenated fractions comprising all or a portion of the hydrogenated oligomer product, ii) at least one of the one or more hydrogenated fractions comprising all or a portion of the trimer+ oligomers, iii) at least one of the one or more hydrogenated fractions comprising all or a portion of the hydrogenated oligomer product, iv) at least one of the one or more hydrogenated fractions comprising all or a portion of hydrogenated trimer+ oligomers, v) at least one of the one or more hydrogenated fractions of all or a portion of the oligomer product, or vi) at least one of the one or more hydrogenated fractions of all or a portion of the hydrogenated oligomer product of E130 can have a 100° C. kinematic viscosity of from 1.8 cSt to 2.2 cSt, from 2.3 cSt to 2.7 cSt, from 2.6 cSt to 3.4 cSt, from 3.6 cSt to 4.4 cSt, from 4.6 cSt to 5.4 cSt, from 5.6 cSt to 6.4 cSt, from 6.6 cSt to 7.4 cSt, from 7.6 cSt to 8.4 cSt, from 8.6 cSt to 9.4 cSt, or from 9.6 cSt to 10.4 cSt.

In an embodiment, any polyalphaolefin produced by a process described herein can have a 100° C. kinematic viscosity from 1.5 cSt to 50 cSt; alternatively, from 1.5 cSt to 30 cSt; alternatively, from 1.5 cSt to 20 cSt; alternatively, from 1.5 cSt to 10 cSt. In other embodiments, any polyalphaolefin produced by a process described herein can have a 100° C. kinematic viscosity of about 2 cSt, about 2.5 cSt, about 4 cSt, about 5 cSt, about 6 cSt, about 7 cSt, about 8 cSt, or about 9 cSt. Generally, the kinematic viscosity can be measured using ASTM D445-12 or ASTM D7042-12a.

In an embodiment, polyalphaolefin produced by a process described herein can have minimum viscosity index of 100, 110, 120, 130, 140 or 150. In other embodiments, any polyalphaolefin produced by a process described herein can have viscosity index ranging from 100 to 250, from 110 to 225, or from 120 to 200. The viscosity index is a measure of the variation in kinematic viscosity of a product due to changes in the temperature between 40° C. and 100° C. Generally, the viscosity index can be measured according to ASTM D2270-10e1.

In an embodiment, any polyalphaolefin produced by a process described herein can have a pour point less than or equal to −20° C., −30° C., −35° C., −40° C., −45° C., or −50° C. Any polyalphaolefin produced by a process described herein can have a pour point from −20° C. to −100° C., alternatively, from −25° C. to −95° C., alternatively, from −30° C. to −90° C.; or alternatively, from −35° C. to −85° C. Generally, the pour point can be measured using ASTM D97-12.

In an embodiment, any polyalphaolefin produced by a process described herein can have a maximum bromine number of 2, 1.8, 1.6, 1.4, 1.2, or 1 as determined by ASTM D1159-09 and has units of grams bromine per 100 grams of sample (g Br/100 g). In other embodiments, polyalphaolefin produced by a process described herein can have a maximum bromine index of 1000, 800, 600, or 500 as determined by ASTM D2710-09 and has units of milligrams bromine per 100 grams of sample (mg Br/100 g).

In an embodiment, any polyalphaolefin produced by a process described herein can be subjected to processes to reduce the amount of heteroatom containing compounds to acceptable levels for the desired polyalphaolefin use. In some embodiments, the polyalphaolefin having a reduced amount of heteroatom containing compounds can contain a maximum of 600 ppmw, 300 ppmw, 100 ppmw, 50 ppmw, 10 ppmw, 5 ppmw, or 1 ppmw of heteroatom containing compounds. In an embodiment, the heteroatomic compounds whose presence can be reduced in the polyalphaolefin can include halogen containing compounds such as organic and/or inorganic fluorides, chlorides, bromides, or iodides.

In an aspect, the polyalphaolefin produced by a process described herein can be further used in a variety of components or products for a diverse range of applications and industries. For example, the polyalphaolefin can be utilized as a lubricant base oil (or a component of a lubricant base oil) for lubricant compositions and/or functional fluid compositions. Exemplary lubricant compositions in which the polyalphaolefins produced by the processes described herein can be utilized include, but are not limited to, greases, gearbox oils, engine oils, transmission fluids, and/or drilling fluids. Exemplary functional fluid compositions in which the polyalphaolefins produced by the processes described herein can be utilized include, but are not limited to, hydraulic fluids, drilling fluids, coolant fluids, and/or dielectric coolant fluids. In an aspect, the polyalphaolefin produced by a processes described herein can be utilized as the sole Base Oil for a lubricant composition and/or functional fluid composition. In other aspects, the polyalphaolefin produced by a process described herein can be combined with one or more other Base Oils to form a Base Oil for a lubricant composition and/or functional fluid composition. In an embodiment, the polyalphaolefin produced by a processes described herein can be blended with a Group I Base Oil, Group II Base Oil, Group III Base Oil, another Group IV Base Oil, a Group V Base Oil, or any combination of thereof to form a lubricant base oil for lubricant compositions and/or functional fluid compositions. As utilized herein, the Base Oil groups are those as designated by The American Petroleum Institute (API). Additional information on the use of polyalphaolefin in lubricant compositions and/or functional fluid compositions can be found in "Synthetic Lubricants and High-Performance Functional Fluids," 2nd Ed., L. Rudnick, ed., Marcel Dekker, Inc., NY (1999). Additional information on additives used in product formulation can be found in "Lubricants and Lubrications," T. Mang and W. Dresel, eds., Wiley-VCH GmbH, Weinheim (2001).

Fully formulated lubricants can further include one or more additives. Additives which can be include in a fully formulated lubricant can include but are not limited to viscosity index improvers/viscosity modifiers/viscosity improver, dispersants (metallic and/or non-metallic), detergents (metallic and/or non-metallic), friction modifiers, traction improving additives, demulsifiers, defoamants, antioxidants, anti-wear additives (metallic and non-metallic, phosphorus-containing and non-phosphorus, sulfur-containing and non-sulfur types), extreme-pressure additives (metallic and non-metallic, phosphorus-containing and non-phosphorus, sulfur-containing and non-sulfur types), anti-rust additives, corrosion inhibitors, metal deactivators, anti-seizure agents, pour point depressants, wax modifiers, seal compatibility agents, friction modifiers, lubricity agents, anti-staining agents, chromophores (dyes), and/or haze inhibitors. Additional information on additives used in product formulations can be found in "Fuels and Lubricants Handbook: Technology, Properties, Performance, and Testing" edited by George E. Totten, Steven R. Westbrook, Rajesh J. Shah, ASTM (2003), ISBN 0-8031-2096-6; Chapter 9 Additives and Additive Chemistry, pp. 199-248, "Lubricants and Related Products," Klamann, Verlag Chemie, Deerfield Beach, Fla., ISBN 0-89573-177-0; "Lubricant Additives" by M. W. Ranney, published by Noyes Data Corporation of Parkridge, N.J. (1973); "Lubricants and Lubrications," T. Mang and W. Dresel, eds., Wiley-VCH GmbH, Weinheim (2001); and "Lubricant Additives", C. V. Smallheer and R. K. Smith, published by the Lezius-Hiles Co. of Cleveland, Ohio (1967).

Viscosity index improvers (also known as viscosity modifiers and viscosity improvers) can provide lubricant compositions and/or functional fluid compositions with high and low temperature operability. These additives can impart shear stability at elevated temperatures and acceptable viscosity at low temperatures. Suitable viscosity index improvers can include high molecular weight hydrocarbons, olefin polymers and copolymers, polyesters, and viscosity index improver dispersants that function as both a viscosity index improver and a dispersant. Viscosity index improvers can have molecular weights ranging from about 10,000 Da to about 1,000,000 Da, from about 20,000 Da to about 500,000 Da, or from about 50,000 Da to about 200,000 Da.

Viscosity index improvers can include polymers and copolymers of methacrylate, butadiene, olefins, or alkylated styrenes. Exemplary viscosity index improvers include, but are not limited to, polyisobutylene, copolymers of ethylene and propylene, hydrogenated block copolymers of styrene and isoprene, polyacrylates (e.g., polymers and/or copolymers of various chain length acrylates), and polymethacrylates (e.g., polymer and/or copolymers of various chain length alkyl methacrylates. Generally, the viscosity index improver can be used in an amount of from 0.01 wt. % to 6 wt. %, from 0.01 to 5 wt. %, or from 0.01 to 4 wt. % based upon the total weight of the composition.

Dispersants are additives utilized to maintain oxidation products (produced during use of the lubricant composition) in suspension in the lubricant compositions and/or functional fluid compositions to prevent the accumulation of debris that could score bearings, block lubricant pathways, prevent deposit formations, inhibit corrosive wear by neutralizing acidic products (e.g., combustion products), and other types of damage. Dispersants can be ash-containing or ashless in character. Dispersants can include, but are not limited to alkenylsuccinic acid or anhydride derivatives (e.g., succinimides, succinate esters, or succinate ester amides), phenates, Mannich-Base condensates (e.g., the condensation products of alkylphenols, amines and aldehydes), hydrocarbyl substituted amines, sulfonates, sulfurized phenates, salicylates, naphthenates, stearates, carbamates, thiocarbamates, and phosphorus derivatives in metallic and non-metallic versions. Suitable dispersants can contain a polar group attached to a relatively high molecular weight hydrocarbon chain where the polar group contains at least one element of nitrogen, oxygen, or phosphorus. Patents describing dispersants which can be utilized in the lubricant compositions and/or functional fluid compositions include, but are not limited to, U.S. Pat. Nos. 3,036,003; 3,087,936; 3,172,892; 3,200,107; 3,215,707; 3,219,666; 3,254,025; 3,272,746; 3,275,554; 3,322,670; 3,329,658; 3,316,177; 3,438,757; 3,341,542; 3,413,347; 3,444,170; 3,449,250; 3,454,555; 3,454,607; 3,519,565; 3,541,012; 3,565,804; 3,630,904; 3,632,511; 3,652,616; 3,666,730; 3,687,849; 3,697,574; 3,702,300; 3,703,536; 3,704,308; 3,725,277; 3,725,480; 3,726,882; 3,751,365; 3,755,433; 3,756,953; 3,787,374; 3,798,165; 3,803,039; 3,822,209; 3,948,800; 4,100,082; 4,234,435; 4,426,305; 4,454,059; 4,767,551; and 5,705,458, among others. Generally, dispersants can be used in an amount of about 0.1 wt. % to 20 wt. %, 0.1 wt. % to 15 wt. %, or from 0.1 wt. % to 8 wt. % based upon the total weight of the composition.

Detergents are additives utilized to maintain overall cleanliness by keeping sludge, carbon and deposit precursors suspended in the lubricant compositions and/or functional fluid compositions. Many detergents are chemically similar to dispersants. Detergents which can be utilized in the lubricant compositions and/or functional fluid compositions can include the alkali or alkaline earth metal of sulfates, sulfonates, phenates, carboxylates, phosphates, carboxylic acids, and salicylates. For example, suitable detergents can include, but are not limited to, the sulfonated alkylaromatic hydrocarbons, alkyl phenols, sulfurized alkyl phenols treated with an alkaline earth metal hydroxide or oxide (e.g., CaO, Ca(OH)$_2$, BaO, Ba(OH)$_2$, MgO, or Mg(OH)$_2$). Sulfonated alkylaromatic compounds can be prepared from sulfonic acids obtained by sulfonation of $C_9$ to $C_{80}$ (or $C_6$ to $C_{60}$) alkyl substituted aromatic hydrocarbons (having one or more than one alkyl groups) where the alkyl groups independently can be $C_3$ to $C_{70}$ alkyl groups and the aromatic portion can be benzene, toluene, xylene, naphthalene, or biphenyl. Alkyl phenol and/or sulfurized alkyl phenols can have one or more $C_4$ to $C_{30}$ alkyl groups. The detergents utilized in the lubricant compositions and/or functional fluid compositions can be neutral (i.e., produced using only enough alkali or alkaline earth compound to neutralize the sulfonated alkylaromatic compound, alkyl phenol, or sulfurized alkyl phenol) or can be overbased (i.e., produced using more alkali or alkaline earth compound than necessary to neutralize the sulfonated alkylaromatic compound, alkyl phenol, or sulfurized alkyl phenol). Generally, detergents can be used in an amount of 0.01 wt. % to 6.0 wt. %, 0.05 wt. % to 5.0 wt. %, or 0.1 to 4 wt. % based upon the total weight of the composition.

Defoamants (or anti-foam agents) are additives utilized to retard the formation of stable foam in the lubricant compositions and/or functional fluid compositions. Defoamants which can be utilized in the lubricant compositions and/or functional fluid compositions can include, but are not limited to, silicone compounds (e.g., polysiloxanes, such as silicon oil or polydimethyl siloxane, among others) and organic polymers. Defoamants can be utilized in conjunction with demulsifiers. Generally, the maximum amount of defoamants can be in an amount of 1 wt. %, 0.5 wt. % or 0.1 wt. % based upon the total weight of the composition.

Antioxidants are additives utilized to retard the oxidative degradation of the base oil(s) in the lubricant compositions and/or functional fluid compositions. Oxidative base oil degradation can produce deposits on metal surfaces, sludge, and/or increase the viscosity of the lubricant composition. Antioxidants which can be utilized in the lubricant compositions and/or functional fluid compositions include, but are not limited to, hindered phenols (ashless); neutral or basic metal salts of hindered phenols; hindered phenolic carboxylic acid (e.g., propionic acid) ester derivatives; bis-hindered phenols; alkylated and non-alkylated aromatic amines; sulfurized alkyl phenols; alkali or alkaline earth metal salts of sulfurized alkyl phenols; copper dihydrocarbyl thio or dithio-phosphates; copper salts of carboxylic acids (natural or synthetic); and copper salts of dithiacarbamates, dithiocarbamates, sulphonates, phenates, acetylacetonates and alkenyl succinic acids or anhydrides (neutral, basic or acidic). Patents describing antioxidants which can be utilized in the lubricant compositions and/or functional fluid compositions include, but are not limited to, U.S. Pat. Nos. 4,798,684 and 5,084,197. Generally, the antioxidants can be used in an amount of from 0.01 wt. % to 5 wt. %, from 0.01 to 2.5 wt. %, or from 0.01 wt. % to 1.5 wt. % based upon the total weight of the composition.

Anti-wear additives and extreme pressure additives are compounds utilized to reduce friction and wear of metal parts of the base oil(s) in the lubricant compositions and/or functional fluid compositions. Anti-wear additives and extreme pressure additives which can be utilized in the lubricant compositions and/or functional fluid compositions include, but are not limited to, metal alkylthiophosphates (e.g., a zinc alkylthiophosphonate having a $C_1$ to $C_{18}$ alkyl group), metal dialkyldithiophosphates (e.g., a zinc alkylthiophosphonate having $C_1$ to $C_{18}$ alkyl groups), sulfurized $C_3$ to $C_{30}$ aliphatic or arylaliphatic hydrocarbon olefins (acyclic or cyclic), polysulfides of thiophosphorus acids, polysulfides of thiophosphorus acid esters, phosphorothionyl disulfides, alkylthiocarbamoyl compounds (e.g., bis(dibutyl)thiocarbamoyl) in combination with a molybdenum compound (e.g., oxymolybdenum diisopropylphosphorodithioate sulfide) and phosphorus ester (e.g., dibutyl hydrogen phosphite, for example), thiocarbamates, thiocarbamate/molybdenum complexes (e.g., moly-sulfur alkyl dithiocarbamate trimer complexes), and/or glycerol ester (e.g., mono-, di-, and tri-oleates, mono-palmitates and mono-myristates). Patents describing anti-wear additives and/or extreme pressure additives which can be utilized in the lubricant compositions and/or functional fluid compositions include, but are not limited to, U.S. Pat. Nos. 2,443,264; 2,471,115; 2,526,497; 2,591,577; 3,770,854; 4,501,678; 4,941,984; 5,034,141; 5,034,142; 5,084,197; and 5,693,598. Generally, the total amount of anti-wear additives and extreme pressure additives used in the lubricant compositions and/or functional fluid compositions can be in an amount of from 0.01 wt. % to 6 wt. %, from 0.01 to 5 wt. %, or from 0.01 wt. % to 4 wt. % based upon the total weight of the composition.

Anti-rust additives are additives that protect lubricated metal surfaces against chemical attack by water or other contaminants. Anti-rust additives can function by 1) wetting the metal surface with a film of oil, 2) absorbing water into a water-in-oil emulsion, and/or 3) adhering to the metal to form a non-reactive surface, among other potential modes of function. Anti-rust additives which can be utilized in the lubricant compositions and/or functional fluid compositions include, but are not limited to, zinc dithiophosphates, metal phenolates, basic metal sulfonates, fatty acids, and amines. Generally, the amount of anti-rust additives used in the lubricant compositions and/or functional fluid compositions can be in an amount of from 0.01 wt. % to 5 wt. %, from 0.01 wt. % to 2.5 wt. %, or from 0.01 wt. % to 1.5 wt. % based upon the total weight of the composition.

Corrosion inhibitors are additives that reduce the degradation of metallic parts that are in contact with the lubricant compositions and/or functional fluid compositions. Corrosion inhibitors which can be utilized in the lubricant compositions and/or functional fluid compositions include, but are not limited to, thiadiazoles and triazoles. Patents describing corrosion inhibitors which can be utilized in the lubricant compositions and/or functional fluid compositions include, but are not limited to, U.S. Pat. Nos. 2,719,125; 2,719,126; and 3,087,932. Generally, the amount of corrosion inhibitors used in the lubricant compositions and/or functional fluid compositions can be in an amount of from 0.01 wt. % to 5 wt. %, from 0.01 wt. % to 2.5 wt. %, or from 0.01 wt. % to 1.5 wt. % based upon the total weight of the composition.

Pour point depressants are additives that reduce the minimum temperature at which the lubricant compositions and/or functional fluid compositions will flow or can be poured. Pour point depressants which can be utilized in the lubricant compositions and/or functional fluid compositions include, but are not limited to, polymethacrylates, polyacrylates, polyarylamides, condensation products of haloparaffin waxes and aromatic compounds, vinyl carboxylate polymers, and terpolymers of dialkylfumarates, vinyl esters of fatty acids and allyl vinyl ethers. Patents describing pour point depressants which can be utilized in the lubricant compositions and/or functional fluid compositions include, but are not limited to, U.S. Pat. Nos. 1,815,022; 2,015,748; 2,191,498; 2,387,501; 2,655,479; 2,666,746; 2,721,877; 2,721,878; and 3,250,715. Generally, the amount of pour point depressant used in the lubricant compositions and/or functional fluid compositions can be in an amount of from 0.01 wt. % to 5 wt. %, from 0.01 wt. % to 2.5 wt. %, or from 0.01 wt. % to 1.5 wt. % based upon the total weight of the composition.

Seal compatibility additives are compounds that swell elastomeric seals and can function by causing a chemical reaction in the fluid or a physical change in the seal elastomer. Seal compatibility additives which can be utilized in the lubricant compositions and/or functional fluid compositions include, but are not limited to, organic phosphates, aromatic esters, aromatic hydrocarbons, esters (e.g., butylbenzyl phthalate), and polybutenyl succinic anhydride. Generally, the amount of seal compatibility additive used in the lubricant composition and/or functional fluid compositions can be in an amount of from 0.01 wt. % to 3 wt. %, from 0.01 wt. % to 2.5 wt. %, or from 0.01 wt. % to 2 wt. % based upon the total weight of the composition.

For the purpose of any U.S. national stage filing from this application, all publications and patents mentioned in this disclosure are incorporated herein by reference in their entireties, for the purpose of describing and disclosing the constructs and methodologies described in those publications, which might be used in connection with the methods of this disclosure. Any publications and patents discussed herein are provided solely for their disclosure prior to the filing date of the present application. Nothing herein is to be construed as an admission that the inventors are not entitled to antedate such disclosure by virtue of prior invention.

In any application before the United States Patent and Trademark Office, the Abstract of this application is provided for the purpose of satisfying the requirements of 37 C.F.R. § 1.72 and the purpose stated in 37 C.F.R. § 1.72(b) "to enable the United States Patent and Trademark Office and the public generally to determine quickly from a cursory inspection the nature and gist of the technical disclosure." Therefore, the Abstract of this application is not intended to be used to construe the scope of the claims or to limit the scope of the subject matter that is disclosed herein. Moreover, any headings that can be employed herein are also not intended to be used to construe the scope of the claims or to limit the scope of the subject matter that is disclosed herein. Any use of the past tense to describe an example otherwise indicated as constructive or prophetic is not intended to reflect that the constructive or prophetic example has actually been carried out.

The present disclosure is further illustrated by the following examples, which are not to be construed in any way as imposing limitations upon the scope thereof. On the contrary, it is to be clearly understood that resort can be had to various other aspects, embodiments, modifications, and equivalents thereof which, after reading the description herein, can be suggest to one of ordinary skill in the art without departing from the spirit of the present invention or the scope of the appended claims.

EXAMPLES

The N-(n-butyl)pyridinium chloroaluminate ($C_5H_5NC_4H_9Al_2Cl_7$) was prepared as described in Example 1 of U.S. Pat. No. 7,572,944 and then stored under an inert atmosphere.

1-Decene was obtained from Chevron Phillips Chemical Company, LP, dried over molecular sieves (typically 13X or 3A) for at least one hour and stored under an inert atmosphere.

Tert-butyl chloride was obtained from Sigma-Aldrich and was degassed prior to use.

Hydrogen chloride gas was obtained from Matheson Tri-Gas and utilized as obtained.

Examples 1 to 5

In Examples 1 to 3, 1-decene was oligomerized in the presence of an ionic liquid and without the presence of a halide component (thus, referred to as comparative Examples 1 to 3). In Examples 4 to 5, 1-decene was oligomerized in the presence of an ionic liquid and in the presence of a halide component. In each of Examples 1 to 5, the ionic liquid was N-(n-butyl)pyridinium chloroaluminate ($C_5H_5NC_4H_9Al_2Cl_7$). In Examples 4 to 5, the halide component was tert-butyl chloride.

In each of Examples 1 to 5, a 600 mL Hastelloy®-C autoclave having internal cooling coils was used as the reaction zone. In an inert atmosphere dry box, the previously dried Hastelloy®-C autoclave was charged with 1-decene and the halide component, tert-butyl chloride, (Examples 4 and 5) and sealed. In an inert atmosphere dry box, a previously dried 50 mL stainless steel sample cylinder was charged with the ionic liquid N-(n-butyl)pyridinium chloroaluminate. The sealed Hastelloy®-C autoclave and stainless steel sample cylinder were removed from the dry box whereupon the stainless steel sample cylinder was attached to the autoclave. The contents of the autoclave were stirred at 1200 rpm allowed to come to the desired reaction temperature using an external heating jacket and/or internal cooling coils as necessary. The ionic liquid N-(n-butyl)pyridinium chloroaluminate was then injected into the autoclave using $N_2$ at a pressure of 50 psig greater than the reactor pressure. The reaction temperature was maintained, under stirring, using the external heating jacket and/or internal cooling coils as necessary for 1 hour. After an hour, the contents of the autoclave were collected in a separatory funnel and allowed to settle for 1 hour. The top, hydrocarbon layer was collected and washed with deionized water to remove traces on the ionic liquid. The hydrocarbon products were dried over anhydrous magnesium sulfate ($MgSO_4$) and filtered. The hydrocarbon phase was analyzed by Simulated Distillation Gas Chromatography, SimDist, using ASTM D6417. Table 1-1 provides the reaction conditions for Examples 1 to 5. Table 1-2 provides oligomerization results for Examples 1 to 5. Table 1-3 provides values describing the oligomer distribution of the oligomer product produced in oligomerization Examples 1 to 5 using the Simulated Distillation Gas Chromatography Data.

TABLE 1-1

| Examples 1 to 5, Reaction Conditions | | | | | |
|---|---|---|---|---|---|
| | Example 1 | Example 2 | Example 3 | Example 4 | Example 5 |
| 1-Decene (mL) | 500 | 500 | 500 | 500 | 500 |
| Ionic Liquid (mL) | 10.2 | 10.2 | 10.2 | 10.2 | 10.2 |
| Halide Component (mL) | — | — | — | 0.5 | 0.1 |

TABLE 1-1-continued

Examples 1 to 5, Reaction Conditions

| | Example 1 | Example 2 | Example 3 | Example 4 | Example 5 |
|---|---|---|---|---|---|
| Diluent (mL) | — | — | — | — | — |
| Ionic Liquid (vol %) | 2 | 2 | 2 | 2 | 2 |
| Halide Component (vol % of ionic liquid) | — | — | — | 4.9 | 1.0 |
| Double Bonds in Monomer to Al in Ionic Liquid Molar Ratio | 43.2 | 43.2 | 43.2 | 43.2 | 43.2 |
| Cl in Halide Component to Al in Ionic Liquid Molar Ratio | — | — | — | 0.0754 | 0.0151 |
| Conversion (%) | 100.0 | 99.8 | 99.2 | 99.2 | 99.7 |
| Reaction Time (min) | 60 | 60 | 60 | 60 | 60 |
| Reaction Temperature (° C.) | 20 | 50 | 95 | 20 | 95 |

TABLE 1-2

Examples 1 to 5, Molecular Weight Distribution of Unreacted Monomer and the Oligomer Product

| Distribution (wt. %) | Example 1 | Example 2 | Example 3 | Example 4 | Example 5 |
|---|---|---|---|---|---|
| $C_{10}$ | 0.1 | 0.2 | 0.8 | 0.7 | 0.3 |
| $C_{20}$ | 1.2 | 1.4 | 12.9 | 15.5 | 10.8 |
| $C_{30}$ | 3.5 | 5.0 | 16.7 | 22.4 | 21.2 |
| $C_{40}$ | 4.3 | 5.7 | 15.3 | 14.4 | 17.5 |
| $C_{50}$ | 8.3 | 10.3 | 15.5 | 14.1 | 16.5 |
| $C_{60}$ | 11.4 | 12.3 | 13.4 | 12.1 | 13.5 |
| $C_{70+}$ | 71.3 | 65.1 | 25.4 | 20.7 | 20.2 |
| Conversion (%) | 100.0 | 99.8 | 99.2 | 99.2 | 99.7 |

TABLE 1-3

Examples 1 to 5, Molecular Weight Distribution Data of the Oligomer Product

| Distribution (wt. %) | Example 1 | Example 2 | Example 3 | Example 4 | Example 5 |
|---|---|---|---|---|---|
| $C_{20}$ | 1.20 | 1.40 | 13.00 | 15.63 | 10.83 |
| $C_{30}$ | 3.50 | 5.01 | 16.83 | 22.58 | 21.26 |
| $C_{40}$ | 4.30 | 5.71 | 15.42 | 14.52 | 17.55 |
| $C_{50}$ | 8.30 | 10.32 | 15.63 | 14.21 | 16.55 |
| $C_{60}$ | 11.40 | 12.32 | 13.51 | 12.20 | 13.54 |
| $C_{70+}$ | 71.30 | 65.23 | 25.60 | 20.87 | 20.26 |
| $C_{20}$-$C_{50}$ | 17.30 | 22.44 | 60.89 | 66.94 | 66.20 |
| $C_{30}$-$C_{50}$ | 16.10 | 21.04 | 47.88 | 51.31 | 55.37 |
| $C_{20}$-$C_{40}$ | 9.00 | 12.12 | 45.26 | 52.72 | 49.65 |
| $C_{30}$-$C_{40}$ | 7.80 | 10.72 | 32.26 | 37.10 | 38.82 |
| $C_{50+}$ | 91.00 | 87.88 | 54.74 | 47.28 | 50.35 |
| $C_{60+}$ | 82.70 | 77.56 | 39.11 | 33.06 | 33.80 |
| Average Mn (g/mol) | >897 | >874 | >669 | >628 | >648 |

Examples 1 to 5 indicate that oligomerization of 1-decene with N-(n-butyl)pyridinium chloroaluminate in the absence of a halide component at temperatures ranging from 20° C. to 95° C. produce a very heavy oligomer distribution that is heavier than the oligomer distribution produced using the halide component and an ionic liquid at a comparable temperature. For example the average Mn of the oligomer product produced at 20° C. in the absence of the halide component is >897 g/mole (Example 1) while the use of the halide component produced an oligomer product having an average Mn>628 g/mol (Example 4). Examples 1-5 show that the use of a halide component can be utilized to lower the average molecular weight of an oligomer product produced using an ionic liquid catalyst system.

Examples 6 to 9

Example 6

Comparative

For Example 6, ionic liquid N-(n-butyl)pyridinium chloroaluminate ($C_5H_5NC_4H_9Al_2Cl_7$) was prepared as described in Example 1 of U.S. Pat. No. 7,572,944 and then stored under an inert atmosphere. The N-(n-butyl)pyridinium chloroaluminate ($C_5H_5NC_4H_9Al_2Cl_7$) had the elemental composition provided in Table 6-1.

TABLE 6-1

N-(n-butyl)pyridinium chloroaluminate composition

| Element | wt. % |
|---|---|
| Al | 12.4 |
| Cl | 56.5 |
| C | 24.6 |
| H | 3.2 |
| N | 3.3 |

Under a blanket of nitrogen, a 300 mL jacketed glass reactor equipped with an overhead stirrer (used as the reaction zone) was charged with 280 mL (207.2 g) of 1-decene and maintained under a blanket of nitrogen. Water having a temperature of 20° C. was circulated through the jacket of the jacketed glass reactor and 1-decene was stirred at 1,000 rpm for 30 minutes to allow to the 1-decene to reach thermal equilibrium. A volume of 7 mL (9.1 g) of N-(n-butyl)pyridinium chloroaluminate was added to the 1-decene in the reactor by syringe. After a reaction time of 80 minutes at a reaction temperature of 20° C., 50 mL of reaction mixture was removed from the reactor (equivalent to a reaction zone effluent for a continuous reactor). The removed reaction mixture was treated via quenching with 50 mL of deionized water. The hydrocarbon layer of treated product formed and was collected. The treated product was dried over anhydrous magnesium sulfate ($MgSO_4$) and filtered to yield unreacted monomer and the oligomer product for analysis. The hydrocarbon phase was analyzed by Simulated Distillation Gas Chromatography, SimDist, using ASTM D6417. Table 6-2 provides the reaction conditions for Example 6. Table 6-3 provides the SimDist Data from the hydrocarbon phase isolated from the reaction effluent of Example 6.

Example 7

Comparative

Example 7 represents a reproduction, not a repeated experiment, of the oligomerization of 1-decene using the ionic liquid 1-methyl-tributyl ammonium chloroaluminate and halide component HCl disclosed in Example 2 of U.S. Pat. No. 7,572,944. Table 6-2 provides the reaction conditions for Example 7 (i.e., Example 2 of U.S. Pat. No. 7,572,944). Table 6-3 provides the SimDist Data for Example 7 (i.e., SimDist data taken from Table 1 for Example 2 of U.S. Pat. No. 7,572,944).

Example 8

Under a blanket of nitrogen, a 300 mL jacketed glass reactor equipped with an overhead stirrer (used as the reaction zone) was charged with 280 mL (207.2 g) of 1-decene and 2.5 mL (2.1 g) of tert-butyl chloride. Water having a temperature of 20° C. was circulated through the jacket of the jacketed glass reactor and 1-decene was stirred at 1,000 rpm for 30 minutes to allow to the 1-decene to reach thermal equilibrium. A volume of 7 mL (9.1 g) of N-(n-butyl)pyridinium chloroaluminate (as described in Example 6) was added to the 1-decene in the reactor by syringe. After a reaction time of 80 minutes at a reaction temperature of 20° C., 50 mL of reaction mixture was removed from the reactor (equivalent to a reaction zone effluent for a continuous reactor). The removed reaction mixture was treated via quenching with 50 mL of deionized water. The hydrocarbon layer of treated product formed and was collected. The treated product was dried over anhydrous magnesium sulfate ($MgSO_4$) and filtered to yield unreacted monomer and the oligomer product for analysis. The hydrocarbon phase was analyzed by Simulated Distillation Gas Chromatography, SimDist, using ASTM D6417. Table 6-2 provides the reaction conditions for Example 6. Table 6-3 provides the SimDist Data from the hydrocarbon phase isolated from the reaction effluent of Example 6.

Example 9

In an inert atmosphere dry box, a previously dried Hastelloy®-C autoclave was charged with 500 mL, 371 grams, 1-decene and 1 mL, 0.84 grams, tert-butyl chloride and sealed. In an inert atmosphere dry box, a previously dried 50 mL stainless steel sample cylinder was charged with 10 mL the ionic liquid N-(n-butyl)pyridinium chloroaluminate. The sealed Hastelloy®-C autoclave and stainless steel sample cylinder were removed from the dry box whereupon the stainless steel sample cylinder was attached to the autoclave. The contents of the autoclave was stirred at 1200 rpm allowed to come to 130° C. and equilibrate for 30 minutes, using an external heating jacket and/or internal cooling coils as necessary. The ionic liquid N-(n-butyl)pyridinium chloroaluminate was then injected into the autoclave using $N_2$ at a pressure of 50 psig greater than the reactor pressure. The reaction temperature of 130° C. was maintained, under stirring, using the external heating jacket and/or internal cooling coils as necessary for 1 hour. After an hour, the contents of the autoclave were collected in a separator funnel and allowed to settle for 1 hour. The top, hydrocarbon layer was collected and washed with deionized water to remove traces on the ionic liquid catalyst system. The hydrocarbon products were dried over anhydrous magnesium sulfate ($MgSO_4$) and filtered. The hydrocarbon phase was analyzed by Simulated Distillation Gas Chromatography, SimDist, using ASTM D6417. Table 6-2 provides the reaction conditions for Example 9. Table 6-3 provides the SimDist Data from the hydrocarbon phase isolated from the reaction effluent of Example 9.

TABLE 6-2

Examples 6 to 9, Reaction Conditions

|  | Example 6 | Example 7 | Example 8 | Example 9 |
|---|---|---|---|---|
| 1-Decene (g) | 207 | 100 | 207 | 371 |
| Ionic Liquid (g) | 9.1 | 20 | 9.1 | 13 |
| Halide Component (g) | — | 0.35 | 2.1 | 0.84 |
| Ionic Liquid (vol %) | 2.44 | 10.2 | 2.44 | 1.96 |
| Halide Component (vol % of ionic liquid) | — | — | 30 | 8.4 |
| Double Bonds in Monomer to Al in Ionic Liquid Molar Ratio | 35.2 | 8.9 | 35.2 | 44.1 |
| Cl in Halide Component to Al in Ionic Liquid Molar Ratio | — | 0.12 | 0.54 | 0.15 |
| Reaction Time (min) | 80 | 60 | 80 | 60 |
| Reaction Temperature (° C.) | 20 | 50 | 20 | 130 |

TABLE 6-3

Examples 6 to 9, SimDist True-Boiling Point (TBP) Data of the Unreacted Monomer and Oligomer Product

| | Temperature (° F.) | | | |
|---|---|---|---|---|
| | Example 6 | Example 7 | Example 8 | Example 9 |
| Initial Boiling Point (IBP) | 390 | 330 | 311 | 320 |
| TBP at 5 wt. % | 906 | 608 | 345 | 342 |
| TBP at 10 wt. % | 991 | 764 | 596 | 345 |
| TBP at 15 wt. % | 1042 | 789 | 616 | 420 |
| TBP at 20 wt. % | 1073 | 856 | 637 | 598 |
| TBP at 30 wt. % | 1120 | 944 | 784 | 626 |
| TBP at 40 wt. % | 1158 | 1018 | 806 | 764 |
| TBP at 50 wt. % | 1191 | 1053 | 902 | 802 |
| TBP at 60 wt. % | 1128 | 1140 | 971 | 900 |
| TBP at 70 wt. % | 1291 | 1192 | 1026 | 980 |
| TBP at 80 wt. % | — | 1250 | 1094 | 1054 |
| TBP at 90 wt. % | — | 1311 | 1179 | 1143 |
| TBP at 95 wt. % | — | 1340 | 1255 | 1218 |
| TBP at 99.5 wt. % | — | 1371 | 1355 | |
| Recovery at 1335° F., wt. % | 75 | | 98 | 98 |

Figure 5:
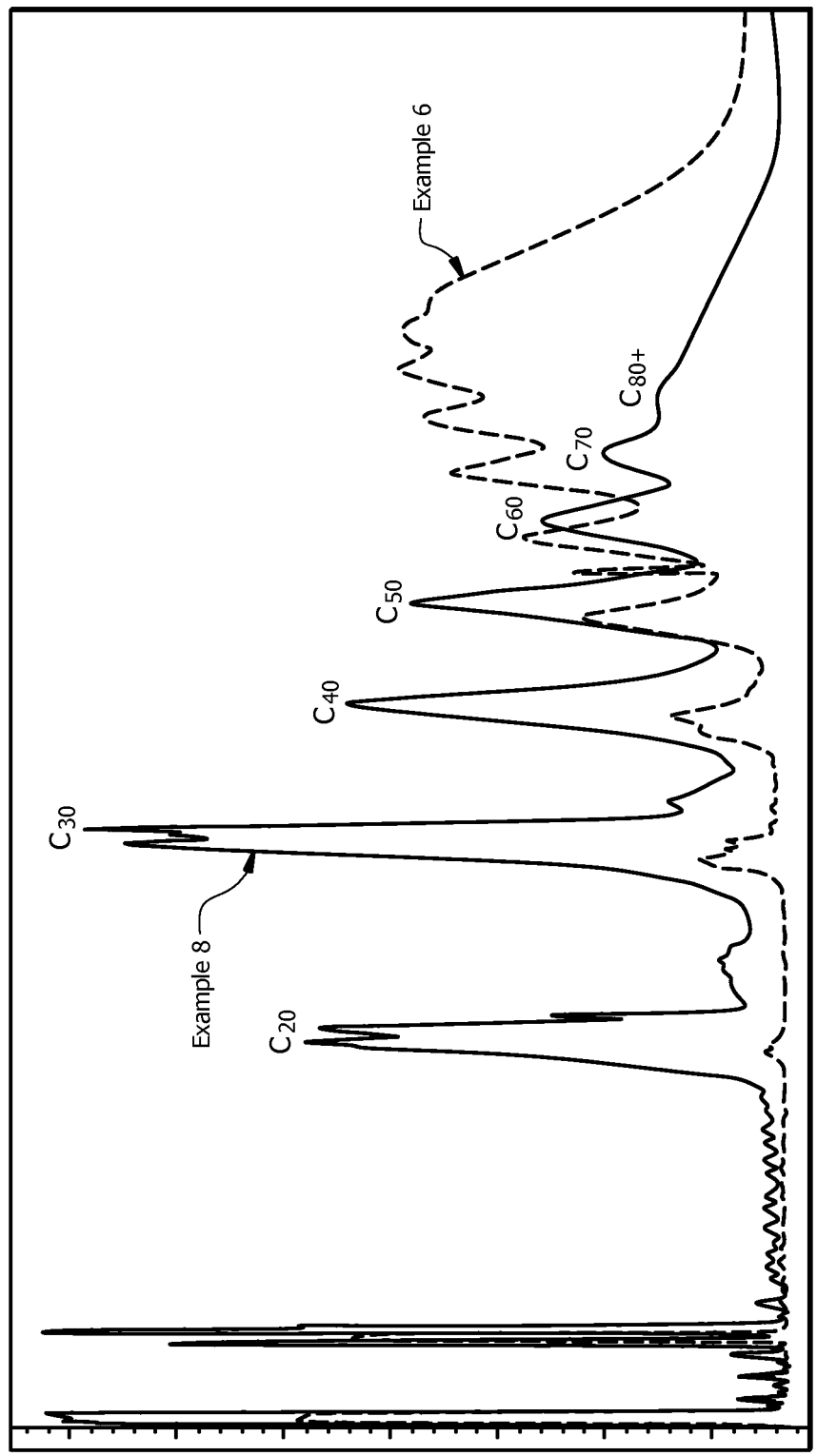
FIG. 5 shows the overlaid gas chromatography chromatograms of Examples 6 and 8.

The SimDist data for Examples 6 to 9 indicate that the absence of a halide component (Example 6) results in a significantly heavier oligomer distribution than produced when the oligomerization is performed with a catalyst system including the ionic liquid and a halide component. This observation is further confirmed by FIG. 5 which depicts the overlaid gas chromatographs of the products comprising unreacted monomer and oligomer product for comparative Example 6 and Example 8. As can be seen, the gas chromatograph for comparative Example 6 shows the corresponding product contained a small amount of trimer through pentamer oligomers, and most of the oligomers were heavy $C_{60+}$ oligomers. In contrast, the gas chromatograph for Example 8 shows the corresponding product contained distinct multiples of $C_{10}$ oligomers (e.g., $C_{20}$, $C_{30}$, $C_{40}$, $C_{50}$, $C_{60}$, and so on oligomers), predominantly containing dimer ($C_{20}$), trimer ($C_{30}$), tetramer ($C_{40}$), pentamer ($C_{50}$), and hexamer ($C_{60}$) oligomers. Thus, FIG. 5 shows that use of a catalyst system comprising an ionic liquid and a halide component, such as for example tert-butyl chloride, is more selective toward a lower carbon number (or lighter) oligomer product distribution. The data further shows that while the distribution produced in Example 2 of U.S. Pat. No. 7,572,944 is not as heavy as the distribution produced in Example 6, the distribution produced in Example 2 of U.S. Pat. No. 7,572,944 is still significantly heavier that the distribution produced in Examples 8 and 9.

To further qualitatively evaluate the difference between Examples 6, 7, 8, and 9, the data from the SimDist analysis for Examples 6, 8, and 9 was utilized to determine the amount of monomer and various oligomers present in the Examples 6, 8, and 9. This data was then utilized to determine the approximate true boiling points where the $C_{10}$, $C_{20}$, $C_{30}$, $C_{40}$, $C_{50}$, $C_{60}$, and $C_{70+}$ fractions would fall in the SimDist data. These ranges were utilized to determine the approximate amounts of the $C_{10}$, $C_{20}$, $C_{30}$, $C_{40}$, $C_{50}$, $C_{60}$, and $C_{70+}$ fractions present in the Example 7 (i.e., Example 2 of U.S. Pat. No. 7,572,944) oligomerization from its respective SimDist data. The true boiling point ranges for the $C_{10}$, $C_{20}$, $C_{30}$, $C_{40}$, $C_{50}$, $C_{60}$, and $C_{70+}$ fractions and the amount of the $C_{10}$, $C_{20}$, $C_{30}$, $C_{40}$, $C_{50}$, $C_{60}$, and $C_{70+}$ fractions in Examples 6, 8, and 9 are provided in Table 6-4 along with the calculated approximate amount of the $C_{10}$, $C_{20}$, $C_{30}$, $C_{40}$, $C_{50}$, $C_{60}$, and $C_{70+}$ fractions for Example 7 (i.e., Example 2 of U.S. Pat. No. 7,572,944). The amount of the $C_{10}$, $C_{20}$, $C_{30}$, $C_{40}$, $C_{50}$, $C_{60}$, and $C_{70+}$ fractions in Examples 6, 7, 8, and 9 were then utilized to calculate values for the oligomer distribution of the oligomer product produced in oligomerization Examples 6 to 9. The oligomer distribution data for Examples 6 to 9 are provided in Table 6-5.

TABLE 6-4

Examples 6 to 9, Distribution of Unreacted Monomer and the Oligomer Product

| Distribution | Boiling Point Range (° F.) | Monomer and Oligomer Weight Percent | | | |
|---|---|---|---|---|---|
| | | Example 6 | Example 7 | Example 8 | Example 9 |
| $C_{10}$ | IBP to 350 | 0 | 0.5 | 5 | 14 |
| $C_{20}$ | 350 to 640 | 1 | 4.5 | 15 | 19 |
| $C_{30}$ | 640 to 850 | 2 | 10 | 24 | 21 |
| $C_{40}$ | 850 to 950 | 3 | 15 | 14 | 13 |
| $C_{50}$ | 950 to 1010 | 6 | 0 | 10 | 8 |
| $C_{60}$ | 1010 to 1070 | 7 | 20 | 9 | 7 |
| $C_{70+}$ | 1070+ | 81 | 50 | 23 | 18 |

TABLE 6-5

Examples 6 to 9, Oligomer Distribution of the Oligomer Product

| Distribution (wt. %) | Example 6 | Example 7 | Example 8 | Example 9 |
|---|---|---|---|---|
| $C_{20}$ | 1.0 | 4.5 | 15.8 | 22.1 |
| $C_{30}$ | 2.0 | 10.1 | 25.3 | 24.4 |
| $C_{40}$ | 3.0 | 15.18 | 14.7 | 15.1 |
| $C_{50}$ | 6.0 | 0.0 | 10.5 | 9.3 |
| $C_{60}$ | 7.0 | 20.1 | 9.5 | 8.1 |
| $C_{70+}$ | 81.0 | 50.3 | 24.2 | 20.9 |
| $C_{20}$-$C_{50}$ | 12.0 | 29.7 | 66.3 | 70.9 |
| $C_{30}$-$C_{50}$ | 11.0 | 25.1 | 50.5 | 48.8 |
| $C_{20}$-$C_{40}$ | 6.0 | 29.5 | 55.8 | 61.6 |
| $C_{30}$-$C_{40}$ | 5.0 | 25.1 | 40.0 | 39.5 |
| $C_{50+}$ | 94.0 | 70.3 | 44.2 | 38.4 |
| $C_{60+}$ | 88.0 | 70.3 | 33.7 | 29.2 |

Review of the oligomer distribution data for oligomer product of Examples 6 to 9 confirms the previous observations made using the SimDist data provided Table 6-3. Specifically, 1) the oligomer product of Example 6 produced in the absence of a halide component has a very heavy oligomer distribution where approximately 88 wt. % of the oligomer product has 60 or more carbon atoms and approximately 12 wt. % of the oligomer product has from 20 to 50 carbon atoms, 2) the oligomer product of Example 7 (i.e., Example 2 of U.S. Pat. No. 7,572,944) has a heavy oligomer distribution where 70 wt. % of the oligomer product has 60 or more carbon atoms and approximately 30 wt. % of the oligomer product has from 20 to 50 carbon atoms, and 3) Examples 8 and 9 have a significantly lower oligomer distribution where the oligomer product has less than 35 wt. % (approximately 34 wt. % and 29 wt. %, respectively) oligomers having 60 or more carbon atoms and majority of the oligomer product has greater than 65 wt. % (approximately 66 wt. % and 71 wt. %, respectively) oligomer having from 20 to 50 carbon atoms. The results of comparative Example 6 are similar to the results obtained for comparative Example 1 above (which produced 82.7 wt. % $C_{60+}$ oligomers, see Table 1-3), confirming that oligomerization of 1-decene with N-(n-butyl)pyridinium chloroaluminate at 20° C. without the presence of a halide component makes a heavier oligomer product. This data shows that a catalyst system comprising an ionic liquid and a halide component can be utilized to produce an oligomer product having an oligomer distribution having significant quantities of the commercially attractive oligomers having from 20 to 50 carbon atoms.

In respect to comparative Example 7 and Examples 8 and 9, without being limited to theory, it appears that the use of a large amount of ionic liquid (alternatively stated as a low double bond in monomer to Al in ionic liquid molar ratio) leads to oligomer products having significant quantities of oligomers having greater than 60 carbon atoms. Surprisingly, reduction in the amount of ionic liquid (alternatively stated as a high double bond in monomer to Al in ionic liquid molar ratio) leads to an increase in the quantity of oligomers in the oligomer product having from 20 to 50 carbon atoms.

Without being limited by theory, the halide component (e.g., tert-butyl chloride) appears to control the termination of the oligomerization product. The presence of the halide component appears to induce a downward shift of the carbon number distribution, boiling point distribution, and molecular weight distribution of an oligomer product. It also appears, without being limited by theory, that higher reaction temperatures can affect oligomerization chain growth—possibly by increasing the rate of reaction and the concentration of chain-growing oligomers (e.g., more chains at lower molecular weights are formed and fewer chains at higher molecular weights are formed).

Examples 10 to 21

In Examples 10 to 21, 1-decene was oligomerized in the presence of N-(n-butyl)pyridinium chloroaluminate ionic liquid, and t-butyl chloride as the halide component. In Examples 18 to 21, a diluent, n-nonane, was also used.

A two-neck, 250 mL round bottom flask equipped with a magnetic stir bar and a PTFE septa was prepared in a nitrogen glovebox. The desired quantity 1-decene and n-nonane, if utilized, was added to the round bottom flask. The desired quantity of tert-butyl chloride was then added to the round bottom flask. The contents of the round bottom flask was then heated the desired initial temperature in the range of 63° C. to 135° C. Once the round bottom flask contents reached thermal equilibrium, N-(n-butyl)pyridinium chloroaluminate ionic liquid was added by syringe slowly over the first few minutes to produce the reaction mixture. A rapid exotherm was commonly observed via measurements taken by a thermocouple placed internally of the flask through the PTFE septa. The reaction mixtures initially had a relatively homogenous orange color during the exotherm and remained orange for the remainder of the reaction. The oligomerization reactions were allowed to proceed for a period of either 15 minutes or 60 minutes. Sampling tests revealed that the reactions were typically complete in less than 15 minutes.

At the desired reaction time, an aliquot of the reaction mixture was removed from the round bottom flask (equivalent of reaction zone effluent). The aliquot was treated with 1-butanol to deactivate the ionic liquid catalyst system, leaving a colorless treated reaction mixture with precipitated deactivated ionic liquid catalyst system residue. An aliquot of the 1-butanol treated reaction mixture was then taken by syringe and passed through a PTFE filter to provide a solution of unreacted monomer and oligomer product. The unreacted monomer and oligomer product was then analyzed by gas chromatography using an Agilent 5m SimDist column. Monomer conversion and molecular weight distribution, Mn, of the unreacted monomer and oligomer product was calculated by resolving the oligomer fractions in comparison to neat starting material utilizing n-pentadecane as the internal standard. A summary of the reaction conditions for each of Examples 10 to 21 is provided in Table 10-1 and Table 10-2.

TABLE 10-1

Examples 10 to 15, Reaction Conditions

| | Example | | | | | |
|---|---|---|---|---|---|---|
| | 10 | 11 | 12 | 13 | 14 | 15 |
| 1-Decene(mL) | 200 | 200 | 200 | 200 | 200 | 200 |
| Ionic Liquid (mL) | 0.55 | 0.55 | 0.55 | 0.55 | 2.1 | 10.2 |
| Halide Component(mL) | 0.055 | 0.055 | 0.055 | 0.055 | 0.21 | 0.01 |
| Diluent(mL) | — | — | — | — | — | — |
| Ionic Liquid (vol %) | 0.27 | 0.27 | 0.27 | 0.27 | 1.04 | 4.85 |
| Halide Component (vol % of ionic liquid) | 10 | 10 | 10 | 10 | 10 | 0.1 |
| Reaction Time(min) | 60 | 60 | 60 | 60 | 15 | 15 |
| Reaction Temperature (° C.) | 63 | 80 | 100 | 135 | 80 | 80 |
| Double Bonds in Monomer to Al in Ionic Liquid Molar Ratio | 320 | 320 | 320 | 320 | 83 | 17 |
| Cl in Halide Component to Al in Ionic Liquid Molar Ratio | 0.15 | 0.15 | 0.15 | 0.15 | 0.15 | 0.0015 |
| Conversion (%) | 41.0 | 23.0 | 52.4 | 54.9 | 91.0 | 87.0 |

TABLE 10-2

Examples 16 to 21, Reaction Conditions

| | Example | | | | | |
|---|---|---|---|---|---|---|
| | 16 | 17 | 18 | 19 | 20 | 21 |
| 1-Decene (mL) | 200 | 200 | 200 | 150 | 100 | 50 |
| Ionic Liquid (mL) | 0.55 | 0.21 | 2.1 | 2.1 | 2.1 | 2.1 |
| Halide Component (mL) | 0.055 | 0.021 | 0.21 | 0.21 | 0.21 | 0.21 |
| Diluent (mL) | — | — | — | 50 | 100 | 150 |
| Ionic Liquid (vol %) | 0.27 | 0.10 | 1.04 | 1.04 | 1.04 | 1.04 |
| Halide Component (vol % of ionic liquid) | 10 | 10 | 10 | 10 | 10 | 10 |
| Reaction Time (min) | 15 | 15 | 60 | 60 | 60 | 60 |
| Reaction Temperature (° C.) | 80 | 80 | 80 | 80 | 80 | 80 |
| Max Reaction Temperature (° C.) | — | — | 155.2 | 140.9 | 115 | 93.3 |
| Double Bonds in Monomer to Al in Ionic Liquid Molar Ratio | 320 | 839 | 83.9 | 62.9 | 42.0 | 21.0 |
| Cl in Halide Component to Al in Ionic Liquid Molar Ratio | 0.15 | 0.15 | 0.15 | 0.15 | 0.15 | 0.15 |
| Ionic Liquid to Halide Component Volume Ratio | 10 | 10 | 10 | 10 | 10 | 10 |
| Conversion (%) | 40.4 | 0.0 | 57.5 | 60.5 | 75.1 | 84.5 |

The vol % of ionic liquid is based on the total volume of 1-decene, ionic liquid, and diluent (if used). The vol % of the halide component (tert-butyl chloride) is based on the volume of the ionic liquid.

The unreacted monomer and oligomer product obtained for each of Examples 10 to 21 was analyzed by gas chromatography on an Agilent® 5m SimDist column. The distribution of the unreacted monomer and oligomer product in the oligomerization reactions of Examples 10 to 21 are provided in Tables 10-3 and 10-4.

TABLE 10-3

Examples 10 to 15, Distribution of Unreacted Monomer and the Oligomer Product

| Distribution | Example | | | | | |
|---|---|---|---|---|---|---|
| (wt. %) | 10 | 11 | 12 | 13 | 14 | 15 |
| $C_{10}$ | 59.0 | 77.0 | 47.6 | 45.1 | 9.0 | 13.0 |
| $C_{20}$ | 1.7 | 1.0 | 7.3 | 20.7 | 7.5 | 7.2 |
| $C_{30}$ | 4.9 | 1.6 | 6.8 | 9.2 | 6.5 | 8.1 |
| $C_{40}$ | 3.3 | 2.0 | 7.3 | 7.7 | 6.5 | 6.3 |
| $C_{50}$ | 3.6 | 2.2 | 6.5 | 5.3 | 6.4 | 6.0 |
| $C_{60+}$ | 27.6 | 16.2 | 24.4 | 11.9 | 64.1 | 59.4 |

TABLE 10-4

Examples 16 to 21, Distribution of Unreacted Monomer and the Oligomer Product

| Distribution | Example | | | | | |
|---|---|---|---|---|---|---|
| (wt. %) | 16 | 17 | 18 | 19 | 20 | 21 |
| $C_{10}$ | 59.6 | 100 | 42.5 | 39.5 | 24.9 | 15.5 |
| $C_{20}$ | 0.8 | 0 | 20.7 | 24.1 | 20 | 16.6 |
| $C_{30}$ | 3.5 | 0 | 12.6 | 14.0 | 12.1 | 19.0 |
| $C_{40}$ | 2.5 | 0 | 7.0 | 8.0 | 9.9 | 12.9 |
| $C_{50}$ | 3.6 | 0 | 5.6 | 6.7 | 8.7 | 8.4 |
| $C_{60+}$ | 30 | 0 | 11.5 | 7.7 | 24.4 | 27.7 |

The results shown in Tables 10-3 and 10-4 were used to calculate the oligomer distributions of the oligomer product in Examples 10 to 21 and an approximate average molecular weight, Mn, for Examples 10 to 21. The oligomer distributions and approximate average molecular weights for Examples 10 to 21 are provided in Tables 10-5 and 10-6.

TABLE 10-5

Examples 10 to 15, Oligomer Distribution Data and Average Mn of the Oligomer Product

| Distribution | Example | | | | | |
|---|---|---|---|---|---|---|
| (wt. %) | 10 | 11 | 12 | 13 | 14 | 15 |
| $C_{20}$ | 4.14 | 4.35 | 13.96 | 37.77 | 8.24 | 8.28 |
| $C_{30}$ | 11.92 | 6.96 | 13.00 | 16.79 | 7.14 | 9.31 |
| $C_{40}$ | 8.03 | 8.70 | 13.96 | 14.05 | 7.14 | 7.24 |
| $C_{50}$ | 8.76 | 9.57 | 12.43 | 9.67 | 7.03 | 6.90 |
| $C_{60+}$ | 67.15 | 70.43 | 46.65 | 21.72 | 70.44 | 68.28 |
| $C_{20}$-$C_{50}$ | 32.85 | 29.57 | 53.35 | 78.28 | 29.56 | 31.72 |
| $C_{30}$-$C_{50}$ | 28.71 | 25.22 | 39.39 | 40.51 | 21.32 | 23.45 |
| $C_{20}$-$C_{40}$ | 24.09 | 20.00 | 40.92 | 68.61 | 22.53 | 24.83 |
| $C_{30}$-$C_{40}$ | 19.95 | 15.65 | 26.96 | 30.84 | 14.29 | 16.55 |
| $C_{50+}$ | 75.91 | 80.00 | 59.08 | 31.39 | 77.47 | 75.17 |
| Average Mn (g/mol) | 734 | 751 | 653 | 507 | 736 | 726 |

TABLE 10-6

Examples 16 to 21, Oligomer Distribution Data and Average Mn of the Oligomer Product

| Distribution | Example | | | | | |
|---|---|---|---|---|---|---|
| (wt. %) | 16 | 17 | 18 | 19 | 20 | 21 |
| $C_{20}$ | 1.98 | 0 | 36.06 | 39.83 | 26.63 | 19.62 |
| $C_{30}$ | 8.66 | 0 | 21.95 | 23.14 | 16.11 | 22.46 |
| $C_{40}$ | 6.19 | 0 | 12.20 | 13.22 | 13.18 | 15.25 |
| $C_{50}$ | 8.91 | 0 | 9.76 | 11.07 | 11.58 | 9.93 |
| $C_{60+}$ | 74.26 | 0 | 20.03 | 12.73 | 32.49 | 32.74 |
| $C_{20}$-$C_{50}$ | 25.74 | 0 | 79.97 | 87.27 | 67.51 | 67.26 |
| $C_{30}$-$C_{50}$ | 23.76 | 0 | 43.90 | 47.44 | 40.88 | 47.64 |
| $C_{20}$-$C_{40}$ | 16.83 | 0 | 70.21 | 76.20 | 55.93 | 57.33 |
| $C_{30}$-$C_{40}$ | 14.85 | 0 | 34.15 | 36.36 | 29.29 | 37.71 |
| $C_{50+}$ | 83.17 | 0 | 29.79 | 23.80 | 44.07 | 42.67 |
| Average Mn, (g/mol) | 765 | — | 500 | 469 | 572 | 581 |

The data shown in Tables 10-1 to 10-6 indicate that the catalyst system composition and oligomerization conditions can be utilized to tailor the oligomer distribution of the oligomer product. For example, the catalyst system composition and oligomerization conditions in Examples 13 and 18 to 21 produce lighter oligomer product than the oligomerization conditions in Examples 10 to 12 and 14 to 17.

Examples 22 to 38

In Examples 22 to 38, 1-decene was oligomerized in the presence of N-(n-butyl)pyridinium chloroaluminate ionic liquid, tert-butyl chloride as the halide component, and a diluent of n-nonane. A two-neck, 250 mL round bottom flask equipped with a magnetic stir bar and a PTFE septa was prepared in a nitrogen glovebox. A 1:1 volumetric ratio of 1-decene/diluent mixture was charged to the round bottom flask. The diluent mixture contained 80 mL n-nonane and 20 mL of n-pentadecane. The desired quantity of tert-butyl chloride was then added to the round bottom flask. The contents of the round bottom flask was then heated to the desired temperature in the range of 40° C. to 100° C. Once the round bottom flask contents reached thermal equilibrium, the desired quantity of N-(n-butyl)pyridinium chloroaluminate ionic liquid was added by syringe slowly over the first few minutes to produce the reaction mixture. The oligomerization reaction was allowed to proceed for 60 minutes in each of Examples 22 to 38.

An aliquot of the reaction mixture was removed from the round bottom flask (equivalent of reaction zone effluent). The aliquot was treated with 1-butanol to deactivate the ionic liquid catalyst system. An aliquot of the 1-butanol treated reaction mixture was then taken by syringe and passed through a PTFE filter to yield unreacted monomer and oligomer product. A summary of the reaction conditions for Examples 22 to 38 are provided in Tables 22-1, 22-3, and 22-4.

TABLE 22-1

Examples 22 to 27, Reaction Conditions

| | Example | | | | | |
|---|---|---|---|---|---|---|
| | 22 | 23 | 24 | 25 | 26 | 27 |
| 1-Decene (mL) | 100 | 100 | 100 | 100 | 100 | 100 |
| Ionic Liquid (mL) | 2 | 2 | 1.3 | 2 | 0.55 | 1.3 |
| Halide Component (mL) | 0.3 | 0.6 | 0.3 | 0.02 | 0.6 | 0.3 |
| Diluent (mL) | 100 | 100 | 100 | 100 | 100 | 100 |
| Ionic Liquid (vol %) | 0.99 | 0.99 | 0.65 | 0.99 | 0.27 | 0.65 |
| Halide Component (vol % of ionic liquid) | 15 | 30 | 23 | 1 | 109 | 23 |
| Reaction Time (min) | 60 | 60 | 60 | 60 | 60 | 60 |
| Reaction Temperature (° C.) | 100 | 70 | 70 | 70 | 70 | 70 |
| Max Reaction Temperature (° C.) | 144 | 130.4 | 124.5 | 103.4 | 115.0 | 125.4 |
| Change in Temperature (° C.) | 44 | 60.4 | 54.5 | 33.4 | 45 | 55.4 |
| Time of Max Reaction Temperature (min) | 3 | 3 | 3.5 | 7 | 4 | 3.5 |
| Double Bonds in Monomer to Al in Ionic Liquid Molar Ratio | 44 | 44 | 68 | 44 | 160 | 68 |
| Cl in Halide Component to Al in Ionic Liquid Molar Ratio | 0.23 | 0.46 | 0.36 | 0.015 | 1.67 | 0.36 |

TABLE 22-2

Examples 28 to 33, Reaction Conditions

| | Example | | | | | |
|---|---|---|---|---|---|---|
| | 28 | 29 | 30 | 31 | 32 | 33 |
| 1-Decene (mL) | 100 | 100 | 100 | 100 | 100 | 100 |
| Ionic Liquid (mL) | 1.3 | 0.55 | 0.55 | 1.3 | 1.3 | 1.3 |
| Halide Component (mL) | 0.3 | 0.3 | 0.3 | 0.6 | 0.02 | 0.02 |
| Diluent (mL) | 100 | 100 | 100 | 100 | 100 | 80 |
| Ionic Liquid (vol %) | 0.65 | 0.27 | 0.27 | 0.65 | 0.65 | 0.65 |
| Halide Component (vol % of ionic liquid) | 23 | 54 | 54 | 46 | 1.5 | 1.5 |
| Reaction Time (min) | 60 | 60 | 60 | 60 | 60 | 60 |
| Reaction Temperature (° C.) | 70 | 40 | 100 | 40 | 40 | 100 |
| Max Reaction Temperature (° C.) | 126.1 | 68.3 | 135.8 | 101.8 | 59.7 | 122.1 |
| Change in Temperature (° C.) | 56.1 | 28.3 | 35.8 | 61.8 | 19.7 | 22.1 |
| Time of Max Reaction Temperature (min) | 3.5 | 13 | 3 | 5 | 17 | 8 |
| Double Bonds in Monomer to Al in Ionic Liquid Molar Ratio | 68 | 160 | 160 | 68 | 68 | 68 |
| Cl in Halide Component to Al in Ionic Liquid Molar Ratio | 0.36 | 0.84 | 0.84 | 0.71 | 0.024 | 0.024 |

TABLE 22-3

Examples 34 to 38, Reaction Conditions

| | Example | | | | |
|---|---|---|---|---|---|
| | 34 | 35 | 36 | 37 | 38 |
| 1-Decene (mL) | 100 | 100 | 100 | 100 | 100 |
| Ionic Liquid (mL) | 1.3 | 2 | 1.3 | 0.55 | 1.3 |
| Halide Component (mL) | 0.3 | 0.3 | 0.6 | 0.02 | 0.3 |
| Diluent (mL) | 100 | 100 | 100 | 100 | 100 |
| Ionic Liquid (vol %) | 0.65 | 1.0 | 0.65 | 0.27 | 0.65 |
| Halide Component (vol % of ionic liquid) | 23 | 15 | 46 | 3.6 | 23 |
| Reaction Time (min) | 60 | 60 | 60 | 60 | 60 |
| Reaction Temperature (° C.) | 70 | 40 | 100 | 70 | 70 |
| Max Reaction Temperature (° C.) | 126.9 | 104.3 | 142.4 | 88.7 | 126 |
| Change in Temperature (° C.) | 56.9 | 64.3 | 42.4 | 18.7 | 56 |

TABLE 22-3-continued

Examples 34 to 38, Reaction Conditions

| | Example | | | | |
|---|---|---|---|---|---|
| | 34 | 35 | 36 | 37 | 38 |
| Time of Max Reaction Temperature (min) | 2.5 | 4.5 | 2.5 | 13 | 3 |
| Double Bonds in Monomer to Al in Ionic Liquid Molar Ratio | 68 | 44 | 68 | 160 | 68 |
| Cl in Halide Component to Al in Ionic Liquid Molar Ratio | 0.36 | 0.23 | 0.71 | 0.056 | 0.356 |

The vol % of ionic liquid is based on the total volume of 1-decene, ionic liquid, and diluent. The vol % of the halide component (tert-butyl chloride) is based on the volume of the ionic liquid.

The unreacted monomer and oligomer product obtained from Examples 22 to 38 were analyzed by gas chromatography using an Agilent® 5m SimDist column. Monomer conversion and the distribution of the unreacted monomer and oligomer product were calculated by resolving the oligomer fractions in comparison to neat starting material utilizing n-pentadecane as the internal standard. The distribution of the unreacted monomer and oligomer product in the oligomerization reactions of Examples 22 to 38 are provided in Tables 22-4, 22-5, and 22-6.

TABLE 22-4

Examples 22 to 27, Distribution of Unreacted Monomer and the Oligomer Product

| Distribution | Example | | | | | |
|---|---|---|---|---|---|---|
| (wt. %) | 22 | 23 | 24 | 25 | 26 | 27 |
| Isomerized $C_{10}$ | 2.1 | 2.0 | 1.1 | 0 | 0.6 | 0.7 |
| $C_{10}$ | 31.8 | 5.8 | 13.0 | 36.6 | 16.2 | 8.4 |
| $C_{20}$ | 30.3 | 19.1 | 19.2 | 6.9 | 17.5 | 13.5 |
| $C_{30}$ | 18.6 | 27.4 | 26.0 | 17.9 | 23.0 | 24.8 |
| $C_{40}$ | 7.8 | 14.2 | 14.1 | 9.6 | 14.3 | 13.9 |
| $C_{50}$ | 4.2 | 13.1 | 10.9 | 9.2 | 11.4 | 14.0 |
| $C_{60}$ | 3.4 | 12.6 | 10.4 | 13.0 | 12.5 | 16.1 |
| $C_{70+}$ | 1.9 | 5.9 | 5.3 | 6.7 | 4.6 | 8.5 |

TABLE 22-5

Examples 28 to 33, Distribution of Unreacted Monomer and the Oligomer Product

| Distribution | Example | | | | | |
|---|---|---|---|---|---|---|
| (wt. %) | 28 | 29 | 30 | 31 | 32 | 33 |
| Isomerized $C_{10}$ | 0.7 | 0 | 1.8 | 0.6 | 0 | 0.2 |
| $C_{10}$ | 7.2 | 10.4 | 34.2 | 3.7 | 44.4 | 40.3 |
| $C_{20}$ | 12.7 | 4.6 | 33.2 | 9.0 | 2.2 | 10.7 |
| $C_{30}$ | 25.0 | 28.7 | 16.9 | 32.8 | 11.5 | 29.0 |
| $C_{40}$ | 15.1 | 23.9 | 5.5 | 26.0 | 7.6 | 11.2 |
| $C_{50}$ | 12.7 | 19.9 | 2.8 | 18.1 | 11.3 | 3.2 |
| $C_{60}$ | 17.1 | 10.9 | 3.2 | 8.7 | 15.0 | 2.5 |
| $C_{70+}$ | 9.6 | 1.5 | 2.4 | 1.2 | 7.9 | 2.9 |

TABLE 22-6

Examples 34 to 38, Distribution of Unreacted Monomer and the Oligomer Product

| Distribution | Example | | | | |
|---|---|---|---|---|---|
| (wt. %) | 34 | 35 | 36 | 37 | 38 |
| Isomerized $C_{10}$ | 0.9 | 0.4 | 2.7 | 0 | 1.3 |
| $C_{10}$ | 9.6 | 4.4 | 16.0 | 39.0 | 13.2 |
| $C_{20}$ | 14.0 | 8.1 | 36.6 | 6.4 | 16.7 |
| $C_{30}$ | 27.8 | 24.1 | 24.4 | 20.6 | 30.5 |
| $C_{40}$ | 16.4 | 18.3 | 9.9 | 9.6 | 17.6 |
| $C_{50}$ | 13.1 | 20.1 | 5.0 | 8.2 | 10.0 |
| $C_{60}$ | 13.0 | 20.4 | 4.7 | 10.4 | 8.6 |
| $C_{70+}$ | 5.2 | 4.2 | 0.8 | 5.8 | 2.1 |

The results shown in Tables 22-4 to 22-6 were used to calculate the distribution of the oligomer product, the approximate average molecular weight (Mn), and an approximate 100° C. kinematic viscosity of the $C_{30+}$ portion of the oligomer product for Examples 22 to 38 in Tables 22-7, 22-8, and 22-9. The approximate average molecular weights, Mn, were calculated using the assumption that all of the $C_{70+}$ oligomers (i.e., the $C_{70}$ oligomer and any oligomers having more than 70 carbon atoms, if any) are a $C_{70}$ oligomer. Since Examples 22 to 38 contained less than 11 wt. % of $C_{70+}$ oligomers, this assumption would lead to a slightly lower average molecular weight than the actual molecular weight for the oligomer product of Example 22 to 38. The approximate 100° C. kinematic viscosity of the $C_{30+}$ portion of the oligomer product were calculated using a proprietary program which estimates 100° C. kinematic viscosity of the $C_{30+}$ portion of a 1-decene based oligomer product by correlating the observed example distribution of the $C_{30+}$ portion of the 1-decene based oligomer product with a database of kinematic viscosities for the $C_{30+}$ portion of the 1-decene based oligomer product having a known distribution of $C_{30+}$ 1-decene oligomers.

TABLE 22-7

Examples 22 to 27, Oligomer Distribution Data, Average Mn of the Oligomer Product, and $C_{30+}$ 100° C. Viscosity

| Distribution | Example | | | | | |
|---|---|---|---|---|---|---|
| (wt. %) | 22 | 23 | 24 | 25 | 26 | 27 |
| $C_{20}$ | 45.77 | 20.69 | 22.35 | 10.90 | 21.01 | 14.87 |
| $C_{30}$ | 28.10 | 29.69 | 30.27 | 28.28 | 27.61 | 27.31 |
| $C_{40}$ | 11.78 | 15.38 | 16.41 | 15.17 | 17.17 | 15.31 |
| $C_{50}$ | 6.34 | 14.19 | 12.69 | 14.53 | 13.69 | 15.42 |
| $C_{60}$ | 5.14 | 13.65 | 12.11 | 20.54 | 15.01 | 17.73 |
| $C_{70+}$ | 2.87 | 6.39 | 6.17 | 10.58 | 5.52 | 9.36 |
| $C_{20}$-$C_{50}$ | 91.99 | 79.96 | 81.72 | 68.88 | 79.47 | 72.91 |
| $C_{30}$-$C_{50}$ | 46.22 | 59.26 | 59.37 | 57.98 | 58.46 | 58.04 |
| $C_{20}$-$C_{40}$ | 85.65 | 65.76 | 69.03 | 54.34 | 65.79 | 57.49 |
| $C_{30}$-$C_{40}$ | 39.88 | 45.07 | 46.68 | 43.44 | 44.78 | 42.62 |
| $C_{50+}$ | 14.35 | 34.24 | 30.97 | 45.66 | 34.21 | 42.51 |
| $C_{60+}$ | 8.01 | 20.04 | 18.28 | 31.12 | 20.53 | 27.09 |
| $C_{20}/C_{30}$ | 1.63 | 0.70 | 0.74 | 0.39 | 0.76 | 0.55 |
| $C_{30}/C_{40}$ | 2.37 | 1.93 | 1.84 | 1.86 | 1.60 | 1.78 |
| Average Mn (g/mol) | 430 | 547 | 535 | 614 | 549 | 593 |
| $C_{30+}$ 100° C. Viscosity (cSt) | 5.5 | 6.9 | 6.6 | 7.7 | 6.9 | 7.5 |

TABLE 22-8

Examples 28 to 33, Oligomer Distribution Data, Average Mn of the Oligomer Product, and $C_{30+}$ 100° C. Viscosity

| Distribution (wt. %) | Example | | | | | |
|---|---|---|---|---|---|---|
| | 28 | 29 | 30 | 31 | 32 | 33 |
| $C_{20}$ | 13.77 | 5.14 | 51.88 | 9.39 | 3.96 | 17.98 |
| $C_{30}$ | 27.11 | 32.07 | 26.41 | 34.24 | 20.72 | 48.74 |
| $C_{40}$ | 16.38 | 26.70 | 8.59 | 27.14 | 13.69 | 18.82 |
| $C_{50}$ | 13.77 | 22.23 | 4.38 | 18.89 | 20.36 | 5.38 |
| $C_{60}$ | 18.55 | 12.18 | 5.00 | 9.08 | 27.03 | 4.20 |
| $C_{70+}$ | 10.41 | 1.68 | 3.75 | 1.25 | 14.23 | 4.87 |
| $C_{20}$-$C_{50}$ | 71.04 | 86.15 | 91.25 | 89.67 | 58.74 | 90.92 |
| $C_{30}$-$C_{50}$ | 57.27 | 81.01 | 39.38 | 80.27 | 54.77 | 72.94 |
| $C_{20}$-$C_{40}$ | 57.27 | 63.91 | 86.88 | 70.77 | 38.38 | 85.55 |
| $C_{30}$-$C_{40}$ | 43.49 | 58.77 | 35.00 | 61.38 | 34.41 | 67.56 |
| $C_{50+}$ | 42.73 | 36.09 | 13.13 | 29.23 | 61.62 | 14.45 |
| $C_{60+}$ | 28.96 | 13.85 | 8.75 | 10.33 | 41.26 | 9.08 |
| $C_{10}/C_{30}$ | 0.51 | 0.16 | 1.97 | 0.28 | 0.20 | 0.37 |
| $C_{30}/C_{40}$ | 1.65 | 1.20 | 3.09 | 1.26 | 1.51 | 2.60 |
| Average Mn (g/mol) | 600 | 575 | 416 | 545 | 686 | 483 |
| $C_{30+}$ 100° C. Viscosity (cSt) | 7.6 | 6.5 | 5.5 | 6.1 | 9.0 | 5.2 |

TABLE 22-9

Examples 34 to 38, Oligomer Distribution Data, Average Mn of the Oligomer Product, and $C_{30+}$ 100° C. Viscosity

| Distribution (wt. %) | Example | | | | |
|---|---|---|---|---|---|
| | 34 | 35 | 36 | 37 | 38 |
| $C_{20}$ | 15.64 | 8.51 | 44.96 | 10.49 | 19.53 |
| $C_{30}$ | 31.06 | 25.32 | 29.98 | 33.77 | 35.67 |
| $C_{40}$ | 18.32 | 19.22 | 12.16 | 15.74 | 20.58 |
| $C_{50}$ | 14.64 | 21.11 | 6.14 | 13.44 | 11.70 |
| $C_{60}$ | 14.53 | 21.43 | 5.77 | 17.05 | 10.06 |
| $C_{70+}$ | 5.81 | 4.41 | 0.98 | 9.51 | 2.46 |
| $C_{20}$-$C_{50}$ | 79.66 | 74.16 | 93.24 | 73.44 | 87.49 |
| $C_{30}$-$C_{50}$ | 64.02 | 65.65 | 48.28 | 62.95 | 67.95 |
| $C_{20}$-$C_{40}$ | 65.03 | 53.05 | 87.10 | 60.00 | 75.79 |
| $C_{30}$-$C_{40}$ | 49.39 | 44.54 | 42.14 | 49.51 | 56.26 |
| $C_{50+}$ | 34.97 | 46.95 | 12.90 | 40.00 | 24.21 |
| $C_{60+}$ | 20.34 | 25.84 | 6.76 | 26.56 | 12.51 |
| $C_{20}/C_{30}$ | 0.50 | 0.34 | 1.50 | 0.31 | 0.55 |
| $C_{30}/C_{40}$ | 1.70 | 1.32 | 2.48 | 2.16 | 1.74 |
| Average Mn (g/mol) | 560 | 611 | 423 | 592 | 512 |
| $C_{30+}$ 100° C. Viscosity (cSt) | 6.7 | 7.5 | 5.4 | 7.0 | 5.9 |

The data shown in Tables 22-1 to 22-9 indicate that a trimer+ ($C_{30+}$) viscosity of about 5.2 cSt can be achieved at a reaction temperature around 100° C. High values for maximum reaction temperatures result in high levels of dimer which can affect product properties (more volatile, undesirable flash/fire point) and which can allow a dimer recycle stream in continuous processes.

The data shown in Tables 22-1 to 22-9 indicate that that a wide variety of oligomer distributions, having different shapes and breadths, can be formed by adjusting one or more of the double bonds in monomer to Al in ionic liquid molar ratio, the Cl in halide component to Al in the ionic liquid molar ratio, oligomerization temperature, and oligomerization time. The data shown in Tables 22-1 to 22-9 show that, generally, an increase in the concentration of the ionic liquid increases conversion and increases the viscosity of the product while an increase in the concentration of halide component (e.g., tert-butyl chloride) significantly increases conversion while, in contrast to an increase in ionic liquid concentration, decreases the viscosity of the product. Further it can be seen that the oligomer product distribution can be tailored to favor trimer production.

Examples 39 and 40

In Example 39, the product mixture of Example 9 was hydrogenated using a nickel-based hydrogenation catalyst. The hydrogenated product mixture was water clear in color with a bromine index of <200. The hydrogenated product mixture was then fractionated by vacuum distillation into 1) a $C_{10}$ and $C_{20}$ (650° F.) fraction and 2) a second fraction containing the remaining hydrogenated oligomers, e.g., a polyalphaolefin product of trimer+ ($C_{30+}$) oligomers. The polyalphaolefin product fraction had a viscosity of 8.0 cSt. The chloride content of the polyalphaolefin product was measured by X-ray fluorescence spectrometry (XRF) to be <0.3 ppmw.

In Example 40, the oligomer product of Example 5, like that of Example 9, was hydrogenated using a nickel-based hydrogenation catalyst and then fractionated by vacuum distillation into a 1) $C_{10}$ and $C_{20}$ (650° F.) fraction and 2) a second fraction containing the remaining hydrogenated oligomers, e.g., a polyalphaolefin product of trimer+($C_{30+}$) oligomers. The polyalphaolefin product fraction had a viscosity of 9.6 cSt.

Figure 6:
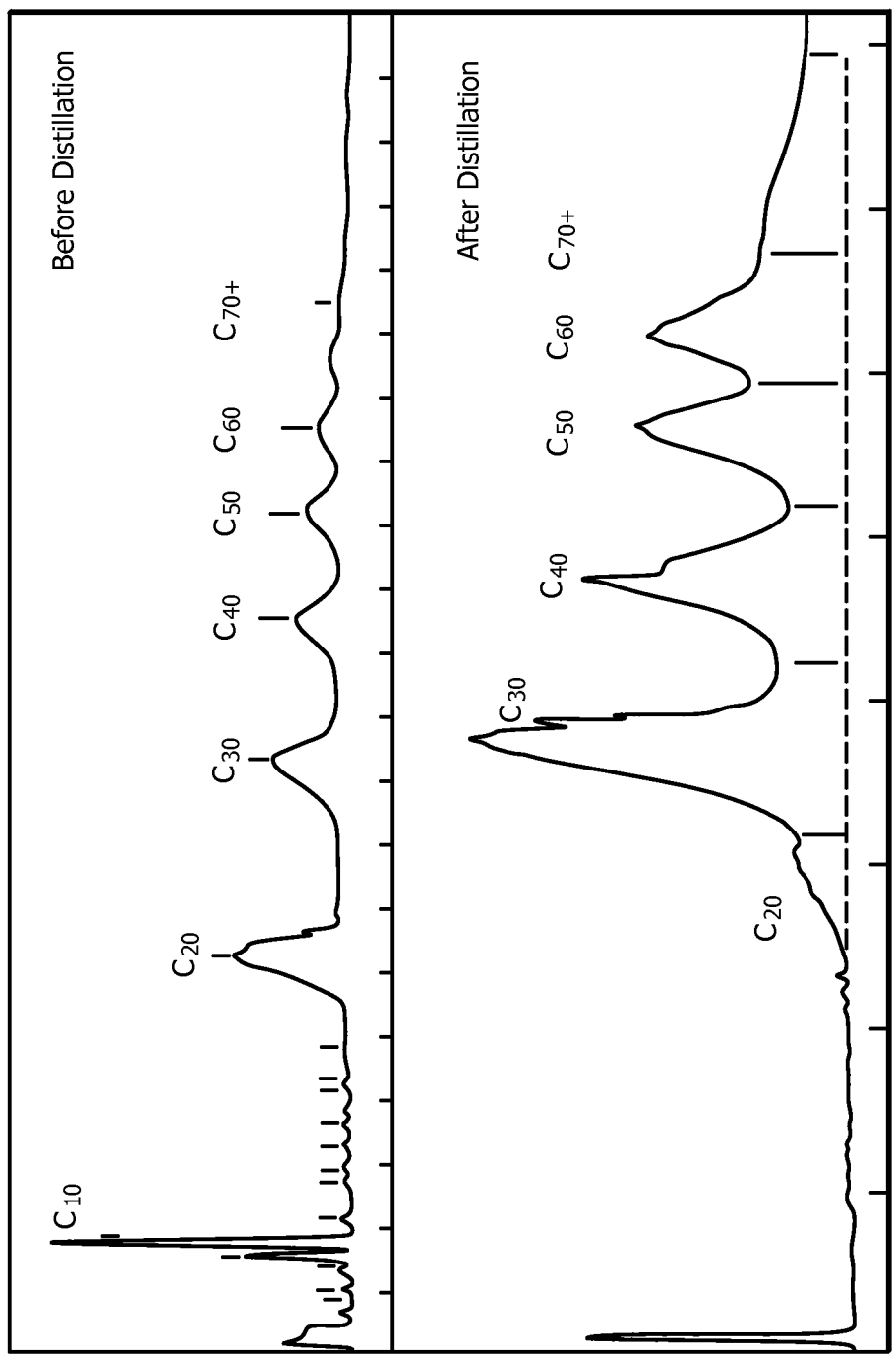
FIG. 6 shows the gas chromatography chromatograms of the hydrogenated $C_{30+}$ portion of the oligomer from Example 39, before and after distillation.
Figure 7:
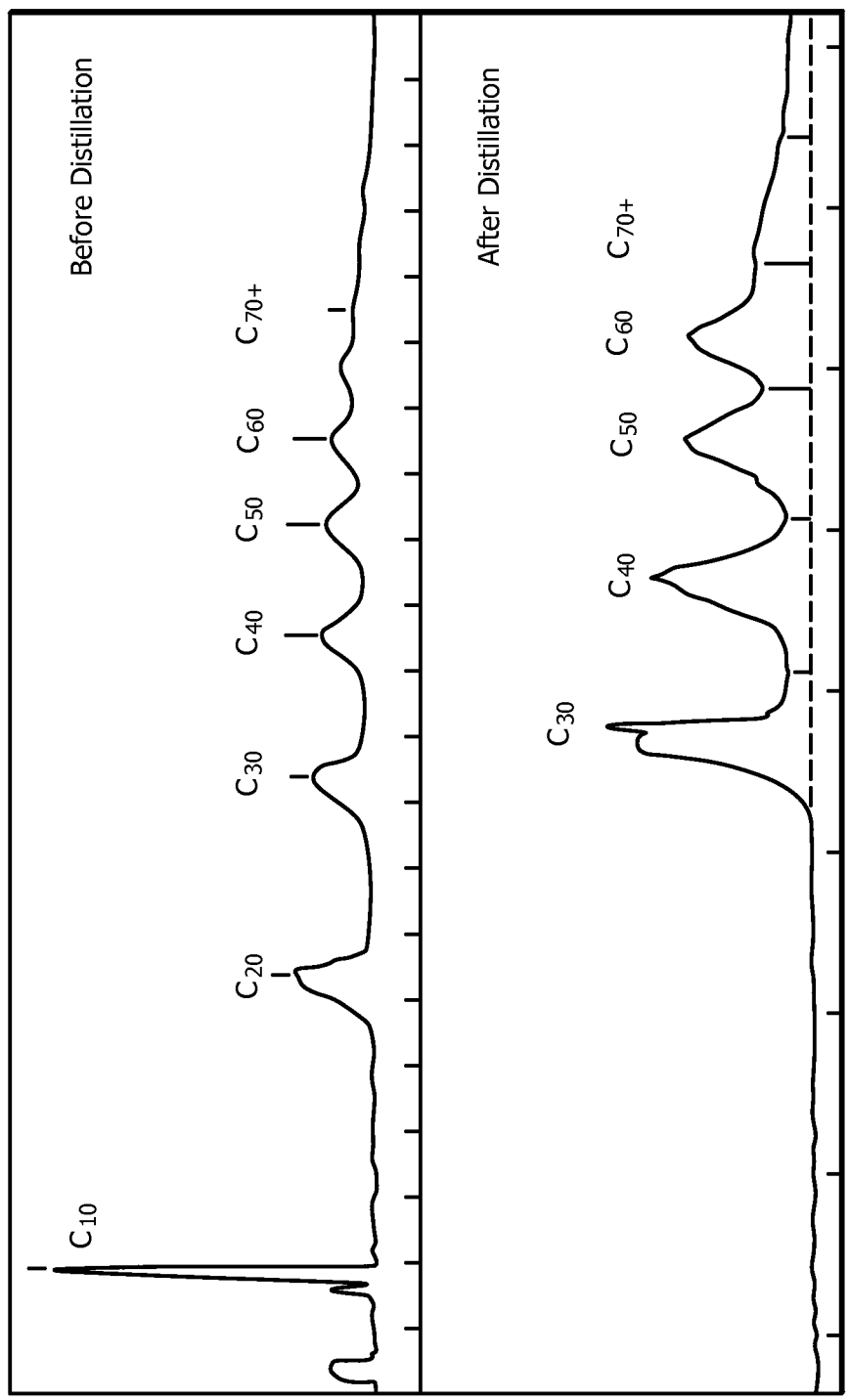
FIG. 7 shows the gas chromatography chromatograms of the hydrogenated $C_{30+}$ portion of the oligomer from Example 40, before and after distillation.

The gas chromatography chromatograms of the hydrogenated oligomer product and polyalphaolefin product for Examples 39 and 40 are shown in FIGS. 6 and 7, respectively. In FIG. 6, the gas chromatography chromatogram for the hydrogenated product mixture of Example 39 before distillation is above the gas chromatography chromatogram for the polyalphaolefin product of Example 39 which was produced by distillation of the hydrogenated product mixture. In FIG. 7, the gas chromatography chromatogram for the hydrogenated product mixture of Example 40 before distillation is above the gas chromatography chromatogram for the polyalphaolefin product fraction of Example 40 which was produced by distillation of the hydrogenated product mixture.

Properties for Examples 39 and 40, along with a comparison of said properties with commercially available synthetic lubricants, are provided in Table 39-1.

TABLE 39-1

Examples 39 to 40, Properties of Polyalphaolefin Product

| | Example 39 | Synfluid ® PAO 8 | Example 40 | DuraSyn ® 170 |
|---|---|---|---|---|
| Kinematic Viscosity at 100° C. (cSt) | 8.0 | 7.8 | 9.6 | 9.8 |
| Kinematic Viscosity at 40° C. (cSt) | 50.9 | 46.4 | 63 | 65.1 |
| Kinematic Viscosity at −40° C. (cSt) | 32,387 | 19,574 | 38.036 | 35,509 |
| Viscosity Index | 127 | 138 | 135 | 133 |
| Pour Point (° C.) | −61 | −56 | −61 | −51 |
| Flash Point (COC) (° C.) | 253 | 262 | 268 | 277 |
| Bromine Index | <200 | <200 | <200 | 200 |

The data in Table 39-1 shows that polyalphaolefins produced from an ionic liquid catalyst system comprising an ionic liquid and a halide component can have comparable properties to commercially available polyalphaolefin products.

Additional Disclosure

E1. A process comprising:
  a) contacting 1) a monomer comprising a $C_6$ to $C_{20}$ olefin, 2) a haloaluminate ionic liquid, and 3) a halide component comprising a Brönsted acid or an organohalide in a reaction zone; and
  b) forming an oligomer product in the reaction zone.

E2. The process of E1, wherein the monomer and the halide component are contacted prior to contacting monomer with the haloaluminate ionic liquid.

E3. The process of E1, wherein the haloaluminate ionic liquid and the halide component are contacted prior to contacting monomer with the haloaluminate ionic liquid.

E4. The process of E1, wherein the haloaluminate ionic liquid and the halide component are separately and simultaneously contacted with the monomer.

E5. The process of E1, wherein the monomer and the haloaluminate ionic liquid are contacted prior to contacting the haloaluminate ionic liquid with the halide component.

E6. A process comprising:
  a) introducing 1) a monomer comprising a $C_6$ to $C_{20}$ olefin, 2) a haloaluminate ionic liquid, 3) a halide component selected from the group consisting of a Brönsted acid and an organohalide, or 4) any combination thereof into a reaction zone; and
  b) oligomerizing the monomer in the reaction zone to form an oligomer product.

E7. The process of E6, wherein a stream comprising the monomer and the halide component and a stream comprising the haloaluminate ionic liquid are separately (or simultaneously, or separately and simultaneously) introduced into the reaction zone.

E8. The process of E6, wherein a stream comprising the haloaluminate ionic liquid and the halide component and a stream comprising the monomer are separately (or simultaneously, or separately and simultaneously) introduced into the reaction zone.

E9. The process of E6, wherein a stream comprising the monomer, a stream comprising the haloaluminate ionic liquid, and a stream comprising the halide component are separately (or simultaneously, or separately and simultaneously) introduced into the reaction zone.

E10. The process of E6, wherein a stream comprising the monomer and the haloaluminate ionic liquid and a stream comprising the halide component are separately (or simultaneously, or separately and simultaneously) introduced into the reaction zone.

E11. A process comprising:
  a) periodically or continuously introducing 1) a monomer comprising a $C_6$ to $C_{20}$ olefin, 2) a haloaluminate ionic liquid, and 3) a halide component selected from the group consisting of a Brönsted acid and an organohalide into a reaction zone; and
  b) oligomerizing the monomer in the reaction zone to form an oligomer product.

E12. The process of E11, wherein a stream comprising the monomer and the halide component and a stream comprising the haloaluminate ionic liquid are, periodically or continuously, and separately (or simultaneously, or separately and simultaneously) introduced into the reaction zone.

E13. The process of E11, wherein a stream comprising the haloaluminate ionic liquid and optionally the halide component and a stream comprising the monomer are, periodically or continuously, and separately (or simultaneously, or separately and simultaneously) introduced into the reaction zone.

E14. The process of E11, wherein a stream comprising the monomer, a stream comprising the haloaluminate ionic liquid, and a stream comprising the halide component are, periodically or continuously, and separately (or simultaneously, or separately and simultaneously) introduced into the reaction zone.

E15. The process of E11, wherein a stream comprising the monomer and the haloaluminate ionic liquid and a stream comprising the halide component are, periodically or continuously, and separately (or simultaneously, or separately and simultaneously) introduced into the reaction zone.

E16. A process comprising:
  a) periodically or continuously introducing one or more streams comprising 1) a monomer comprising a $C_6$ to $C_{20}$ olefin, 2) a haloaluminate ionic liquid, 3) a halide component selected from the group consisting of a Brönsted acid and an organohalide, or 4) any combination thereof into a reaction zone containing the same or different monomer, the same or different haloaluminate ionic liquid, and the same or different halide component;
  b) oligomerizing the monomer in the reaction zone to form an oligomer product.

E17. The process of E16, wherein a stream comprising the monomer and optionally the halide component and a stream comprising the haloaluminate ionic liquid are, periodically or continuously, and separately (or simultaneously, or separately and simultaneously) introduced into the reaction zone containing the same or different monomer, the same or different haloaluminate ionic liquid, and the same or different halide component.

E18. The process of E16, wherein a stream comprising the haloaluminate ionic liquid and optionally the halide component and a stream comprising the monomer are, periodically or continuously, and separately (or simultaneously, or separately and simultaneously) introduced into the reaction zone containing the same or different monomer, the same or different haloaluminate ionic liquid, and the same or different halide component.

E19. The process of E16, wherein a stream comprising the monomer, a stream comprising the haloaluminate ionic liquid, and optionally a stream comprising the halide component are, periodically or continuously, and separately (or simultaneously, or separately and simultaneously) introduced into the reaction zone containing the same or different monomer, the same or different haloaluminate ionic liquid, and the same or different halide component.

E20. The process of E16, wherein a stream comprising the monomer and the haloaluminate ionic liquid and optionally a stream comprising the halide component are, periodically or continuously, and separately (or simultaneously, or separately and simultaneously) introduced into the reaction zone containing the same or different monomer, the same or different haloaluminate ionic liquid, and the same or different halide component.

E21. The process of any one of E1 to E20, wherein the reaction zone comprises a continuous stirred tank reactor (CSTR), a plug flow reactor, or any combination thereof; alternatively, a plug flow reactor; or alternatively, a tubular reactor.

E22. The process of E21, wherein the reaction zone comprises at least two reactors in series, in parallel, or any combination thereof; alternatively, in series; or alternatively, in parallel.

E23. The process of any one of E1 to E22, wherein the oligomer product is formed at any molar ratio of carbon-carbon double bonds of the monomer to aluminum in the haloaluminate ionic liquid (minimum, maximum, or range) disclosed herein.

E24. The process of any one of E1 to E23, wherein oligomer product is formed at any molar ratio of halide in the halide component to aluminum in the haloaluminate ionic liquid (minimum, maximum, or range) disclosed herein.

E25. The process of any one of E1 to E24, wherein the haloaluminate ionic liquid is a trialkylammonium haloaluminate ionic liquid, a tetraalkylammonium haloaluminate ionic liquid, hydrogen pyridinium haloaluminate ionic liquid, an N-alkylpyridinium haloaluminate ionic liquid, an N,N'-dialkylimidizolium haloaluminate ionic liquid, or any combination thereof; alternatively, a tetraalkylammonium haloaluminate ionic liquid, an N-alkylpyridinium haloaluminate ionic liquid, an N,N'-dialkylimidizolium haloaluminate ionic liquid, or any combination thereof; alternatively, a tetraalkylammonium haloaluminate ionic liquid; alternatively, an N-alkylpyridinium haloaluminate ionic liquid; or alternatively, an N,N'-dialkylimidizolium haloaluminate ionic liquid.

E26. The process of any one of E1 to E24, wherein the ionic liquid is a chloroaluminate ionic liquid, a bromoaluminate ionic liquid, or any combination thereof; alternatively, a chloroaluminate ionic liquid; or alternatively, a bromoaluminate ionic liquid.

E27. The process of any one of E1 to E24, wherein the ionic liquid is N-(n-butyl)pyridinium chloroaluminate, N-(n-butyl)pyridinium bromoaluminate, or any combination thereof; alternatively, N-(n-butyl)pyridinium bromoaluminate; or alternatively, N-(n-butyl)pyridinium chloroaluminate.

E28. The process of any one of E1 to E27, wherein the halide component is a hydrogen halide; alternatively, is hydrogen chloride, hydrogen bromide, or any combination thereof; alternatively, hydrogen chloride; or alternatively, hydrogen bromide.

E29. The process of any one of E1 to E27, wherein the halide component is a $C_1$ to $C_{12}$ organohalide; alternatively, a $C_2$ to $C_{12}$ organohalide; alternatively, a $C_3$ to $C_{12}$ organohalide; alternatively, a $C_1$ to $C_{12}$ alkyl halide; alternatively, a $C_2$ to $C_{12}$ alkyl halide; or alternatively, a $C_3$ to $C_{12}$ alkyl halide.

E30. The process of any one of E1 to E27, wherein the halide component is a propyl halide, a butyl halide, a pentyl halide, a hexyl halide, a heptyl halide, an octyl halide, a nonyl halide, a decyl halide, or any combination thereof.

E31. The process of E29 or E30, wherein the organohalide is a primary organohalide (or a primary alkyl halide), a secondary organohalide (or a secondary alkyl halide), a tertiary organohalide (or a tertiary alkyl halide), or any combination thereof; alternatively, a secondary organohalide (or a secondary alkyl halide), a tertiary organohalide (or a tertiary alkyl halide), or any combination thereof; alternatively, a primary organohalide (or a primary alkyl halide); alternatively, a secondary organohalide (or a secondary alkyl halide); or alternatively, a tertiary organohalide (or a tertiary alkyl halide).

E32. The process of E29, E30, or E31, wherein organohalide (or an alkyl halide) is an organo chloride (or an alkyl halide), an organo bromide (or an alkyl bromide), an organo iodide (or an alkyl iodide), or any combination thereof; alternatively, an organo chloride (or an alkyl halide); alternatively, an organo bromide (or an alkyl bromide); or alternatively, an organo iodide (or an alkyl iodide).

E33. The process of any one of E1 to E32, wherein the oligomer product is formed at any temperature disclosed herein.

E34. The process of any one of E1 to E33, wherein the oligomer product is formed at any pressure disclosed herein.

E35. The process of any one of E1 to E33, wherein the oligomer product is formed at a pressure sufficient to maintain the reaction in a liquid state to any pressure disclosed herein.

E36. The process of any one of E1 to E35, wherein the residence time of the monomer and/or haloaluminate ionic liquid in the reaction zone ranges is any disclosed herein.

E37. The process of any one of E1 to E36, wherein the oligomer product is formed in the presence of an organic reaction medium.

E38. The process of E37, wherein organic reaction medium is a $C_3$ to $C_{18}$ saturated hydrocarbon.

E39. The process of E37 or E38, wherein the organic reaction medium is substantially devoid of isoparaffins.

E40. The process of E37, E38, or E39, wherein the oligomer product is formed in the presence of an organic reaction medium at any organic reaction medium to monomer volume ratio disclosed herein.

E41. The process of any one of E1 to E36, wherein the oligomer product is formed in a substantial absence of an organic reaction medium.

E42. The process of any one of E1 to E41, wherein the oligomer product is formed in an inert atmosphere.

E43. The process of any one of E1 to E42, wherein the oligomer product is formed in the presence of less than 10 mol %, 9 mol %, 8 mol %, 7 mol %, 6 mol %, 5 mol %, 4 mol %, 3 mol %, 2 mol %, 1 mol % isoparaffins.

E44. The process of any one of E1 to E43, wherein the monomer comprises a $C_6$ to $C_{18}$ olefin; alternatively, a $C_8$ to $C_{12}$ olefin.

E45. The process of E1 to E44, wherein the olefin is an alpha olefin; or alternatively, is a normal alpha olefin.

E46. The process of any one of E1 to E43, wherein the olefin comprises 1-hexene, 1-octene, 1-decene, 1-dodecene, 1-tetradecene, or any combination thereof; alternatively, 1-octene, 1-decene, 1-dodecene, or any combination thereof; alternatively, 1-octene; alternatively, 1-decene; or alternatively, 1-dodecene.

E47. The process of any one of claims E1 to E46, wherein the monomer comprises a mixture of olefins having any average molecular weight disclosed herein.

E48. The process of any one of E1 to E47, wherein the monomer comprises at least 50, 70, 75, 80, 85, 90, 95 mol % olefin.

E49. The process of any one of E1 to E47, wherein the olefin comprises at least 50, 70, 75, 80, 85, 90, 95 mol % alpha olefin; or alternatively, normal alpha olefin.

E50. The process of any one of E1 to E43, wherein the monomer comprises a mixture of any two or more of 1-octene, 1-decene, and 1-dodecene.

E51. The process of E50, wherein the mixture comprises at least 90, 92, 93, 94, or 95 mol % of any two of more 1-octene, 1-decene, and 1-dodecene.

E52. The process of E50 or E51, wherein the monomer comprises a mixture of olefins having an average molecular weight ranging from 126 g/mol to 168 g/mol; or alternatively, 133 g/mole to 161 g/mole.

E53. The process of any one of E1 to E43, wherein the monomer comprises 1-octene; alternatively, 1-decene; or alternatively, 1-dodecene.

E54. The process of any one of E1 to E43, wherein the monomer comprises at least 90, 92, 93, 94, or 95 mol % 1-octene; alternatively, 1-decene; or alternatively, 1-dodecene.

E55. The process of any one of E1 to E54, wherein the monomer conversion is any conversion disclosed herein.

E56. The process of any one of E1 to E55, wherein the oligomer product comprises less than 40 wt. %, 30 wt. %, 25 wt. %, 20 wt. %, 18 wt. %, 16 wt. %, 14 wt. %, 12 wt. %, or 10 wt. % $\leq C_{18}$ oligomers.

E57. The process of any one of E1 to E56, wherein the oligomer product comprises less than 30 wt. %, 25 wt. %, 20 wt. %, 15 wt. %, 10 wt. %, 8 wt. %, 6 wt. %, 5 wt. %, 4 wt. %, 3 wt. %, or 2 wt. % $\geq C_{70}$ oligomers.

E58. The process of any one of E1 to E57, wherein the oligomer product has any average molecular weight, Mn, (minimum, maximum, or range) disclosed herein.

E59. The process of any one of E1 to E57, wherein the oligomer product comprises at least 50 wt. %, 60 wt. %, 70 wt. %, 75 wt. %, 80 wt. %, 85 wt. %, 90 wt. %, or 95 wt. % $C_{18}$ to $C_{64}$ oligomers.

E60. The process of any one of E1 to E53, wherein the oligomer product comprises at least 50 wt. %, 60 wt. %, 70 wt. %, 75 wt. %, 80 wt. %, 85 wt. %, or 90 wt. % $C_{18}$ to $C_{54}$ oligomers; alternatively or additionally, a maximum of 100 wt. %, 98 wt. %, 96 wt. %, 95 wt. %, or 94 wt. % $C_{18}$ to $C_{54}$ oligomers; or alternatively, from 50 wt. % to 100 wt. %, from 60 wt. % to 98 wt. %, from 70 wt. % to 98 wt. %, from 70 wt. % to 95 wt. %, from 75 wt. % to 96 wt. %, from 80 wt. % to 96 wt. %, or from 85 wt. % to 96 wt. % $C_{18}$ to $C_{54}$ oligomers.

E61. The process of any one of E1 to E53, wherein the oligomer product comprises at least 35 wt. %, 40 wt. %, 45 wt. %, 50 wt. %, 55 wt. %, 60 wt. %, or 65 wt. % $C_{26}$ to $C_{54}$ oligomers; additionally or alternatively, a maximum of 100 wt. %, 95 wt. %, 90 wt. %, or 85 wt. % $C_{26}$ to $C_{54}$ oligomers; or alternatively, from 35 wt. % to 100 wt. %, from 40 wt. % to 95 wt. %, from 45 wt. % to 90 wt. %, from 40 wt. % to 85 wt. %, from 50 wt. % to 90 wt. %, or from 50 wt. % to 85 wt. %, $C_{26}$ to $C_{54}$ oligomers.

E62. The process of any one of E1 to E61, further comprising isolating one or more fractions of all or a portion of the oligomer product.

E63. The process of any one of E1 to E61, further comprising separating a stream comprising, consisting essentially of, or consisting of, the unreacted monomer and the oligomer product from the reaction zone effluent.

E64. The process of any one of E1 to E61, wherein the process further comprises discharging a reaction zone effluent comprising unreacted monomer, the haloaluminate ionic liquid, and the oligomer product from the reaction zone.

E65. The process of E64, wherein the process comprises periodically or continuously discharging the reaction zone effluent.

E66. The process of E64 or E65, further comprising separating the reaction zone effluent into a first stream comprising all or a portion of the haloaluminate ionic liquid and a second stream comprising, consisting essentially of, or consisting of, unreacted monomer and oligomer product.

E67. The process of E66, wherein the separating of the reaction zone effluent into a first stream comprising all or a portion of the haloaluminate ionic liquid and a second stream comprising, consisting essentially of, or consisting of, unreacted monomer and oligomer product is performed using a coalescer, a centrifuge, a membrane, or any combination thereof; alternatively, a coalescer; alternatively, a centrifuge; alternatively, a membrane.

E68. The process of E66 or E67, wherein the haloaluminate ionic liquid is recycled to the reaction zone.

E69. The process of E68, wherein the haloaluminate ionic liquid to be recycled to the reaction zone is regenerated prior to introduction into the reaction zone.

E70. The process of E68 or E69, wherein the weight ratio of fresh ionic liquid to recycled ionic liquid ranges from 0.1:1 to 10:1.

E71. The process wherein the stream comprising, consisting essentially of, or consisting of, unreacted monomer and oligomer product of E63 or the second stream comprising, consisting essentially of, or consisting of, unreacted monomer and oligomer product of any one of E66 to E70 is treated to quench or remove substantially all of the haloaluminate ionic liquid.

E72. The process further comprising separating the stream comprising, consisting essentially of, or consisting of, unreacted monomer and oligomer product of E63 or the second stream comprising, consisting essentially of, or consisting of, unreacted monomer and oligomer product of any one of E66 to E71 into a third stream comprising, consisting essentially of, or consisting of, unreacted monomer and $\leq C_{18}$ oligomers and a fourth stream comprising, consisting essentially of, or consisting of, $\geq C_{19}$ oligomers.

E73. The process of E72, further comprising separating the fourth stream comprising, consisting essentially of, or consisting of, $\geq C_{19}$ oligomers into one or more fractions comprising all or a portion of $\geq C_{19}$ oligomers.

E74. The process of E73, wherein the at least one of the one or more fractions comprising all or a portion of $\geq C_{19}$ oligomers is selected from the group consisting of a) a fraction comprising from 90 wt. % to 100 wt. % $C_{19}$ to $C_{22}$ oligomers, b) a fraction comprising 90 wt. % to 100 wt. % $C_{22}$ to $C_{26}$ oligomers, c) a fraction comprising 80 wt. % to 90 wt. % $C_{26}$ to $C_{34}$ oligomers and 8 wt. % to 18 wt. % $C_{36}$ to $C_{44}$ oligomers, d) a fraction comprising 85 wt. % to 95 wt. % $C_{32}$ to $C_{40}$ oligomers and 3 wt. % to 13 wt. % $C_{44}$ to $C_{52}$ oligomers, e) a fraction comprising 20 wt. % to 35 wt. % $C_{26}$ to $C_{34}$ oligomers, 40 wt. % to 60 wt. % $C_{36}$ to $C_{44}$ oligomers, and 13 wt. % to 27 wt. % $C_{46}$ to $C_{54}$ oligomers, f) a fraction comprising 35 wt. % to 55 wt. % $C_{32}$ to $C_{40}$ oligomers and 40 wt. % to 60 wt. % $C_{44}$ to $C_{52}$ oligomers, g) a fraction comprising 45 wt. % to 65 wt. % $C_{36}$ to $C_{44}$ oligomers, 22 wt. % to 34 wt. % $C_{46}$ to $C_{54}$ oligomers, and 5 wt. % to 15 wt. % $C_{56}$ to $C_{64}$ oligomers, h) a fraction comprising 12 wt. % to 24 wt. % $C_{32}$ to $C_{40}$ oligomers, 37 wt. % to 57 wt. % $C_{44}$ to $C_{52}$ oligomers, 13 wt. % to 25 wt. % $C_{56}$ to $C_{64}$ oligomers, and 6 wt. % to 18 wt. % $\geq C_{68}$ oligomers, i) a fraction comprising 30 wt. % to 42 wt. % $C_{36}$ to $C_{44}$ oligomers, 27 wt. % to 39 wt. % $C_{46}$ to $C_{54}$ oligomers, 10 wt. % to 22 wt. % $C_{56}$ to $C_{64}$ oligomers, and 9 wt. % to 21 wt. % $\geq C_{66}$ oligomers, and j) any combination of fractions a) to i).

E75. The process of E73 or E74, wherein the third stream comprising, consisting essentially of, or consisting of, unreacted monomer and $\leq C_{18}$ oligomers is recycled to the reaction zone.

E76. The process of E76, wherein the third stream comprising, consisting essentially of, or consisting of, unreacted monomer and $\leq C_{18}$ oligomers is contacted with a molecular sieve, alumina, silica gel, activated carbon, or any combination thereof prior to being recycled to the reaction zone.

E77. The process of any one of E73 to E76, wherein at least one of the one or more fractions comprising all or a portion of $\geq C_{19}$ oligomers is hydrogenated. The hydrogenation of the one or more fractions comprising all or a portion of $\geq C_{19}$ oligomers can yield one or more hydrogenated fractions.

E78. The process comprising separating the stream comprising, consisting essentially of, or consisting of, the unreacted monomer and oligomer product of E63 or the second stream comprising, consisting essentially of, or consisting of, the unreacted monomer and oligomer product of any one of E66 to E71 into a third stream comprising, consisting essentially of, or consisting of, unreacted monomer and $\leq C_{25}$ oligomers and a fourth stream comprising, consisting essentially of, or consisting of, $\geq C_{26}$ oligomers.

E79. The process of E78, further comprising separating the fourth stream comprising, consisting essentially of, or consisting of, $\geq C_{26}$ oligomers into one or more fractions comprising all or a portion of $\geq C_{26}$ oligomers.

E80. The process of E79, wherein the at least one of the one or more fractions comprising all or a portion of $\geq C_{26}$ oligomers is selected from the group consisting of a) a fraction comprising 80 wt. % to 90 wt. % $C_{26}$ to $C_{34}$ oligomers and 8 wt. % to 18 wt. % $C_{26}$ to $C_{34}$ oligomers, b) a fraction comprising 85 wt. % to 95 wt. % $C_{32}$ to $C_{40}$ oligomers and 3 wt. % to 13 wt. % $C_{44}$ to $C_{52}$ oligomers, c) a fraction comprising 20 wt. % to 35 wt. % $C_{26}$ to $C_{34}$ oligomers, 40 wt. % to 60 wt. % $C_{36}$ to $C_{44}$ oligomers, and 13 wt. % to 27 wt. % $C_{46}$ to $C_{54}$ oligomers, d) a fraction comprising 35 wt. % to 55 wt. % $C_{32}$ to $C_{40}$ oligomers and 40 wt. % to 60 wt. % $C_{44}$ to $C_{52}$ oligomers, e) a fraction comprising 45 wt. % to 65 wt. % $C_{36}$ to $C_{44}$ oligomers, 22 wt. % to 34 wt. % $C_{46}$ to $C_{54}$ oligomers, and 5 wt. % to 15 wt. % $C_{56}$ to $C_{64}$ oligomers, f) a fraction comprising 12 wt. % to 24 wt. % $C_{32}$ to $C_{40}$ oligomers, 37 wt. % to 57 wt. % $C_{44}$ to $C_{52}$ oligomers, 13 wt. % to 25 wt. % $C_{56}$ to $C_{64}$ oligomers, and 6 wt. % to 18 wt. %$\geq C_{68}$ oligomers, g) a fraction comprising 30 wt. % to 42 wt. % $C_{36}$ to $C_{44}$ oligomers, 27 wt. % to 39 wt. % $C_{46}$ to $C_{54}$ oligomers, 10 wt. % to 22 wt. % $C_{56}$ to $C_{64}$ oligomers, and 9 wt. % to 21 wt. %$\geq C_{66}$ oligomers, and h) any combination of fractions a) to g).

E81. The process of E79 or E80, wherein the third stream comprising, consisting essentially of, or consisting of, unreacted monomer and $\leq C_{25}$ oligomers is recycled to the reaction zone.

E82. The process of E81, wherein the third stream comprising, consisting essentially of, or consisting of, unreacted monomer and the $\leq C_{25}$ oligomers is contacted with a molecular sieve, alumina, silica gel, activated carbon, or any combination thereof prior to being recycled to the reaction zone.

E83. The process of any one of E79 to E82, wherein at least one of the one or more fractions comprising all or a portion of the $\geq C_{26}$ oligomers is hydrogenated. The hydrogenation of the one or more fractions comprising all or a portion of $\geq C_{26}$ oligomers can yield one or more hydrogenated fractions.

E84. The process of any one of E72 to E83, wherein the separation of the stream comprising, consisting essentially of, or consisting of, the unreacted monomer and oligomer product is performed by distillation.

E85. The process of E72, wherein the fourth stream comprising, consisting essentially of, or consisting of, $\geq C_{19}$ oligomers is hydrogenated. The hydrogenation of the fourth stream can yield hydrogenated $\geq C_{19}$ oligomers.

E86. The process of E85, wherein the hydrogenated $\geq C_{19}$ oligomers are separated into one or more hydrogenated fractions of all or a portion of the hydrogenated $\geq C_{19}$ oligomers.

E87. The process of E78, wherein the fourth stream comprising, consisting essentially of, or consisting of, the $\geq C_{26}$ oligomers is hydrogenated. The hydrogenation of the fourth stream can yield hydrogenated $\geq C_{26}$ oligomers.

E88. The process of E87, wherein the hydrogenated $\geq C_{26}$ oligomers are separated into one or more hydrogenated fractions of all or a portion of the hydrogenated $\geq C_{26}$ oligomers.

E89. The process of E62, wherein at least of the one or more fractions of all or a portion of the oligomer product is hydrogenated to yield one or more hydrogenated fractions.

E90. The process of any one of E63 and E66 to E71, wherein the stream comprising, consisting essentially of, or consisting of, the unreacted monomer and the oligomer product is hydrogenated. The hydrogenation of said stream can yield a hydrogenated stream comprising, consisting of, or consisting essentially of hydrogenated oligomer product and optionally residual unreacted monomer.

E91. The process E90, wherein the hydrogenated stream comprising, consisting of, or consisting essentially of hydrogenated oligomer product and optionally residual unreacted monomer is separated into one or more hydrogenated fractions of all or a portion of the hydrogenated oligomer product.

E92. The process wherein i) at least one of the one or more hydrogenated fractions comprising all or a portion of the hydrogenated $\geq C_{19}$ oligomers of E77, ii) at least one of the one or more hydrogenated fractions comprising all or a portion of the hydrogenated $\geq C_{26}$ oligomers of E83, iii) at least one of the one or more hydrogenated fractions comprising all or a portion of the hydrogenated $\geq C_{19}$ oligomers of E86, iv) at least one of the one or more hydrogenated fractions comprising all or a portion of the hydrogenated $\geq C_{26}$ oligomers of E88, v) at least one of the one or more hydrogenated fractions of all or a portion of the oligomer product of E89, or vi) at least one of the one or more of the hydrogenated fractions of all or a portion of the hydrogenated oligomer product of E91 has a 100° C. kinematic viscosity from 1.8 cSt to 2.2 cSt, from 2.3 cSt to 2.7 cSt, from 2.6 cSt to 3.4 cSt, from 3.6 cSt to 4.4 cSt, from 4.6 cSt to 5.4 cSt, from 5.6 cSt to 6.4 cSt, from 6.6 cSt to 7.4 cSt, from 7.6 cSt to 8.4 cSt, from 8.6 cSt to 9.4 cSt, and from 9.6 cSt to 10.4 cSt.

E93. The process of any one of E50 to E54, wherein the monomer conversion is at least 60 wt. %, 70 wt. %, 75 wt. %, 80 wt. %, 85 wt. %, or 90 wt. %.

E94. The process of any one of E50 to E54 and E93, wherein the oligomer product comprises less than 40 wt. %, 30 wt. %, 25 wt. %, 20 wt. %, 18 wt. %, 16 wt. %, 14 wt. %, 12 wt. %, or 10 wt. % dimer.

E95. The process of any one of E50 to E54 and E93 to E94, wherein the oligomer product comprises less than 30 wt. %, 25 wt. %, 20 wt. %, 15 wt. %, 10 wt. %, 8 wt. %, 6 wt. %, 5 wt. %, 4 wt. %, 3 wt. %, or 2 wt. % oligomer containing 7 or more monomer units.

E96. The process of any one of claims E50 to E54 and E93 to E95, wherein
i) the oligomer product comprises at least 75 wt. %, 80 wt. %, 85 wt. %, 90 wt. %, or 95 wt. % dimers, trimers, tetramers, pentamers, hexamers, heptamers, octamers, nonamers, and/or decamers;
ii) the oligomer product comprises at least 50 wt. %, 55 wt. %, 60 wt. %, 65 wt. %, 70 wt. %, 80 wt. %, 85 wt. %, or 90 wt. % trimers, tetramers, pentamers, hexamers, heptamers, octamers, nonamers, and/or decamers;

iii) the oligomer product comprises at least 75 wt. %, 80 wt. %, 85 wt. %, 90 wt. %, or 95 wt. % dimers, trimers, tetramers, pentamers, hexamers, and/or heptamers;

iv) the oligomer product comprises at least 50 wt. %, 55 wt. %, 60 wt. %, 65 wt. %, 70 wt. %, 80 wt. %, 85 wt. %, or 90 wt. % trimers, tetramers, pentamers, hexamers, and/or heptamers;

v) the oligomer product comprises at least 30 wt. %, 35 wt. %, 40 wt. %, 45 wt. %, 50 wt. %, 55 wt. %, or 60 wt. % dimers trimers, tetramers, and/or pentamers;

vi) the oligomer product comprises at least 25 wt. %, 30 wt. %, 35 wt. %, 40 wt. %, 45 wt. %, or 50 wt. % trimers, tetramers, and/or pentamers;

vii) the oligomer product comprises at least 25 wt. %, 30 wt. %, 35 wt. %, 40 wt. %, 45 wt. %, 50 wt. %, 55 wt. %, or 60 wt. % dimers, trimers, and/or tetramers; or viii) the oligomer product comprises at least 20 wt. %, 25 wt. %, 30 wt. %, 35 wt. %, 40 wt. %, 45 wt. %, or 50 wt. % trimers and/or tetramers.

E97. The process of any one of E50 to E54 and E93 to E95, wherein the oligomer product comprises a total of at least 50 wt. %, 60 wt. %, 70 wt. %, 75 wt. %, 80 wt. %, 85 wt. %, or 90 wt. % dimer, trimer, tetramer and pentamer; additionally or alternatively, a maximum total of 100 wt. %, 98 wt. %, 96 wt. %, 95 wt. %, or 94 wt. % dimer, trimer, tetramer and pentamer; or alternatively, from 50 wt. % to 100 wt. %, from 60 wt. % to 98 wt. %, from 70 wt. % to 98 wt. %, from 70 wt. % to 95 wt. %, from 75 wt. % to 96 wt. %, from 80 wt. % to 96 wt. %, or from 85 wt. % to 96 wt. % dimer, trimer, tetramer and pentamer.

E98. The process of any one of E50 to E54 and E93 to E95, wherein the oligomer product comprises a total of at least 35 wt. %, 45 wt. %, 50 wt. %, 55 wt. %, 60 wt. %, or 65 wt. % trimer, tetramer and pentamer; additionally or alternatively, a maximum total of 100 wt. %, 95 wt. %, 90 wt. %, or 85 wt. % trimer, tetramer and pentamer; or alternatively, a total of from 35 wt. % to 100 wt. %, from 40 wt. % to 95 wt. %, from 45 wt. % to 90 wt. %, from 40 wt. % to 85 wt. %, from 50 wt. % to 90 wt. %, or from 50 wt. % to 85 wt. %, trimer, tetramer and pentamer.

E99. The process of any one of E50 to E54 and E93 to E95, wherein the oligomer product comprises a total of at least 30 wt. %, 35 wt. %, 40 wt. %, 45 wt. %, or 50 wt. % trimer and tetramer; additionally or alternatively, a maximum total of 90 wt. %, or 85 wt. %, 80 wt. %, or 75 wt. % trimer and tetramer; or alternatively, a total of from 30 wt. % to 90 wt. %, from 40 wt. % to 95 wt. %, from 40 wt. % to 90 wt. %, from 40 wt. % to 85 wt. %, from 45 wt. % to 90 wt. %, from 45 wt. % to 85 wt. %, or from 45 wt. % to 80 wt. % $C_{26}$ to $C_{54}$ trimer and tetramer.

E100. The process of any one of E50 to E54 and E93 to E99, further comprising isolating one or more fractions of all or a portion of the oligomer product.

E101. The process of any one of E50 to E54 and E93 to E99, further comprising separating a stream comprising, consisting essentially of, or consisting of, the unreacted monomer and the oligomer product from the reaction zone effluent.

E102. The process of any one of E50 to E54 and E93 to E99, wherein the process further comprises discharging a reaction zone effluent comprising unreacted monomer, the haloaluminate ionic liquid, and the oligomer product from the reaction zone.

E103. The process of E102, wherein the process comprises periodically or continuously discharging the reaction zone effluent.

E104. The process of E102 or E103, further comprising separating the reaction zone effluent into a first stream comprising all or a portion of the haloaluminate ionic liquid and a second stream comprising, consisting essentially of, or consisting of, the unreacted monomer and oligomer product.

E105. The process of E104, wherein the separating of the reaction zone effluent into a first stream comprising all or a portion of the haloaluminate ionic liquid and a second stream comprising, consisting essentially of, or consisting of, unreacted monomer and oligomer product is performed using a coalescer, a centrifuge, a membrane, or any combination thereof; alternatively, a coalescer; alternatively, a centrifuge; alternatively, a membrane.

E106. The process of E104 or E105, wherein the haloaluminate ionic liquid is recycled to the reaction zone.

E107. The process of E106, wherein the haloaluminate ionic liquid to be recycled to the reaction zone is regenerated prior to introduction into the reaction zone.

E108. The process of E106 or E107, wherein the weight ratio of fresh ionic liquid to recycled ionic liquid ranges from 0.1:1 to 10:1.

E109. The process wherein the stream comprising, consisting essentially of, or consisting of, unreacted monomer and oligomer product of E101 or the second stream comprising, consisting essentially of, or consisting of, unreacted monomer and oligomer product of any one of E104 to E108 is treated to quench or remove substantially all of the haloaluminate ionic liquid.

E110. The process further comprising separating the stream comprising, consisting essentially of, or consisting of, the unreacted monomer and oligomer product of E101 or the second stream comprising, consisting essentially of, or consisting of, the unreacted monomer and oligomer product of any one of E102 to E109 into a third stream comprising, consisting essentially of, or consisting of, unreacted monomer and a fourth stream comprising, consisting essentially of, or consisting of, the oligomer product.

E111. The process of E110, further comprising separating the fourth stream comprising, consisting essentially of, or consisting of, the oligomer product into one or more fractions comprising all or a portion of the oligomer product.

E112. The process of E111, wherein the at least one of the one or more fractions comprising all or a portion of the oligomer product is selected from the group consisting of a) a fraction comprising from 90 wt. % to 100 wt. % dimer, b) a fraction comprising 80 wt. % to 90 wt. % trimer and 8 wt. % to 18 wt. % tetramer, c) a fraction comprising 85 wt. % to 95 wt. % trimer and 3 wt. % to 13 wt. % tetramer, d) a fraction comprising 20 wt. % to 35 wt. % trimer, 40 wt. % to 60 wt. % tetramer, and 13 wt. % to 27 wt. % pentamer, e) a fraction comprising 35 wt. % to 55 wt. % trimer and 40 wt. % to 60 wt. % tetramer, f) a fraction comprising 45 wt. % to 65 wt. % tetramer, 22 wt. % to 34 wt. % pentamer, and 5 wt. % to 15 wt. % $C_{56}$ to $C_{64}$ hexamer, g) a fraction comprising 12 wt. % to 24 wt. % trimer, 37 wt. % to 57 wt. % tetramer, 13 wt. % to 25 wt. % pentamer, and 6 wt. % to 18 wt. % hexamer+, h) a fraction comprising 30 wt. % to 42 wt. % tetramer, 27 wt. % to 39 wt. % pentamer, 10 wt. % to 22 wt. % hexamer, and 9 wt. % to 21 wt. % heptamer+, and i) any combination of fractions a) to h).

E113. The process of E111 or E112, wherein the third stream comprising, consisting essentially of, or consisting of, unreacted monomer is recycled to the reaction zone.

E114. The process of E113, wherein the third stream comprising, consisting essentially of, or consisting of, unreacted monomer is contacted with a molecular sieve, alumina, silica gel, activated carbon, or any combination thereof prior to being recycled to the reaction zone.

E115. The process of any one of E111 to E114, wherein at least one of the one or more fractions comprising all or a portion of the oligomer product is hydrogenated.

E116. The process comprising separating the stream comprising, consisting essentially of, or consisting of, the unreacted monomer and oligomer product of E101 or the second stream comprising, consisting essentially of, or consisting of, the unreacted monomer and oligomer product of any one of E102 to E109 into a third stream comprising, consisting essentially of, or consisting of, unreacted monomer and dimer and a fourth stream comprising, consisting essentially of, or consisting of, the trimer+ oligomers.

E117. The process of E116, further comprising separating the fourth stream comprising, consisting essentially of, or consisting of, the trimer+ oligomers into one or more fractions comprising all or a portion of the trimer+ oligomers.

E118. The process of E117, wherein the at least one of the one or more fractions comprising all or a portion of the trimer+ oligomers is selected from the group consisting of a) a fraction comprising 80 wt. % to 90 wt. % trimer and 8 wt. % to 18 wt. % tetramer, b) a fraction comprising 85 wt. % to 95 wt. % trimer and 3 wt. % to 13 wt. % tetramer, c) a fraction comprising 20 wt. % to 35 wt. % trimer, 40 wt. % to 60 wt. % tetramer, and 13 wt. % to 27 wt. % pentamer, d) a fraction comprising 35 wt. % to 55 wt. % trimer and 40 wt. % to 60 wt. % tetramer, e) a fraction comprising 45 wt. % to 65 wt. % tetramer, 22 wt. % to 34 wt. % pentamer, and 5 wt. % to 15 wt. % $C_{56}$ to $C_{64}$ hexamer, f) a fraction comprising 12 wt. % to 24 wt. % trimer, 37 wt. % to 57 wt. % tetramer, 13 wt. % to 25 wt. % pentamer, and 6 wt. % to 18 wt. % hexamer+, g) a fraction comprising 30 wt. % to 42 wt. % tetramer, 27 wt. % to 39 wt. % pentamer, 10 wt. % to 22 wt. % hexamer, and 9 wt. % to 21 wt. % heptamer+, and h) any combination fractions a) to g).

E119. The process of E117 or E120, wherein the third stream comprising, consisting essentially of, or consisting of, unreacted monomer and the dimer is recycled to the reaction zone.

E120. The process of E119, wherein the third stream comprising, consisting essentially of, or consisting of, unreacted monomer and dimer is contacted with a molecular sieve, alumina, silica gel, activated carbon, or any combination thereof prior to being recycled to the reaction zone.

E121. The process of any one of E117 to E120, wherein at least one of the one or more fractions comprising all or a portion of the trimer+ oligomers is hydrogenated.

E122. The process of any one of E110 to E121, wherein the separation of the stream comprising, consisting essentially of, or consisting of, the unreacted monomer and oligomer product is performed by distillation.

E123. The process of E110, wherein the fourth stream comprising, consisting essentially of, or consisting of, the oligomer product is hydrogenated. The hydrogenation of the fourth stream can yield a hydrogenated stream comprising, consisting essentially of, or consisting of a hydrogenated oligomer product.

E124. The process of E123, wherein the hydrogenated stream comprising, consisting essentially of, or consisting of a hydrogenated oligomer product is separated into one or more hydrogenated fractions of all or a portion of the hydrogenated oligomer product.

E125. The process of E116, wherein the fourth stream comprising, consisting essentially of, or consisting of, the trimer+ oligomers is hydrogenated to yield hydrogenated trimer+ oligomers. The hydrogenation of the fourth stream can yield a hydrogenated stream comprising, consisting essentially of, or consisting of a hydrogenated trimer+ oligomers.

E126. The process of E125, wherein the hydrogenated stream comprising, consisting essentially of, or consisting of a hydrogenated trimer+ oligomers is separated into one or more hydrogenated fractions of all or a portion of the hydrogenated trimer+ oligomers.

E127. The process of E100, wherein at least of the one or more fractions of all or a portion of the oligomer product is hydrogenated to yield one or more hydrogenated fractions.

E128. The process of any one of E101 and E104 to E109, wherein the stream comprising, consisting essentially of, or consisting of, the unreacted monomer and the oligomer product is hydrogenated to yield a hydrogenated stream comprising, consisting essentially of, or consisting of, hydrogenated oligomer product and optionally any residual unreacted monomer.

E129. The process E128, wherein the hydrogenated oligomer product is separated into one or more hydrogenated fractions of all or a portion of the hydrogenated oligomer product.

E130. The process wherein i) at least one of the one or more hydrogenated fractions comprising all or a portion of the hydrogenated oligomer product of E115, ii) at least one of the one or more hydrogenated fractions comprising all or a portion of the trimer+ oligomers of E121, iii) at least one of the one or more hydrogenated fractions comprising all or a portion of the hydrogenated oligomer product of E124, iv) at least one of the one or more hydrogenated fractions comprising all or a portion of hydrogenated trimer+ oligomers of E126, v) at least one of the one or more hydrogenated fractions of all or a portion of the oligomer product of E127, or vi) at least one of the one or more hydrogenated fractions of all or a portion of the hydrogenated oligomer product of E129 has a 100° C. kinematic viscosity from 1.8 cSt to 2.2 cSt, from 2.3 cSt to 2.7 cSt, from 2.6 cSt to 3.4 cSt, from 3.6 cSt to 4.4 cSt, from 4.6 cSt to 5.4 cSt, from 5.6 cSt to 6.4 cSt, from 6.6 cSt to 7.4 cSt, from 7.6 cSt to 8.4 cSt, from 8.6 cSt to 9.4 cSt, and from 9.6 cSt to 10.4 cSt.

E131. The process of any one of E1 to E131, further comprising controlling the average molecular weight (Mn) of the oligomer product by selecting an average molecular weight for the oligomer product and adjusting (i) a monomer to haloaluminate ionic liquid molar ratio, (ii) the halide of the halide component to aluminum of the haloaluminate ionic liquid molar ratio, or a combination of (i) and (ii) to achieve the selected average molecular weight of the oligomer product.

C1. A catalyst system comprising 1) a haloaluminate ionic liquid, and 2) a halide component comprising a Brönsted acid or an organohalide where a molar ratio of halide in the halide component to aluminum in the haloaluminate ionic liquid (minimum, maximum or range) can be any disclosed herein.

C2. The catalyst system of C1, wherein the haloaluminate ionic liquid is a trialkylammonium haloaluminate ionic liquid, a tetraalkylammonium haloaluminate ionic liquid, hydrogen pyridinium haloaluminate ionic liquid, an N-alkylpyridinium haloaluminate ionic liquid, an N,N'-dialkylimidizolium haloaluminate ionic liquid, or any combination thereof; alternatively, a tetraalkylammonium haloaluminate ionic liquid, an N-alkylpyridinium haloaluminate ionic liquid, an N,N'-dialkylimidizolium haloaluminate ionic liquid, or any combination thereof; alternatively, a tetraalkylammonium haloaluminate ionic liquid; alternatively, an N-alkylpyridinium haloaluminate ionic liquid; or alternatively, an N,N'-dialkylimidizolium haloaluminate ionic liquid.

C3. The catalyst system of any one of C1 to C2, wherein the ionic liquid is a chloroaluminate ionic liquid, a bromoaluminate ionic liquid, or any combination thereof; alternatively, a chloroaluminate ionic liquid; or alternatively, a bromoaluminate ionic liquid.

C4. The catalyst system of any one of C1 to C2, wherein the ionic liquid is N-(n-butyl)pyridinium bromoaluminate, N-(n-butyl)pyridinium chloroaluminate, or any combination thereof; alternatively, N-(n-butyl)pyridinium bromoaluminate; or alternatively, N-(n-butyl)pyridinium chloroaluminate.

C5. The catalyst system of any one of C1 to C4, wherein the halide component is a hydrogen halide; alternatively, hydrogen chloride, hydrogen bromide, or any combination thereof; alternatively, hydrogen chloride; or alternatively, hydrogen bromide.

C6. The catalyst system of any one of C1 to C4, wherein the halide component is a $C_1$ to $C_{12}$ organohalide; alternatively, a $C_2$ to $C_{12}$ organohalide; alternatively, a $C_3$ to $C_{12}$ organohalide; alternatively, a $C_1$ to $C_{12}$ alkyl halide; alternatively, a $C_2$ to $C_{12}$ alkyl halide; or alternatively, a $C_3$ to $C_{12}$ alkyl halide.

C7. The catalyst system of any one of C1 to C4, wherein the halide component is selected from the group consisting of a propyl halide, a butyl halide, a pentyl halide, a hexyl halide, a heptyl halide, an octyl halide, a nonyl halide, a decyl halide, and any combination thereof.

C8. The catalyst system of C6 or C7, wherein the organohalide is a primary organohalide (or a primary alkyl halide), a secondary organohalide (or a secondary alkyl halide), a tertiary organohalide (or a tertiary alkyl halide), or any combination thereof; alternatively, a secondary organohalide (or a secondary alkyl halide), a tertiary organohalide (or a tertiary alkyl halide), or any combination thereof; alternatively, a primary organohalide (or a primary alkyl halide); alternatively, a secondary organohalide (or a secondary alkyl halide); or alternatively, a tertiary organohalide (or a tertiary alkyl halide).

C9. The catalyst system of C6, C7, or C8, wherein organohalide (or an alkyl halide) is an organo chloride (or an alkyl halide), an organo bromide (or an alkyl bromide), an organo iodide (or an alkyl iodide), or any combination thereof; alternatively, an organo chloride (or an alkyl halide); alternatively, an organo bromide (or an alkyl bromide); or alternatively, an organo iodide (or an alkyl iodide).

C10. The catalyst system of any one of C1 to C9, wherein the catalyst system oligomerizes one or monomer at a temperature from 20° C. to 135° C.

C11. The catalyst system of any one of C1 to C9, wherein the catalyst system is used in the process E1 to E132.

C12. The catalyst system of C1, wherein the haloaluminate ionic liquid has a cationic portion comprising trialkylammonium, tetraalkylammonium, N-alkylpyridinium, or N',N"-dialkylimidizolium; alternatively, tetraalkylammonium, N-alkylpyridinium, or N',N"-dialkylimidizolium; alternatively, trialkyl ammonium; alternatively, tetraalkylammonium; alternatively, N-alkylpyridinium; or alternatively, N',N"-dialkylimidizolium.

C13. The catalyst system of C12, wherein the cationic portion which is trialkylammonium has a Structure ILC 1:

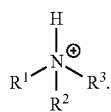

C14. The catalyst system of C12, wherein the cationic portion which is tetraalkylammonium has a Structure ILC 2:

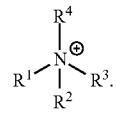

C15. The catalyst system of C12, wherein the cationic portion which is N-alkylpyridinium has a Structure ILC 3:

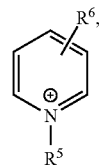

or Structure ILC 4:

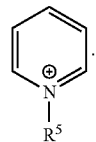

C16. The catalyst system of C12, wherein the cationic portion which is N',N"-dialkylimidizolium has a Structure ILC 5:

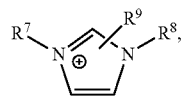

or Structure ILC 6:

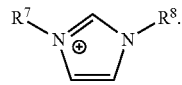

C17. The catalyst system of any one of C13 to C16, wherein each $R^1$, $R^2$, and $R^3$ of the trialkylammonium having Structure ILC 1, each $R^1$, $R^2$, $R^3$, and $R^4$ of the tetraalkylammonium having Structure ILC 2, each $R^5$ and $R^6$ of the N-alkylpyridinium having Structure ILC 3, each $R^5$ of the N-alkylpyridinium having Structure ILC 5, each $R^7$, $R^8$, and $R^9$ of the N',N"-dialkylimidizolium having Structure ILC 5, or each $R^7$ and $R^8$ of the N',N"-dialkylimidizolium having Structure ILC 6 independently can be a hydrocarbyl group.

C18. The catalyst system of C17, wherein each hydrocarbyl group which can be utilized as $R^1$, $R^2$, and $R^3$ of the trialkylammonium having Structure ILC 1, as $R^1$, $R^2$, $R^3$, and $R^4$ of the tetraalkylammonium having Structure ILC 2, as $R^5$ and $R^6$ of the N-alkylpyridinium having Structure ILC 3, as $R^5$ of the N-alkylpyridinium having Structure ILC 4, as $R^7$, $R^8$, and $R^9$ of the N',N"-dialkylimidizolium having Structure ILC 5, or as $R^7$ and $R^8$ of the N',N"-dialkylimidizolium having Structure ILC 6 independently can be an alkyl group, a phenyl group, or an alkyl substituted phenyl group; alternatively, a phenyl group or an alkyl substituted phenyl group; alternatively, an alkyl group; alternatively, a phenyl group; or alternatively, an alkyl substituted phenyl group.

C19. The catalyst system of any one of C17 to C18, wherein each hydrocarbyl group which can be utilized as $R^1$, $R^2$, and $R^3$ of the trialkylammonium having Structure ILC 1, as $R^1$, $R^2$, $R^3$, and $R^4$ of the tetraalkylammonium having Structure ILC 2, as $R^5$ and $R^6$ of the N-alkylpyridinium having Structure ILC 3, as $R^5$ of the N-alkylpyridinium having Structure ILC 4, as $R^7$, $R^8$, and $R^9$ of the N',N''-dialkylimidizolium having Structure ILC 5, or as $R^7$ and $R^8$ of the N',N''-dialkylimidizolium having Structure ILC 6 independently can be a $C_1$ to $C_{20}$ hydrocarbyl group; alternatively, a $C_1$ to $C_{15}$ hydrocarbyl group; alternatively, a $C_1$ to $C_{10}$ hydrocarbyl group; alternatively, a $C_1$ to $C_5$ hydrocarbyl group; alternatively, a phenyl group; alternatively, alternatively, a $C_7$ to $C_{20}$ alkyl substituted phenyl group; alternatively, a $C_7$ to $C_{15}$ alkyl substituted phenyl group; or alternatively, a $C_7$ to $C_{10}$ alkyl substituted group; alternatively, a $C_1$ to $C_{20}$ alkyl group; alternatively, a $C_1$ to $C_{15}$ alkyl group; or alternatively, a $C_1$ to $C_{10}$ alkyl group; or alternatively, a $C_1$ to $C_5$ alkyl group.

C20. The catalyst system of any one of C17 to C19, wherein each alkyl group which can be utilized as $R^1$, $R^2$, and $R^3$ of the trialkyl ammonium having Structure ILC 1, as $R^1$, $R^2$, $R^3$, and $R^4$ of the trialkylammonium having Structure ILC 2, as $R^5$ and $R^6$ of the N-alkylpyridinium having Structure ILC 3, $R^5$ of the N-alkylpyridinium having Structure ILC 4, as $R^7$, $R^8$, and $R^9$ of the N',N''-dialkylimidizolium having Structure ILC 5, as $R^7$ and $R^8$ of the N',N''-dialkylimidizolium having Structure ILC 6, or the alkyl substituent(s) for the alkyl substituted phenyl groups independently can be a methyl group, a ethyl group, a propyl group, a butyl group, a pentyl group, or a hexyl group; alternatively a methyl group, an ethyl group, an n-propyl group, an isopropyl group, an n-butyl group, a sec-butyl group, an isobutyl group, a tert-butyl group, an n-pentyl group, a 2-pentyl group, a 3-pentyl group, a 2-methyl-1-butyl group, a tert-pentyl group, a 3-methyl-1-butyl group, a 3-methyl-2-butyl group, or a neo-pentyl group; alternatively, a methyl group, an ethyl group, an isopropyl group, a tert-butyl group, or a neo-pentyl group; alternatively, a methyl group; alternatively, an ethyl group; alternatively, an isopropyl group; alternatively, a tert-butyl group; or alternatively, a neo-pentyl group.

Accordingly, the scope of protection is not limited by the description set out above but is only limited by the claims which follow, that scope including all equivalents of the subject matter of the claims. Each and every claim is incorporated into the specification as an embodiment of the present invention. Thus, the claims are a further description and are an addition to the detailed description of the present invention. The disclosures of all patents, patent applications, and publications cited herein are hereby incorporated by reference.

What is claimed is:

1. A process comprising;
   contacting i) a monomer comprising a $C_6$ to $C_{20}$ olefin, ii) a haloaluminate ionic liquid, and iii) a halide component comprising a $C_1$ to $C_{12}$ organohalide in a reaction zone; and
   oligomerizing the monomer in the reaction zone to form an oligomer product;
   wherein the oligomer product has an average molecular weight from 400 to 611 grams/mol,
   wherein the oligomer product is formed in a presence of less than 8 mol % isoparaffin based upon moles of monomer in the reaction zone,
   wherein a molar ratio of a halide in the halide component to an aluminum in the haloaluminate ionic liquid is at least 0.14:1, and
   wherein the oligomer product is formed at a temperature from 15° C. to 125° C.

2. The process of claim 1, wherein a molar ratio of carbon-carbon double bonds of the monomer to an aluminum in the haloaluminate ionic liquid is at least 15:1.

3. The process of claim 1, wherein a molar ratio of carbon-carbon double bonds of the monomer to an aluminum in the haloaluminate ionic liquid ranges from 15:1 to 1000:1, and the molar ratio of the halide in the halide component to the aluminum in the haloaluminate ionic liquid ranges from 0.14:1 to 7.5:1.

4. The process of claim 1, wherein the oligomer product is formed in the presence of less than 1 mol % isoparaffin based upon the moles of monomer in the reaction zone.

5. The process of claim 1, wherein the monomer comprises at least 75 mol % of the $C_5$ to $C_{20}$ olefin.

6. The process of claim 1, wherein the monomer is an alpha olefin.

7. The process of claim 1, wherein the haloaluminate ionic liquid is a trialkylammonium haloaluminate ionic liquid, a tetraalkylammonium haloaluminate ionic liquid, a hydrogen pyridinium haloaluminate ionic liquid, an N-alkylpyridinium haloaluminate ionic liquid, an N,N'-dialkylimidizolium haloaluminate ionic liquid, or any combination thereof.

8. The process of claim 1, wherein the haloaluminate ionic liquid is N-(n-butyl)pyridinium chloroaluminate, N-(n-butyl)pyridinium bromoaluminate, or any combination thereof.

9. The process of claim 1, wherein at least 50 wt % of the oligomer product comprises $C_{18}$-$C_{54}$ oligomers.

10. The process of claim 1, wherein the monomer comprises at least 90 mol % $C_8$ to $C_{12}$ normal alpha olefins.

11. The process of claim 1, further comprising:
   removing a reaction zone effluent from the reaction zone; and
   separating the reaction zone effluent into a first stream comprising the haloaluminate ionic liquid and a second stream comprising unreacted monomer and the oligomer product.

12. The process of claim 11, further comprising:
   isolating one or more fractions from the oligomer product from the second stream; and
   hydrogenating at least one of the one or more fractions from the oligomer product.

13. The process of claim 11, further comprising:
   recycling the unreacted monomer to the reaction zone.

14. The process of claim 1, further comprising:
   controlling the average molecular weight of the oligomer product by adjusting a molar ratio of the monomer to the haloaluminate ionic liquid, the molar ratio of the halide of the halide component to an aluminum of the haloaluminate ionic liquid, or both.

15. The process of claim 1, wherein the monomer is a normal alpha olefin.

16. The process of claim 1, wherein (1) the monomer comprises at least 90 mol % of the $C_6$ to $C_{20}$ olefin, and the $C_6$ to $C_{20}$ olefin is a normal alpha olefin, (2) the haloaluminate ionic liquid is a trialkylammonium haloaluminate ionic liquid, a tetraalkylammonium haloaluminate ionic liquid, a hydrogen pyridinium haloaluminate ionic liquid, an N-alkylpyridinium haloaluminate ionic liquid, an N,N'-dialkylimidizolium haloaluminate ionic liquid, or any combination thereof, (3) a molar ratio of carbon-carbon double bonds of the monomer to an aluminum in the haloaluminate ionic liquid ranges from 15:1 to 1000:1, and (4) the molar ratio of the halide in the halide component to the aluminum in the haloaluminate ionic liquid ranges from 0.14:1 to 7.5:1.

17. The process of claim wherein the oligomer product is formed in the presence of less than 6 mol % isoparaffin based upon the moles of monomer in the reaction zone.

18. The process of claim 1, wherein i) the monomer and the halide component are contacted prior to contacting the monomer with the haloaluminate ionic liquid, ii) the haloaluminate ionic liquid and the halide component are contacted prior to contacting the monomer with the haloaluminate ionic liquid, or iii) the monomer and the haloaluminate ionic liquid are contacted prior to contacting the haloaluminate ionic liquid with the halide component.

19. The process of claim 1, wherein a molar ratio of carbon-carbon double bonds of the monomer to an aluminum in the haloaluminate ionic liquid is at least 50:1.

20. The process of claim 1, wherein the oligomer product has an average molecular weight from 450 g/mol to 611 g/mol and the oligomer product comprises at least 75 wt. % $C_{18}$ to $C_{54}$ oligomers.

* * * * *